(12) United States Patent
Chen et al.

(10) Patent No.: US 9,222,106 B2
(45) Date of Patent: *Dec. 29, 2015

(54) ENHANCED EXPRESSION AND STABILITY REGIONS

(71) Applicant: Regeneron Pharmaceuticals, Inc., Tarrytown, NY (US)

(72) Inventors: Gang Chen, Yorktown Heights, NY (US); Robert Babb, Nanuet, NY (US); James P. Fandl, LaGrangeville, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 292 days.

This patent is subject to a terminal disclaimer.

(21) Appl. No.: 13/752,647

(22) Filed: Jan. 29, 2013

(65) Prior Publication Data

US 2013/0130372 A1    May 23, 2013

Related U.S. Application Data

(60) Division of application No. 12/793,898, filed on Jun. 4, 2010, now Pat. No. 8,389,239, which is a continuation of application No. 12/132,846, filed on Jun. 4, 2008, now Pat. No. 7,771,997.

(60) Provisional application No. 60/933,213, filed on Jun. 4, 2007.

(51) Int. Cl.
 *C12P 21/02* (2006.01)
 *C12N 15/85* (2006.01)
 *C12N 15/86* (2006.01)

(52) U.S. Cl.
 CPC ............... *C12N 15/85* (2013.01); *C12N 15/86* (2013.01); *C12N 2740/10043* (2013.01); *C12N 2800/30* (2013.01); *C12N 2840/203* (2013.01); *C12P 21/02* (2013.01)

(58) Field of Classification Search
 None
 See application file for complete search history.

(56) References Cited

U.S. PATENT DOCUMENTS

| | | | |
|---|---|---|---|
| 6,689,606 B2 | 2/2004 | Antoniou et al. | |
| 7,771,997 B2 * | 8/2010 | Chen et al. | 435/358 |
| 8,389,239 B2 * | 3/2013 | Chen et al. | 435/69.1 |

FOREIGN PATENT DOCUMENTS

WO    02081632 A2    10/2002

OTHER PUBLICATIONS

Aldrich, T.L., Viaje, A., and Morris, A.E. (2003) Biotechnol. Prog. 19:1433-1438.
Fukushige, S. and Sauer, B. (1992) PNAS 89:7905-7909.
Kito, M. et al. (2002) Appl. Micorbiol. Biotechnol. 60:442-448.
Koduri, R.K. et al. (2001) Gene 280:87-95.
Kwaks, T.H.J. and Otte, A.P. (2006) Trends in Biotechnology 24(3):137-142.
Mielke, C et al. (1996) Biochemistry 35:2239-2252.
Bouhassira, EE, et al. Blood, American Society of Hematology, 90(9): 3332-3344 (1997) (XP002143981).
Li, Q. et al. (2002) Blood, Nov. 1, 2002 100(9):3077-3086.
Shmerling, D. et al. Genesis the Journal of Genetics and Development 42(4): 229-235 (2005) (XP002496257).
Svetlova, E. Yu. Et al. (2001) Journal of Cellular Biochemistry Supplement 36:170-178.

* cited by examiner

*Primary Examiner* — Jim Ketter
(74) *Attorney, Agent, or Firm* — Mary C. Johnson; Joseph Zahner

(57) ABSTRACT

Expression-enhancing nucleotide sequences for expression in eukaryotic systems are provided that allow for enhanced and stable expression of recombinant proteins in eukaryotic cells. Enhanced expression and stability regions (EESYRs) are provided for expression of a gene of interest in a eukaryotic cell. Chromosomal loci, sequences, and vectors are provided for enhanced and stable expression of genes in eukaryotic cells.

32 Claims, 13 Drawing Sheets

Fig. 3A

```
EESYR          5032 TT-------------CCTGAGTTCCGCCAA-CGCCTAGTGACATCCTGTG----------   5067  SEQ ID NO:13
Rat Ch3 trim   5008 TTTATC-----TTTCCCTGGGACAGCCAA-AGCCTGGTGGCATCCTCTGTGAAGTGTTC   5061  SEQ ID NO:14
M Mus Ch2 trim 6021 TTTATC-----TTTCCCTGGGGACCGCCAA-AGCCTGGTGGCATACTGTACATTCTG---   6071  SEQ ID NO:15
H. Sap. Ch20 tr 5972 AGAAACACAACTTCTCCCAGGGAGAGTCAAGAGAGCAGTGTCATTTCCTATAAAATGCC   6031  SEQ ID NO:16
                    **    *    * ***   *   *** ***     *

EESYR          5068 --------CACACCCT------AAGGTGGCCTTTGTGTGGC------ACTGGCTTGGGTG   5107  SEQ ID NO:13
Rat Ch3 trim   5062 ATTCAAGACAGGCTCTGTCTTAAAGGTGGCCTTCGCATGGCGCTGGCACTGGCCGGGGCA   5121  SEQ ID NO:14
M Mus Ch2 trim 6072 --------TACACTGTTCATTCAAAACAGGCTCTGTCTTAAA-----GATGGTCTGAGCG   6118  SEQ ID NO:15
H. Sap. Ch20 tr 6032 A--AGGCCAATCCCAGGTCCCGGTGTCAGCCCTTGCGTGTGGC----ACTGGCACCAGCA   6085  SEQ ID NO:16
                      * *                * *    * *             ***     *

EESYR          5108 GTCGGGAAAGG-CATTTTCAGCTTGTT-GCAGAACTGCCACAGTAGCATGCTGGGT-CCG   5164  SEQ ID NO:13
Rat Ch3 trim   5122 GTCAGGAGAGGGTATTTTTAGCTTCTTTGCAGAATGGCCTCAGGAGCGTGCTGAGT-CTG   5180  SEQ ID NO:14
M Mus Ch2 trim 6119 GTCAGAAAAGGGTATTGTTAACTTGTTTGCAAAACTGCCTCAGGAGAGTGCTGAGT-GCG   6177  SEQ ID NO:15
H. Sap. Ch20 tr 6086 GCCAGAAAGGT-TACTTGTGACTTGTTTTCAGTGCTTTCCTGGGAGTGTCCTGAAAGCTG   6144  SEQ ID NO:16
                    * * *    *  *  ***  **  **   *   ** * ***       *

EESYR          5165 TGAAAGTTTCTGCCCGTTAACAAGAAGTCTCTACTACTTGTGACCTCACCA-----GTGA   5219  SEQ ID NO:13
Rat Ch3 trim   5181 TGAAAGTTGCTGCCAGTTAAGGAGAAGTCTCTACCACTCGTGACCTCACCA-----TTGA   5235  SEQ ID NO:14
M Mus Ch2 trim 6178 TGAAAGTGCTGCCCGTTAAGGAGAAGTCTCTACTACTTGTGATCTCACCA-----TCGA   6232  SEQ ID NO:15
H. Sap. Ch20 tr 6145 GCAGTGTTTCTGCCTCGTCAGAAGAGGCCTCATTCATTTGGGGTTGTACCAGCAACTTAA   6204  SEQ ID NO:16
                    *   *** *****  * *  *** * ***     * * *     ****       *

EESYR          5220 AAATTTCTTTAATTG------TCTCCTGGTGTTC-TGGGTTTTG--------CATTTTTGT   5265  SEQ ID NO:13
Rat Ch3 trim   5236 AAATTTCTTTAATTG------TCTCCTGGTGTTC-TGGGCTTTG--------CAGTTTTGT   5281  SEQ ID NO:14
M Mus Ch2 trim 6233 AAATTTCTTTAATTG------TCTCCTGGTGTTC-TGGGTTTTG--------CAGTTTTGT   6278  SEQ ID NO:15
H. Sap. Ch20 tr 6205 AAAGTTTTTTTTTTTCTTCCCTCTTCCAGTGTTAATAGATTTTGAAAGAGGCATTTTTGT   6264  SEQ ID NO:16
                    *** **  ***  **       *** *  ***** * * ****        ** ******

EESYR          5266 TTCTAAGGATACATTCCTGGGTGATGTCATGAAGTCCCCAAAGACACAGTG-GGGCTGTG   5324  SEQ ID NO:13
Rat Ch3 trim   5282 TCCTAAGGATACATTCTTGGGTGATGTCACGAAGTCCCCAAAGACACGGTG-GGGCTGTG   5340  SEQ ID NO:14
M Mus Ch2 trim 6279 TTCTAAGGATACATTCTTGGGTGATGTCACAAAGTCCCCAAAGACACGGTG-GAGCCTGTG   6337  SEQ ID NO:15
H. Sap. Ch20 tr 6265 TTCTAATTACAAATTCCTGGGTGATGTCATTAAGCCCTCAAACACCCGGTGAGGGCGGCA   6324  SEQ ID NO:16
                    * ****  *  *  ***** *************  *** ***** ** ** * *** *

EESYR          5325 TTGGATTGGGAAAGAT------------GATTTATCTGG-GGTGTCAAAAGGAAAAGAAG   5371  SEQ ID NO:13
Rat Ch3 trim   5341 TTAGATCGGGACAGACAATATTGCTGAGGATTTATCTGAAGAGTTCTGGCTC-AGCAACA   5400  SEQ ID NO:14
M Mus Ch2 trim 6338 TTAGATGGGGAAAGACAGT-CTGCTGAGGATTTATCTGGAACTGTCAGAAGGAAAAGAAG   6396  SEQ ID NO:15
H. Sap. Ch20 tr 6325 CTGAATGGGGAAAGACAATA-TGCTAACAAGTTATCTGAGGGTGTCAGAAAGAAAATGATG   6383  SEQ ID NO:16
                    *  ** **** ***         * *******    ***** **  **   *   ** *

EESYR          5372 GGAAACAGG-CACTTGGGA-AAATGTCCTCCCGCCCACCCGAATTTTGGCTT-GGCAACC   5428  SEQ ID NO:13
Rat Ch3 trim   5401 GGAAACAGGCACTCAGGG-AAATGTCCTCTAGTCT----GAGTTCTGGCTC-AGCAACA   5454  SEQ ID NO:14
M Mus Ch2 trim 6397 GTAAATGGGGCACTTGGGA-AAGTGGCCTCTAGTTT----GACTTCTGGCTT-AGCAAAG   6450  SEQ ID NO:15
H. Sap. Ch20 tr 6384 AAAAACAGTACAGTTGGGGGAAATGTTTTCCAGCCT----GCTTTCTGGTTTTAGCGACT   6439  SEQ ID NO:16
                    ***  *    **  *   * * **  * **       * ** *****  ** **

EESYR          5429 GT-GGTGGAGGAGCAAGAAACACGTGGACGTTTGA-GGAGGCAT-GGGGTCCTAGGAGGA   5485  SEQ ID NO:13
Rat Ch3 trim   5455 GA-GGTGGGGAGATAAGGCACAGTGGTTAGAAGGAGTCATCAGGGGTTCTGGGAGGA   5513  SEQ ID NO:14
M Mus Ch2 trim 6451 GT-TGTGGGGAGATAAGGCATACACAGTAGTTAGCAGGAGGCAACAGGGGTCCTGGGAGGA   6509  SEQ ID NO:15
H. Sap. Ch20 tr 6440 GCATGGGAAGAGATAAGACACACATGGCTTTTATAAGGAGCCATCGGGATCTCTAGGGGA   6499  SEQ ID NO:16
                     *   * *   *   **   *** *  ****        * *  **  ** *  **

EESYR          5486 CAGGAAGCAGAAGGAGAGAGCTGGGCTGACAGCCTGCAGGCATTGCACAGTTTC---AGAA   5543  SEQ ID NO:13
Rat Ch3 trim   5514 CAGGAGGCAGGAG-----AGGCAGGGCTGACAGTGTGCAATCATTGTGTAGTCTC--CCAA   5567  SEQ ID NO:14
M Mus Ch2 trim 6510 CGCGAGGCAGAAGGAG-AGGCTGGGCTGACAGCATGCAATCATTGCATAGTCTC--CAAA   6566  SEQ ID NO:15
H. Sap. Ch20 tr 6500 CATGAGGCAGGAGAAAAGAATTGGGCTGAAAGCATCCAATCATCACATATTCACGGAGAA   6559  SEQ ID NO:16
                    *  ** ****  **      *******  **    ***    ***    *    *  **

EESYR          5544 GGAGATTACAGCATGACTGAG------TTTTAGGGATCCAACAGGGACCTG---GGTAG   5594  SEQ ID NO:13
Rat Ch3 trim   5568 GGAGATTACAACATGGCTGAA------TTTTCAGGGGTCCAACGGAGACTGT---AGTGG   5618  SEQ ID NO:14
M Mus Ch2 trim 6567 GGAGATTGCAACATGGCTGAG------TTTTCAGAGGTCCTACAGAGCCCGT---GGTAG   6617  SEQ ID NO:15
H. Sap. Ch20 tr 6560 AGAGATTACAATATAGCAGAGGAAGCTCTTCCAGGGCTCCTACAGGGACCTTTGGGACAA   6619  SEQ ID NO:16
                    ****** **  ** * **       **  **  *** ** **  *   *

EESYR          5595 AGATTCTGTGGGCTCTGAGGCAACTTGACCTCAGCCAGATGGTATTTGAATAACCTGCTC   5654  SEQ ID NO:13
Rat Ch3 trim   5619 AGATTCTGTGGGTTCTGAGCAACTTGACCTCAGCCAGATGGTATTTGAATAACCTGC------   5672  SEQ ID NO:14
M Mus Ch2 trim 6618 AGATTCTGTGGGTTCTGAGACAACTTGACTTTAGCCAGATGGTATTTGAGTAATCTGG-   6676  SEQ ID NO:15
H. Sap. Ch20 tr 6620 AGATTCAGTGGGCTTTGGGACAGCTTGACTTCAACTAGATGGTATTTGAATAATCTGCT-   6678  SEQ ID NO:16
                    ****** ***** *    * ** ****** *  *  ****** ****** *** ***
```

Fig. 3B

```
EESYR          5655  TTAGAGGGAAAACAGACATAGCAAACAGAGCCACGTTTAGTGATGAAACTCTCACTTTGC  5714   SEQ ID NO:17
Rat Ch3 trim   5673  --------------AGCTCCAGCAAGCACAGCCACATTTAGGGATGAAACTCTCACTTTGA  5719   SEQ ID NO:18
M Mus Ch2 trim 6677  --AGAGAGAAAACAGCTACAGCAAACAGGGCCACATTTAGTGACGAAACTCTCACTTTGA  6734   SEQ ID NO:19
H. Sap. Ch20 tr 6679 --GGAGAGAAAACAGATATAGCCACACACTGTCACATTTAGCGTTGAAACTCTCGGTTTGA 6736   SEQ ID NO:20
                      **   ****  **   *  ***  *****  *  *********  ****

EESYR          5715  CTG---AGTCATGTGCGGCCATGCCCAGGGGTCAGGCTGACACTCAACTCAAAAACAAGT  5771   SEQ ID NO:17
Rat Ch3 trim   5720  CTGT-GAGTCACGTGTAGCTGTGTCCCGAGGTCAGGCTGGCCCTCAGCTCAAAAACAAGT  5778   SEQ ID NO:18
M Mus Ch2 trim 6735  CTGTTGAGTCATTTGCAG-TGGGCCCTGAGGTCAGGCTGGCCCTCAGCTCAAAAACAAGC  6793   SEQ ID NO:19
H. Sap. Ch20 tr 6737 CTAT-GAGTAATGTTCAGCCATGCCCAAGGGTCAGGCCTACACTCA-CTCAGAAACAAGT  6794   SEQ ID NO:20
                      **   ***  *    *    *    ***  ********   *  ****  **** *******

EESYR          5772  GAGAAATTGAAG-----------ACAATCCGTGGTGGCAGCTACTGGAA-GGGCCACCAC  5819   SEQ ID NO:17
Rat Ch3 trim   5779  GAGGGATTGAAGCAATTACTCAGATAATTCACAGCCACAGCTACGGGGA-GGGCCGC---  5834   SEQ ID NO:18
M Mus Ch2 trim 6794  GAGGAACTGAAGCAATTACTCAGATAATCCACAGCCACAGCCACTGGAAAGGGCCAC---  6850   SEQ ID NO:19
H. Sap. Ch20 tr 6795 GGGGAATTGAAGCAATTATTCAGATAATCCATAGACATAGCTACTGGCCAGTGCTGC---  6851   SEQ ID NO:20
                      *  *  *****            *  ***  *   *    ***  ** **    * **  *

EESYR          5820  ATCCCCAGAAAGAGT------GGAGCTGCTAAAAAGCCAT--------TTGTGATAGGCA  5865   SEQ ID NO:17
Rat Ch3 trim   5835  ATCCCCAGAAACATC------GGGGTTACTATAAAGCTA-----------GTGGTGGTCA  5877   SEQ ID NO:18
M Mus Ch2 trim 6851  ATCCCCAGAGACAGCACAGCAGGGGTGGGGGTGGGCTATGAGAAAGTTAGTGATTGTAG   6910   SEQ ID NO:19
H. Sap. Ch20 tr 6852 -ACCCCTGATTTAGCCCA---GAAACAGTAATGCTATTATAAGCT-GTTGGTGATTTGTG 6906   SEQ ID NO:20
                      ****  **      *                    *            ***  *

EESYR          5866  CAGTTATCTTGAATGCATGGAGCAGAG---ATTACGGAAAAATCGAGAATGTTAATGAGG  5922   SEQ ID NO:17
Rat Ch3 trim   5878  CAGTTATCTTGAATGTATGGAGCAGAGGAGATTACAGAAAAACCTAGAATGTTAATGAGG  5937   SEQ ID NO:18
M Mus Ch2 trim 6911  CAGTTATCTAGAATGTGCGGAGCAGAGGAGGTTACACAAAAACCTAGAATG---------  6961   SEQ ID NO:19
H. Sap. Ch20 tr 6907 GAGCAATCTTGAATTTATTAAGGAAAGGAGATTATAGAAAAATCCAGAATGCCAATG-GG 6965   SEQ ID NO:20
                      **  ****  ****       **  *  **   ***   ***** * ******
```

ENHANCED EXPRESSION AND STABILITY REGIONS

CROSS-REFERENCE TO RELATED APPLICATIONS

This application is a divisional of U.S. application Ser. No. 12/793,898, filed on 4 Jun. 2010, which is a continuation of U.S. non-provisional application Ser. No. 12/132,846, now U.S. Pat. No. 7,771,997, filed 4 Jun. 2008, which claims benefit under 35 USC 119(e) of U.S. Provisional application No. 60/933,213, filed 4 Jun. 2007, all of which are herein specifically incorporated by reference in their entirety.

This application hereby incorporates by reference the Sequence Listing submitted in Computer Readable Form as file 3051B_ST25.txt created on Sep. 18, 2012 (79,397 bytes).

BACKGROUND

1. Field of the Invention

The invention provides for expressing recombinant proteins in eukaryotic cells. In particular, the invention includes methods and compositions for improved expression of proteins in eukaryotic cells by employing expression-enhancing nucleotide sequences. The invention includes enhanced expression and stability region (EESYR) sequences that facilitate enhanced and stable expression of recombinant proteins in eukaryotic cells, and methods of using such sequences.

2. Description of Related Art

The development of expression systems is an important goal for providing a reliable and efficient source of a given protein for research and therapeutic use. Recombinant protein expression in mammalian cells is often preferred for manufacturing therapeutic proteins due to, for example, the ability of mammalian expression systems to appropriately post-translationally modify recombinant proteins.

Several vectors are available for expression in mammalian hosts, each containing various combinations of cis- and, in some cases, trans-regulatory elements to achieve high levels of recombinant protein with short incubation times. Despite the availability of numerous such vectors, the expression of a recombinant protein achieved in mammalian systems is often unacceptably low or otherwise unsatisfactory. Moreover, developing a cell line that reliably expresses sufficiently high levels of a desired protein often requires time consuming cloning and amplification steps. Accordingly, there is a need in the art for improved mammalian expression systems.

BRIEF SUMMARY

In one aspect, an isolated nucleotide sequence comprising an expression-enhancing sequence selected from a sequence of SEQ ID NO:1-6, or an expression-enhancing fragment thereof, is provided.

In one embodiment, the expression-enhancing sequence comprises an expression-enhancing sequence of SEQ ID NO:5 located at a position within SEQ ID NO:5 selected from nucleotides spanning positions numbered 10-13,515; 20-12,020; 1,020-11,020; 2,020-10,020; 3,020-9,020; 4,020-8,020; 5,020-7,020; 6,020-6,920; 6,120-6,820; 6,220-6,720; 6,320-6,620; 6,420-6,520; 6,460-6,500; 6,470-6,490; and 6,475-6,485. In another embodiment, an expression-enhancing sequence is provided that is selected from the group consisting of nucleotides 5,000-7,400 of SEQ ID NO:5; 5,000-6,500 of SEQ ID NO:5; 6,400-7,400 of SEQ ID NO:5; and nucleotides 6,400-6,500 of SEQ ID NO:5.

In another embodiment, the recombination recognition site is positioned as described above, providing that the expression-enhancing sequence comprises a sequence that is at least 90% identical, more preferably at least 95% identical, most preferably at least 99% identical, to the expression-enhancing sequence of SEQ ID NO:5 or an expression-enhancing fragment thereof.

In one embodiment, the expression-enhancing sequence further comprises at least one recombinase recognition site comprising a sequence independently selected from a loxp site, a lox 511 site, a lox 2272 site, and a frt site. In one embodiment, the recombinase recognition site is within the expression-enhancing sequence. In another embodiment, the recombinase recognition site is immediately adjacent in the 5' direction to the terminal nucleotide of the 5' end or immediately adjacent in the 3' direction to the terminal nucleotide of the 3' end of the expression-enhancing sequence.

In one embodiment, at least two recombinase recognition sites are present within the expression-enhancing sequence. In a specific embodiment, two recombinase recognition sites of opposite orientation are present within the expression-enhancing sequence. In another embodiment, three recombinase recognition sites are present within the expression-enhancing sequence.

In one aspect, an isolated nucleotide sequence is provided that comprises an expression-enhancing sequence that is at least 80% identical, preferably at least 90% identical, more preferably at least 95% identical, most preferably at least 99% identical to an expression-enhancing sequence of SEQ ID NO:1-6 or an expression-enhancing fragment thereof. In one embodiment, the expression-enhancing sequence displays the recited identity to a sequence of SEQ ID NO:5 as described above.

In one aspect, an isolated eukaryotic cell is provided that comprises an expression-enhancing sequence selected from SEQ ID NO:1-6 or an expression-enhancing fragment thereof. In one embodiment, the expression-enhancing sequence comprises an expression enhancing sequence of SEQ ID NO:5 as described above.

In one embodiment, the eukaryotic cell is a mouse, rat, hamster, or human cell. In a specific embodiment, the eukaryotic cell is a CHO cell.

In one embodiment, the eukaryotic cell further comprises at least one recombinase recognition sequence within the expression-enhancing sequence. In a specific embodiment, the at least one recombinase recognition sequence is independently selected from a loxp site, a lox 511 site, a lox 2272 site, and a frt site. In one embodiment, the recombinase recognition site is immediately adjacent in the 5' direction to the terminal nucleotide of the 5' end or immediately adjacent in the 3' direction to the terminal nucleotide of the 3' end of the expression-enhancing sequence.

In one embodiment, at least two recombinase recognition sites are present within the expression-enhancing sequence. In a specific embodiment, two recombinase recognition sites are of opposite orientation and are present within the expression-enhancing sequence. In another embodiment, three recombinase recognition sequences are present, and one of the three recombinase recognition sequences is in an orientation opposite to the two remaining recombinase recognition sequences.

In one embodiment, the recombinase recognition site in the expression-enhancing sequence of SEQ ID NO:5 is located at a position within SEQ ID NO:5 selected from nucleotides spanning positions numbered 10-13,515; 20-12,020; 1,020-11,020; 2,020-10,020; 3,020-9,020; 4,020-8,020; 5,020-7,020; 6,020-6,920; 6,120-6,820; 6,220-6,720; 6,320-6,620;

6,420-6,520; 6,460-6,500; 6,470-6,490; and 6,475-6,485. In another embodiment, the recombinase recognition site in in a sequence that is selected from the group consisting of nucleotides 5,000-7,400 of SEQ ID NO:5; 5,000-6,500 of SEQ ID NO:5; 6,400-7,400 of SEQ ID NO:5; and nucleotides 6,400-6,500 of SEQ ID NO:5. In a specific embodiment, the recombinase recognition site is located within nucleotides 6400-6500 of SEQ ID NO:5. In another specific embodiment, the recombinase recognition site is inserted before, after, or within the "act" triplet of nucleotides 6471 to 6473 of SEQ ID NO:5 in an expression-enhancing sequence of SEQ ID NO:5.

In another specific embodiment, the recombination recognition site is positioned as described above, with the caveat that the expression-enhancing sequence comprises a sequence that is at least 90% identical, more preferably at least 95% identical, most preferably at least 99% identical, to nucleotides 5218 through 6048 of SEQ ID NO:5 or an expression-enhancing fragment thereof.

In a specific embodiment, the cell is a CHO cell and the recombinase recognition site is inserted in the CHO cell genome at or within the "act" triplet of nucleotides 6,471 to 6,473 of SEQ ID NO:5.

In one embodiment, a first GOI is inserted within the expression-enhancing sequence of SEQ ID NO:5 as described above, and the first GOI is optionally operably linked to a promoter, wherein the promoter-linked GOI (or the GOD is flanked 5' by a first recombinase recognition site and 3' by a second recombinase recognition site. In another embodiment, a second GOI is inserted 3' of the second recombinase recognition site, and the second GOI is flanked 3' by a third recombinase recognition site.

In a specific embodiment, the GOI is operably linked to a promoter capable of driving expression of the GOI, wherein the promoter comprises a eukaryotic promoter that is regulatable by an activator or inhibitor. In another specific embodiment, the eukaryotic promoter is operably linked to a prokaryotic operator, and the eukaryotic cell optionally further comprises a prokaryotic repressor protein.

In another embodiment, one or more selectable markers are included between the first and the second and/or the second and the third recombinase recognition sites. In a specific embodiment, the first and/or the second genes of interest and/or the one or more selectable markers are operably linked to a promoter, wherein the promoter may be the same or different. In a specific embodiment, the promoter comprises a eukaryotic promoter (such as, for example, a CMV promoter), optionally controlled by a prokaryotic operator (such as, for example, a tet operator). In a specific embodiment, the cell further comprises a gene encoding a prokaryotic repressor (such as, for example, a tet repressor).

In another embodiment, the cell further comprises a gene capable of expressing a recombinase. In a specific embodiment, the recombinase is a Cre recombinase.

In one aspect, an isolated eukaryotic cell is provided that comprises an expression-enhancing sequence that is at least 80%, more preferably at least 90%, more preferably at least 95%, most preferably at least 99% identical to an expression-enhancing sequence of SEQ ID NO:1-6 or an expression-enhancing fragment thereof. In a specific embodiment, expression-enhancing sequence is a sequence within SEQ ID NO:5 as described above.

In one aspect, a eukaryotic host cell is provided, comprising an expression-enhancing sequence selected from SEQ ID NO:1-6 or an expression-enhancing fragment thereof, comprising a first recombinase recognition site followed by a first eukaryotic promoter, a first marker gene, a second eukaryotic promoter, a second marker gene, a second recombinase recognition site, a third eukaryotic promoter, a third marker gene, and a third recombinase recognition site. In one embodiment, the expression-enhancing sequence is within SEQ ID NO:5 as described above.

In one embodiment, the first, second, and third recombinase recognition sites are different. In a specific embodiment, the recombinase recognition sites are selected from a loxp site, a lox 511 site, a lox 2272 site, and a frt site.

In one embodiment, the first marker gene is a drug resistance gene. In a specific embodiment, the drug resistance gene is a puromycin resistance gene. In another embodiment, the second and third marker genes encode two different fluorescent proteins. In one embodiment, the two different fluorescent proteins are selected from *Discosoma* coral (DsRed), green fluorescent protein (GFP), enhanced green fluorescent protein (eGFP), cyano fluorescent protein (CFP), enhanced cyano fluorescent protein (eCFP), and yellow fluorescent protein (YFP). In a specific embodiment, the two different fluorescent proteins are eCFP and DsRed.

In one embodiment, the first, second, and third promoters are the same. In another embodiment, the first, second, and third promoters are different. In another embodiment, the first promoter is different from the second and third promoters, and the second and third promoters are the same. In a specific embodiment, the first promoter is an SV40 late promoter, and the second an third promoters are each a human CMV promoter.

In one aspect, a eukaryotic host cell is provided, comprising an expression-enhancing sequence selected from SEQ ID NO:1-6, or an expression-enhancing fragment thereof, at least one recombinase recognition site within the expression-enhancing sequence, and at least one gene of interest (GOI) within the expression-enhancing sequence. In one embodiment, the expression-enhancing sequence is a sequence within SEQ ID NO:5, as described above.

In one embodiment, the cell comprises a first recombinase recognition site followed by a first promoter operably linked to a first GOI. In another embodiment, the first GOI is followed by a second recombinase recognition site. In another embodiment, the second recombinase recognition site is followed by a second promoter operably linked to a second GOI. In another embodiment, the second GOI is followed by a third recombinase recognition site. In another embodiment, at least one marker is operably linked to a third promoter and is located between the second recombinase recognition site and the second promoter. In one embodiment, the first recombinase recognition site is oriented in an opposite orientation to the second and third recombinase recognition sites. In one embodiment the first and second promoters are eukaryotic promoters operably linked to a prokaryotic operator. In one embodiment, the first and second promoters are CMV promoters operably linked to tet operator sequences. In another embodiment, the cell further comprises a gene capable of expressing a prokaryotic repressor. In one embodiment, the prokaryotic repressor is a tet repressor. In one embodiment, the cell comprises a gene capable of expressing a Cre recombinase.

In one embodiment, a first and a second marker gene are located between the second recombinase recognition site and the second promoter, and an IRES is between the first and second marker genes. In another embodiment, the first codon (ATG) of the first marker gene is immediately 5' to the second recombinase recognition site, and the second codon of the first marker gene is immediately 3' to the second recombinase recognition site. In another embodiment, the first marker gene contains an intron and the second recombinase recognition site is located within the intron such that the amino-terminal half of the first marker gene and the 5' half of the intron are located 5' of the second recombinase recognition site and the 3' half of the intron and carboxy-terminal half of the first marker gene are immediately 3' to the second recombinase recognition site.

In one embodiment, the first, second, and third recombinase recognition sites are different. In a specific embodiment, the recombinase recognition sites are selected from a loxp site, a lox 511 site, a lox 2272 site, and a frt site.

In one embodiment, the first marker gene is a drug resistance gene. In a specific embodiment, the drug resistance gene is a hygromycin resistance gene. In another embodiment, the second marker gene encodes a fluorescent protein. In one embodiment, the fluorescent protein is selected from DsRed, GFP, eGFP, CFP, eCFP, and YFP.

In one embodiment, the first, second, and third promoters are the same. In another embodiment, the first, second, and third promoters are different. In another embodiment, the third promoter is different from the first and second promoters, and the first and second promoters are the same. In a specific embodiment, the third promoter is an SV40 late promoter, and the first and second promoters are each a human CMV promoter.

In one embodiment, the first and second promoters are operably linked to a prokaryotic operator. In a specific embodiment, the operator is a tet operator.

In one embodiment, the host cell line has an exogenously added gene encoding a recombinase integrated into its genome, operably linked to a promoter. In a specific embodiment, the recombinase is Cre recombinase. In another embodiment, the host cell has a gene encoding a regulatory protein integrated into its genome, operably linked to a promoter. In a specific embodiment, the regulatory protein is a tet repressor protein.

In one embodiment, the first GOI and the second GOI encode a light chain, or fragment thereof, of an antibody or a heavy chain, or fragment thereof, of an antibody. In a specific embodiment, the first GOI encodes a light chain of an antibody and the second GOI encodes a heavy chain of an antibody.

In one aspect, a method is provided for making a protein of interest, comprising: (a) providing a host cell that comprises an expression-enhancing sequence selected from a sequence of SEQ ID NO:1-6; (b) introducing into the host cell, within the expression-enhancing sequence, a gene of interest (GOI) operably linked to a promoter; (c) maintaining the host cell of (a) under conditions that allow the GOI to express a protein of interest; and, (c) recovering the protein of interest.

In one embodiment, the cell is a CHO cell and the nucleotide sequence is an expression-enhancing sequence of SEQ ID NO:5 as described above.

In one embodiment, the GOI is introduced into the cell employing a targeting vector for homologous recombination, wherein the targeting vector comprises a 5' homology arm homologous to a sequence present in at least one of SEQ ID NO:1-6, a GOI, and a 3' homology arm homologous to a sequence present in at least one of SEQ ID NO:1-6. In another embodiment, the construct further comprises two, three, four, or five or more genes of interest. In another embodiment, one or more of the genes of interest are operably linked to a promoter.

In another embodiment, the GOI is introduced employing an integrase technology, for example, integrase technology employing att sites such as Invitrogen's Gateway™ and Multisite Gateway™ cloning systems which employ bacteriophage lambda att site recombination.

In another embodiment, the expression-enhancing sequence comprises one or more recombinase recognition sites as described above, and the GOI is introduced into the expression-enhancing sequence through the action of a recombinase that recognizes the recombinase recognition site.

In one embodiment, the expression-enhancing sequence comprises two recombinase recognition sites.

In one embodiment, the expression-enhancing sequence comprises a first, a second, and a third recombinase recognition site. In one embodiment, the first, second, and third recombinase recognition sites are different. In another embodiment, the first, second, and third recombinase recognition sites are not in the same orientation. In a specific embodiment, the first site is 5' to the second site, and the second site is 5' to the third site. In another specific embodiment, the second and third sites are in opposite orientation with respect to the first site.

In another embodiment, a first and a second GOI are introduced into the expression-enhancing sequence. In one embodiment, the first GOI is introduced between the first and the second recombinase recognition sites, and the second GOI is introduced between the second and the third recombinase recognition sites. In a specific embodiment, the recombinase recognition sites are independently selected from a loxp site, a lox 511 site, a lox 2272 site, and a frt site.

In another embodiment, the first GOI flanked by recombinase recognition sites on a first vector and the second GOI flanked by recombinase recognition sites on a second vector are introduced into a cell comprising an expression-enhancing sequence that comprises three recombinase recognition sites in a single step.

In one embodiment, the GOI is operably linked to a eukaryotic promoter. In another embodiment, the eukaryotic promoter is operably linked to a prokaryotic operator. In a specific embodiment, the eukaryotic promoter is a CMV promoter and the prokaryotic operator is a tet operator.

In another embodiment, the cell comprises a gene capable of expressing a prokaryotic repressor. In a specific embodiment, the prokaryotic repressor is a tet repressor.

In another embodiment, the cell comprises a gene capable of expressing a recombinase. In a specific embodiment, the recombinase is a Cre recombinase.

In one aspect, a eukaryotic cell is provided, wherein the eukaryotic cell comprises at least one expression-enhancing sequence of SEQ ID NO:1-6 and at least one exogenously added gene within the expression-enhancing sequence. In one embodiment, the exogenously added gene is operably linked to an exogenously added promoter.

In one embodiment, the expression-enhancing sequence is a sequence of SEQ ID NO:5, and the at least one exogenously added gene integrated or inserted within the expression-enhancing sequence is a human gene. In a specific embodiment, the eukaryotic cell is a CHO cell, the exogenously added gene is a human gene, and the human gene is operably linked to an exogenously added eukaryotic promoter.

In one aspect, a targeting vector for homologous recombination is provided, wherein the targeting vector comprises a 5' homology arm, a GOI, and a 3' homology arm, wherein each homology arm is homologous to a sequence within one of SEQ ID NO:1-6. In one embodiment, the 5' and 3' homology arms are homologous to sequences within SEQ ID NO:5. In one embodiment, the targeting vector comprises two, three, four, or five or more genes of interest. In one embodiment, the GOI is operably linked to a promoter. In another embodiment, each of the two, three, four, or five or more genes of interest are each operably linked to a promoter.

In one aspect, an expression vector is provided, comprising an expression-enhancing nucleotide sequence selected from SEQ ID NO: 1-6 or an expression-enhancing fragment thereof. In one embodiment, the expression-enhancing sequence is within SEQ ID NO:5 as described above.

In one embodiment, the vector further comprises a promoter. In a specific embodiment, the promoter is a human CMV promoter.

In one embodiment, the vector further comprises a cloning site for an expressible gene of interest (GOI). In one embodiment, the nucleotide sequence selected from SEQ ID NO: 1-6 or expression-enhancing fragment thereof is located 3' with respect to the coning site for the expressible GOI. In another embodiment, the nucleotide sequence selected from SEQ ID NO: 1-6 or expression-enhancing fragment thereof is located 5' with respect to the coning site for the expressible GOI.

In a specific embodiment, the vector comprises a nucleotide sequence selected from SEQ ID NO:1-6 or an expression-enhancing fragment, a human CMV promoter, a GOI, and a termination sequence, wherein the nucleotide sequence selected from SEQ ID NO: 1-6, or the expression-enhancing fragment thereof, is located 5' with respect to the CMV promoter. In a specific embodiment, the vector further comprises an intron selected from a CMV-MIE intron and a rabbit β-globin intron.

In one aspect, an expression vector is provided, comprising an expression-enhancing nucleotide sequence that is at least 80% identical, preferably at least 90% identical, more preferably at least 95% identical, most preferably at least 99% identical to a sequence selected from SEQ ID NO:1-6 or an expression-enhancing fragment thereof.

In one aspect, a method is provided for making a protein of interest, comprising: (a) introducing into a host cell an expression vector comprising an expression-enhancing sequence selected from a sequence within SEQ ID NO:1-6 and a GOI that encodes for a protein of interest, wherein the GOI is operably linked to a promoter and operably linked to the expression-enhancing sequence; (b) culturing the host cell of (a) under conditions that allow expression of the GOI; and (c) recovering the protein of interest.

In one embodiment, the enhanced expression and stability region sequence is an expression-enhancing sequence of SEQ ID NO:1-6. In one embodiment, the expression-enhancing sequence is within SEQ ID NO:5 as described above.

In one embodiment, the recombinant protein is selected from the group consisting of a subunit of an immunoglobulin or fragment thereof and a receptor or ligand-binding fragment thereof. In a specific embodiment, the recombinant protein is selected from the group consisting of an antibody light chain or antigen-specific fragment thereof, and an antibody heavy chain or antigen-specific fragment thereof.

In any of the aspects and embodiments described above, the expression-enhancing sequence can be placed in the indicated orientation as indicated in SEQ ID NO:1-6, or in the reverse of the orientation indicated in SEQ ID NO:1-6.

Any of the aspects and embodiments of the invention can be used in conjunction with any other aspect or embodiment of the invention, unless otherwise specified or apparent from the context.

Other objects and advantages will become apparent from a review of the ensuing detailed description.

BRIEF DESCRIPTION OF THE FIGURES

FIGS. 3A and 3B show an alignment of Chinese hamster ovary (CHO), mouse, human, and rat EESYR sequences for a fragment of SEQ ID NO:5.

DETAILED DESCRIPTION

Figure 1:
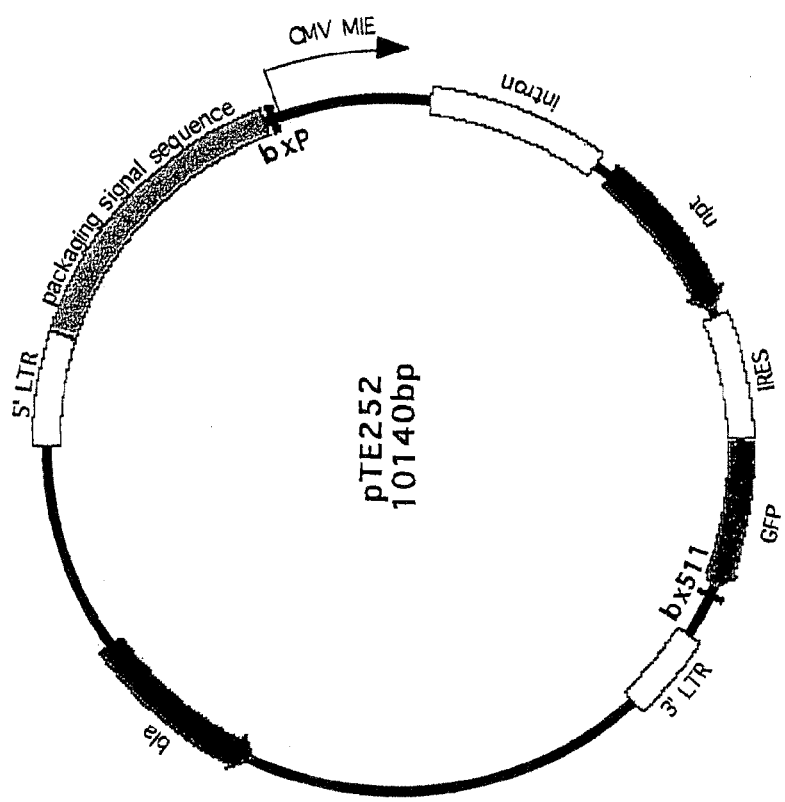
FIG. 1. Schematic diagram of a retroviral construct, pTE252, used for the introduction of nucleic acid construct into a cell genome. LTR: long terminal repeat; LoxP: Cre recombinase recognition sequence: ATAACTTCGTATAAT-GTATGCTATACGAAGTTGT (SEQ ID NO:7); Lox511: a mutation of LoxP sequences: ATAACTTCGTATAATG-TATACTATACGAAGTTAG (SEQ ID NO:8); the Lox511 sequence is recognized by Cre recombinase but the Lox511 site does not recombine with a LoxP site. GFP: Green fluorescent protein; CMV MIE: human cytomegalovirus major immediate early promoter; npt: neomycin phosphotransferase; bla: beta lactamase; IRES: internal ribosomal entry site.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure.

Unless defined otherwise, or otherwise specified, all technical and scientific terms used herein have the same meaning as commonly understood by one of ordinary skill in the art to which this invention belongs.

Although any methods and materials similar or equivalent to those described herein can be used in the practice or testing of the present invention, particular methods and materials are now described. All publications mentioned herein are incorporated herein by reference in their entirety.

DEFINITIONS

DNA regions are operably linked when they are functionally related to each other. For example, a promoter is operably linked to a coding sequence if the promoter is capable of participating in the transcription of the sequence; a ribosome-binding site is operably linked to a coding sequence if it is positioned so as to permit translation. Generally, operably linked can include, but does not require, contiguity. In the case of sequences such as secretory leaders, contiguity and proper placement in a reading frame are typical features. An EESYR is operably linked to a GOI where it is functionally related to the gene of interest, for example, where its presence results in enhanced expression of the GOI.

The term "enhanced" when used to describe enhanced expression includes an enhancement of at least about 1.5-fold to at least about 2-fold enhancement in expression over what is typically observed by random integration into a genome, for example, as compared to a pool of random integrants of a single copy of the same expression construct. Fold-expression enhancement observed employing the sequences of the invention is in comparison to an expression level of the same gene, measured under substantially the same conditions, in the absence of a sequence of the invention. As used herein, the phrase "expression-enhancing" is used interchangeably with "enhanced expression and stability" when referring to a region or sequence. An "enhanced expression and stability region," also referred to herein as an "EESYR," is a region or sequence that exhibits more efficient recombination, insert stability, and higher level expression than is typically observed by random integration into a genome.

Enhanced recombination efficiency includes an enhancement of the ability of a locus to recombine (for example, employing recombinase-recognition sites). Enhancement refers to an efficiency over random recombination, which is typically 0.1%. A preferred enhanced recombination efficiency is about 10-fold over random, or about 1%. Unless specified, the claimed invention is not limited to a specific recombination efficiency.

Where the phrase "exogenously added gene" or "exogenously added GOI" is employed with reference to a EESYR, the phrase refers to any gene not present within the EESYR as the EESYR is found in nature. For example, an "exogenously added gene" within a CHO EESYR (e.g., an EESYR comprising a sequence of SEQ ID NO:5), can be a hamster gene not found within the CHO EESYR in nature (i.e., a hamster gene from another locus in the hamster genome), a gene from any other species (e.g., a human gene), a chimeric gene (e.g., human/mouse), or any other gene not found in nature to exist within the CHO EESYR.

Percent identity, when describing an EESYR, is meant to include homologous sequences that display the recited identity along regions of contiguous homology, but the presence of gaps, deletions, or insertions that have no homolog in the compared sequence are not taken into account in calculating percent identity. In explaining the usage of "percent identity" in this context, the following sequence comparison (SEQ ID NO: 9-SEQ ID NO: 12) will be referred to:

| EESYR | 5595 | AGATTCTGTGGGCTCTGAGGCAACTTGACCTCAGCCAGATGGTATTTGAATAACCTGCTC | 5654 |
| Rat Ch3 | 5619 | AGATTCTGTGGGTTCTGAGACAACTTGACTTCAGCCAGATGGCATTTGAATAAC------ | 5672 |
| M Mus Ch2 | 6618 | AGATTCTGTGGGTTCTGAGACAACTTGACTTTAGCCAGATGGTATTTGAGTAATCTGGG- | 6676 |
| H. Sap. Ch20 | 6620 | AGATTCAGTGGGCTTTGGGACAGCTTGACTTCAACTAGATGGTATTTGAATAATCTGCT- | 6678 |
| | | **** *** * ** *  **** * * * **** ** * | | in which the "EESYR" 5595-5654 sequence is SEQ ID NO: 9, the "Rat Ch3" 5619-5672 sequence is SEQ ID NO: 10, the "M Mus Ch2" 6618-6676 sequence is SED ID NO: 11, and the "H. Sap. Ch20" sequence is SEQ ID NO: 12. As used herein, a "percent identity" determination between the "EESYR" sequence above (for a CHO cell EESYR or fragment thereof) with a rat homolog ("Rat Ch3") would not include a comparison of CHO sequences 5649 through 5654, since the rat homolog has no homologous sequence to compare in an alignment (i.e., the CHO EESYR has an insertion at that point, or the rat homolog has a gap or deletion, as the case may be). Thus, in the comparison above, the percent identity comparison would extend from the "AGATTC" at the 5' end to the "AATAAC" at the 3' end. In that event, the rat homolog differs only in that it has a "T" at CHO EESYR position 5607, an "A" at CHO EESYR position 5614, a "T" at CHO EESYR position 524, and a "C" at CHO EESYR position 5637. Since the comparison is over 54 contiguous bases in a 60 base pair stretch, with only four differences (which are not gaps, deletions, or insertions), there is over 90% identity between the two sequences (CHO and rat) from CHO EESYR position 5595 to CHO EESYR position 5654 (because "percent identity" does not include penalties for gaps, deletions, and insertions).

General Description

The invention is based at least in part on the discovery that there are sequences in a genome that exhibit more efficient recombination, insert stability, and higher level expression than other regions or sequences in the genome. The invention is also based at least in part on the finding that when such expression-enhancing sequences are identified, a suitable gene or construct can be exogenously added in or near the sequences and that the exogenously added gene can be advantageously expressed. Such sequences, termed enhanced expression and stability regions ("EESYRs"), can be engineered to include recombinase recognition sites for placement of genes of interest to create cell lines that are capable of expressing proteins of interest. EESYRs can also be included as in expression constructs such as, for example, expression vectors. Expression vectors comprising EESYRs can be used to express proteins transiently, or can be integrated into a genome by random or targeted recombination such as, for example, homologous recombination or recombination mediated by recombinases that recognize specific recombination sites (e.g., Cre-lox-mediated recombination). Expression vectors comprising EESYRs can also be used to assess efficacy of other DNA sequences, for example, cis-acting regulatory sequences.

The CHO EESYR described in detail herein was identified by random integration of DNA comprising lox sites into a CHO cell genome, followed by selection to identify sequences where expression was enhanced. Random integration and introduction of the lox site was achieved using a retroviral construct. Selection and screening were achieved using drug resistance markers and detectable labels (e.g., fluorescent proteins with FACS screening), employing recombination methods that used site-specific recombination (e.g., lox sites and Cre recombinase). Selection continued until at least a 1.5- to 2-fold enhanced expression over expression observed when randomly integrating an expression construct into the CHO cell genome. Following identification of the EESYR, recombinase recognition sites (in the example provided, lox sites) were maintained in the EESYR for introducing expression cassettes that comprise an expressible GOI, along with any other desirable elements such as, for example, promoters, enhancers, markers, operators, etc.

Figure 2:
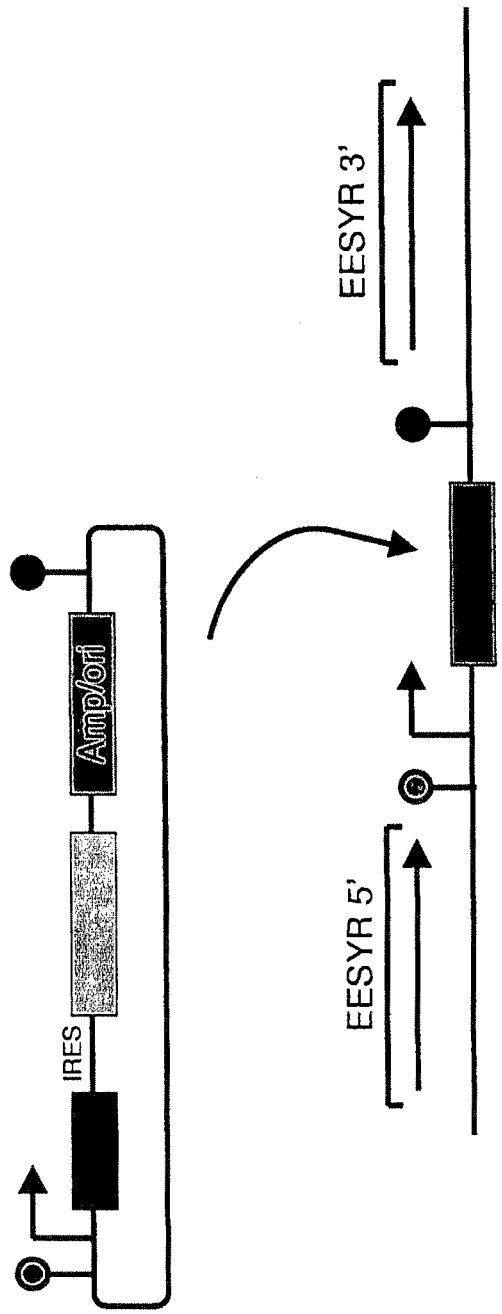
FIG. 2 illustrates a plasmid construct used to identify an EESYR.

An illustration of a plasmid construct used in identifying an EESYR disclosed in this application is shown in FIG. 2. The plasmid rescue construct comprises an expression cassette driven by an promoter, wherein the cassette is flanked on the 5' and 3' ends with recombinase recognition sites (represented by ball-and-stick in FIG. 2). Insertion within an EESYR locus is shown, wherein the insertion results in the plasmid rescue construct replacing an expression cassette that comprises a promoter and a marker, wherein the expression cassette within the EESYR locus is flanked on its 5' and 3' ends by recombinase recognition sites (see FIG. 2).

Compositions and methods are provided for stably integrating a nucleic acid sequence into a eukaryotic cell, wherein the nucleic acid sequence is capable of enhanced expression by virtue of being integrated in or near an EESYR. Cells are provided that contain a recombinase recognition sequence within or near an EESYR, convenient for inserting a GOI, in order to achieve expression of a protein of interest from the GOI. Compositions and methods are also provided for using EESYRs in connection with expression constructs, for example, expression vectors, and for adding an exogenous EESYR into a eukaryotic cell of interest.

Physical and Functional Characterization of an EESYR

The nucleic acid sequences referred to as EESYRs were empirically identified by sequences upstream and downstream of the integration site of a nucleic acid construct (comprising an expression cassette) of a cell line expressing a reporter protein at a high level. The EESYR nucleic acid sequences of the invention provide sequences with a new functionality associated with enhanced expression of a nucleic acid (for example, an exogenous nucleic acid comprising a GOI that appear to function differently from that previously described for cis-acting elements such as promoters, enhancers, locus control regions, scaffold attachment regions or matrix attachment regions. EESYRs do not appear to have any open reading frames (ORFs), making it unlikely that EESYRs encode novel trans-activator proteins. Transfection experiments demonstrated that EESYR sequences display some characteristics of cis-acting elements. EESYR activity is not detected in transient transfection assays; EESYR sequences also appear to be distinct from promoter and enhancer elements, which are detected with these methods.

Although EESYR sequences described in detail herein were isolated from the genome of two cell lines, EESYR sequences from these two cell lines are the same. EESYR activity was identified in a 6.472 kb fragment of CHO genomic DNA 5' with respect to a unique integration site of a retroviral vector comprising a DsRed reporter encoding sequence and in a 7.045 kb fragment of CHO genomic DNA 3' with respect to the integration site. Expression vectors comprising the isolated 6.472 kb region and the isolated 7.045 kb region and shorter fragments thereof were able to confer upon CHO cells transfected with them high levels of expression of recombinant proteins.

The invention encompasses expression vectors comprising reverse orientated EESYR fragments. Reverse orientated EESYR fragments were also capable of conferring upon CHO cells transfected with them high levels of expression of recombinant proteins.

Other combinations of the fragments described herein can also be developed. Examples of other combinations of the fragments described herein that can also be developed include sequences that include multiple copies of the EESYR disclosed herein, or sequences derived by combining the disclosed EESYR with other nucleotide sequences to achieve optimal combinations of regulatory elements. Such combinations can be contiguously linked or arranged to provide optimal spacing of the EESYR fragments (e.g., by the introduction of spacer nucleotides between the fragments). Regulatory elements can also be arranged to provide optimal spacing of an EESYR with respect to the regulatory elements.

The EESYR sequences disclosed herein were isolated from CHO cells. Homologous expression-enhancing elements are expected to exist in cells from other mammalian species (such as, for examples, humans; see FIG. 3) as well as in cell lines derived from other tissue types, and can be isolated by techniques that are well-known in the art, for example, by cross-species hybridization or PCR-based techniques. In addition, changes can be made in the nucleotide sequence set forth in SEQ ID NOs:1-6 by site-directed or random mutagenesis techniques that are well known in the art. The resulting EESYR variants can then be tested for EESYR activity as described herein. DNAs that are at least about 80% identical, preferably at least about 90% identical, more preferably at least about 95% identical, most preferably least about 99% identical in nucleotide sequence to SEQ ID NOs:1-6 or fragments thereof having EESYR activity are isolatable by routine experimentation, and are expected to exhibit EESYR activity. For fragments of EESYR, percent identity refers to that portion of the reference native sequence that is found in the EESYR fragment. Accordingly, homologs of EESYR and variants of EESYR are also encompassed by embodiments of the invention. FIGS. 3A and B show an alignment of mouse, human, and rat sequences with varying homology to a fragment of SEQ ID NO:5.

Cell populations expressing enhanced levels of a protein of interest can be developed using the methods provided herein. The absolute level of expression will vary with the specific protein, depending on how efficiently the protein is processed by the cell. Cell pools developed with EESYR are stable over time, and can be treated as stable cell lines for most purposes.

Cloning steps can be delayed until later in the process of development than is customary for recombinant proteins.

EESYRs and Expression-Enhancing Fragments Thereof

Figure 4:
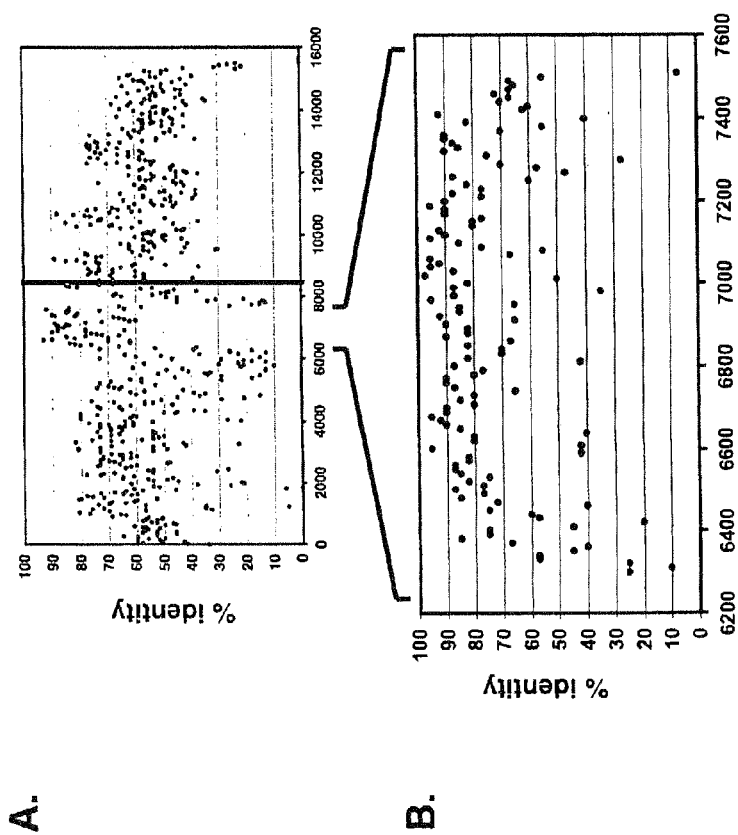
FIG. 4 shows an alignment of SEQ ID NO:5 with mouse, human, and rat sequences.

The EESYR genomic locus is conserved among human, mouse and rat genomes. FIG. 4 shows percent identity among EESYR sequences. EESYR sequences, homologous to the 13.515 kb of cloned CHO EESYR DNA of SEQ ID NO:5, were identified among the published human, rat and mouse genomes using BLAST. Sequences were aligned to determine the percent homology using MacVector (9.0). Twenty-five by increments of the alignment are graphed as the percent identity among CHO, human, mouse and rat EESYR sequences for each consecutive 25 bp segment. As shown in FIG. 4, the vertical line marks the location of site-specific recombination events to express recombinant protein genes of interest. Percent identity of EESYR sequences adjacent to a site-specific recombination location in an EESYR is shown in panel B of FIG. 4. Ten base pair increments of the aligned sequences corresponding to nt 5022-6110 of a CHO cell EESYR sequence (nucleotides 5022 through 6110 of SEQ ID NO:5) are graphed as the percent identity among CHO, human, mouse and rat EESYR sequences for each consecutive 10 bp segment. Sequences were aligned using MacVector™ 9.0. As shown in panel B, a significant identity of sequence is present in this fragment of the EESYR cloned from CHO cells. It should be noted that the comparison of FIG. 4 indicates a length of about 1400 bases, whereas the sequence of SEQ ID NO:5 contains 13,515 bases. The FIG. 4 bases appear to extend over a longer stretch due to the existence of gaps. Nucleotide spans recited are those corresponding to numbering in SEQ ID NO:5 unless otherwise indicated. The span of nucleotides from about 6200 to about 7600 as shown in FIG. 4B corresponds to nucleotides of SEQ ID NO:5 numbered about 5,200 to about 6,000.

Accordingly, the invention also includes an expression-enhancing fragment of a nucleotide sequence of SEQ ID NO:5, wherein the expression-enhancing fragment includes the nucleotide sequence indicated by positions about residues 5022 through about 6110 of SEQ ID NO:5, or about 5218 through about 6048 of SEQ ID NO:5; or about 6200 through about 7600, about 6500 to about 7400, or about 6400 to about 6500 shown in panel B of FIG. 4. The invention also encompasses an expression-enhancing fragment of a nucleotide sequence that is at least 80% identical, preferably at least 90% identical, more preferably at least 95% identical, most preferably at least 99% identical to the nucleotide sequence indicated by positions about 6200 through about 7600, or about 6500 through about 7400, or about 6400 through about 6500 shown in panel B of FIG. 4. The invention includes vectors comprising such a fragment, including for transient or stable transfection. The invention also includes a eukaryotic cell comprising such a fragment wherein the fragment is exogenous and is integrated into the cell genome, and cells comprising such a fragment having at least one recombinase recognition site that is within, immediately 5', or immediately 3' to the fragment.

In one embodiment, the expression-enhancing fragment of SEQ ID NO:5 is located at a position within SEQ ID NO:5 selected from nucleotides spanning positions numbered 10-13,515; 20-12,020; 1,020-11,020; 2,020-10,020; 3,020-9,020; 4,020-8,020; 5,020-7,020; 6,020-6,920; 6,120-6,820; 6,220-6,720; 6,320-6,620; 6,420-6,520; 6,460-6,500; 6,470-6,490; and 6,475-6,485.

Figure 5:
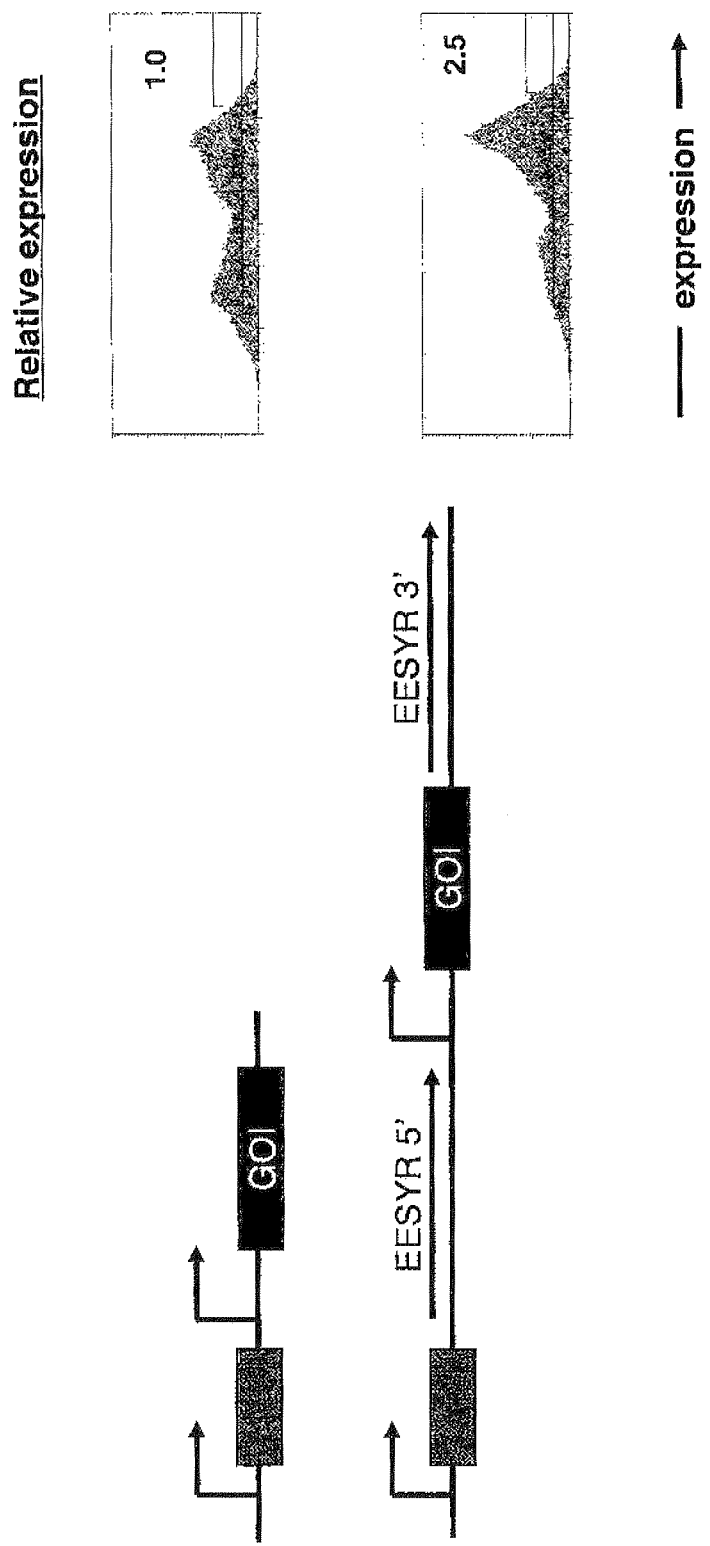
FIG. 5 illustrates that an EESYR, operably linked to a gene of interest (GOI), exhibits enhanced expression over a GOI that is not operably linked to an EESYR. For each plot, major ticks on the y-axis represent 0, 300, 600, 900, and 1200; major ticks on the x-axis represent $10^0$, $10^1$, $10^2$, $10^3$, and $10^4$.

In one embodiment, the EESYR is employed to enhance the expression of a GOI, as illustrated in FIG. 5. FIG. 5 shows a GOI operably linked with a promoter (with an upstream marker having its own promoter) integrated in a non-EESYR position in a CHO cell genome, and a FACS readout showing the distribution of expression in a stably transfected population of cells. In comparison, a GOI operably linked to a promoter integrated at an EESYR position in a CHO cell genome is shown, and a FACS readout showing the distribution of expression in a stably transfected population of cells is also shown. In this embodiment, the GOI expressed within the EESYR locus shows an enhanced expression of about two-fold in comparison to the GOI expressed at a non-EESYR locus.

In various embodiments, expression of a GOI can be enhanced by placing the GOI within an EESYR, 5' to an EESYR, or 3' to an EESYR. The precise distance between the GOI and the EESYR, where the GOI is either 5' or 3' to the EESYR, should be such that the EESYR is operably linked to the GOI. An EESYR is operably linked to the GOI where expression of the GOI—at the selected distance from the EESYR (in the 5' or 3' direction)—retains the ability to enhance expression of the GOI over, for example, expression typically observed due to a random integration event. In various embodiments, enhancement is at least about 1.5-fold to about 2-fold or more. Preferably, enhancement in expression as compared to a random integration, or random expression, is about 2-fold or more.

Figure 6:
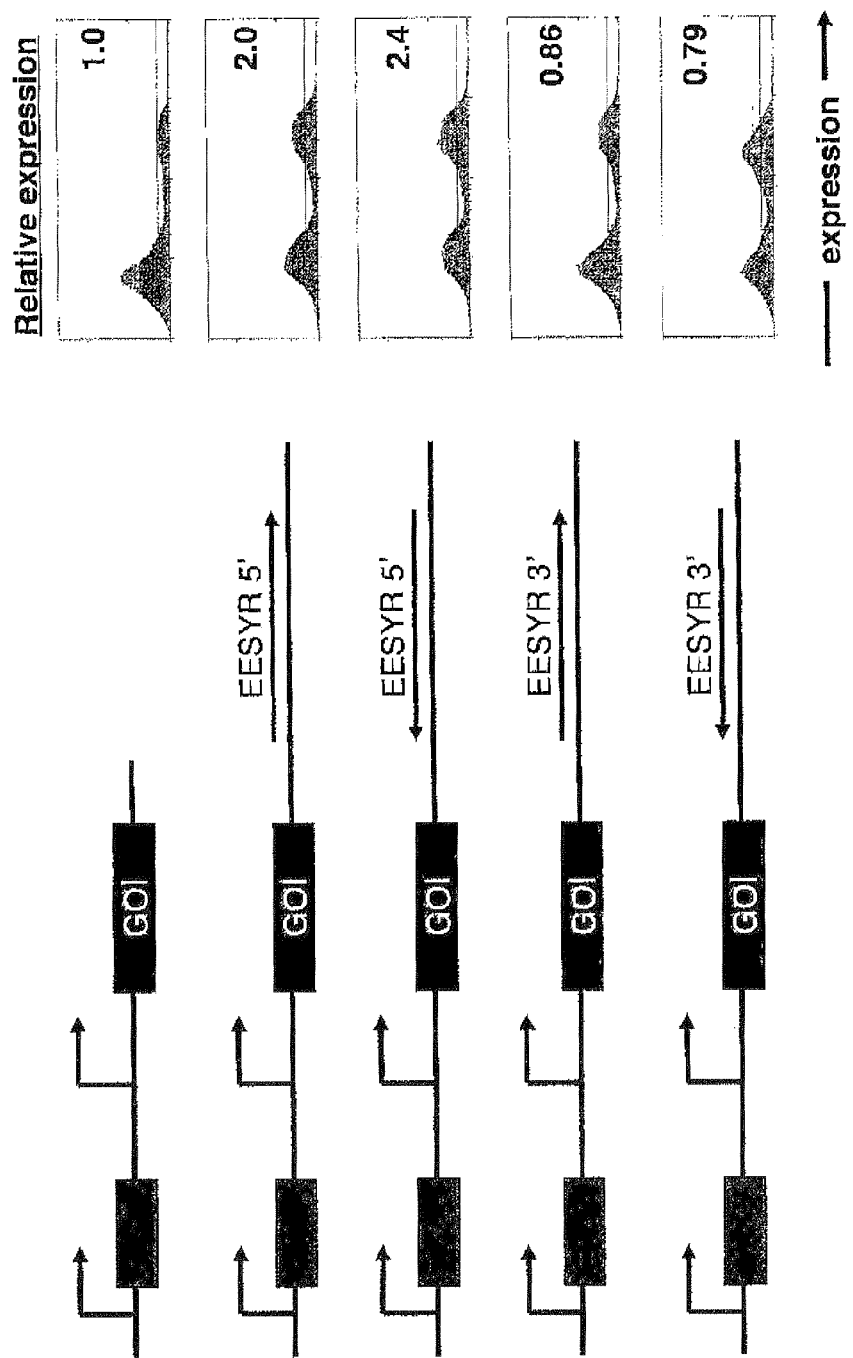
FIG. 6 shows EESYRs compared in their relative ability to enhance expression of an operably linked GOI. For each plot, y-axis major ticks represent Counts of 0, 500, 1,000, 1,500, and 2,000; x-axis major ticks represent FITC of $10^0$, $10^1$, $10^2$, $10^3$, and $10^4$.

FIG. 6 shows an embodiment wherein SEQ ID NO:1 ("EESYR 5'") and SEQ ID NO:2 ("EESYR 3'") are compared in their relative ability to enhance expression of an operably linked GOI, wherein the GOI is operably linked to a promoter as well (a marker and a promoter operably linked to the marker are shown 5' to the GOI promoter). Orientation of the EESYR is shown by the direction of the arrow beneath the term "EESYR." The constructs are randomly integrated into a CHO cell genome. Expression is relative to the randomly integrated construct that does not comprise any EESYR. FACS readouts showing relative expression are shown on the right. In FIG. 6, the first EESYR construct employs SEQ ID NO:1; the second EESYR construct employs SEQ ID NO:3; the third EESYR construct is SEQ ID NO:2; the fourth EESYR construct is SEQ ID NO:4. As shown in the figure, SEQ ID NO:3 displays a 2.4-fold enhancement in expression, and SEQ ID NO:1 displays a 2-fold enhancement of expression.

Figure 7:
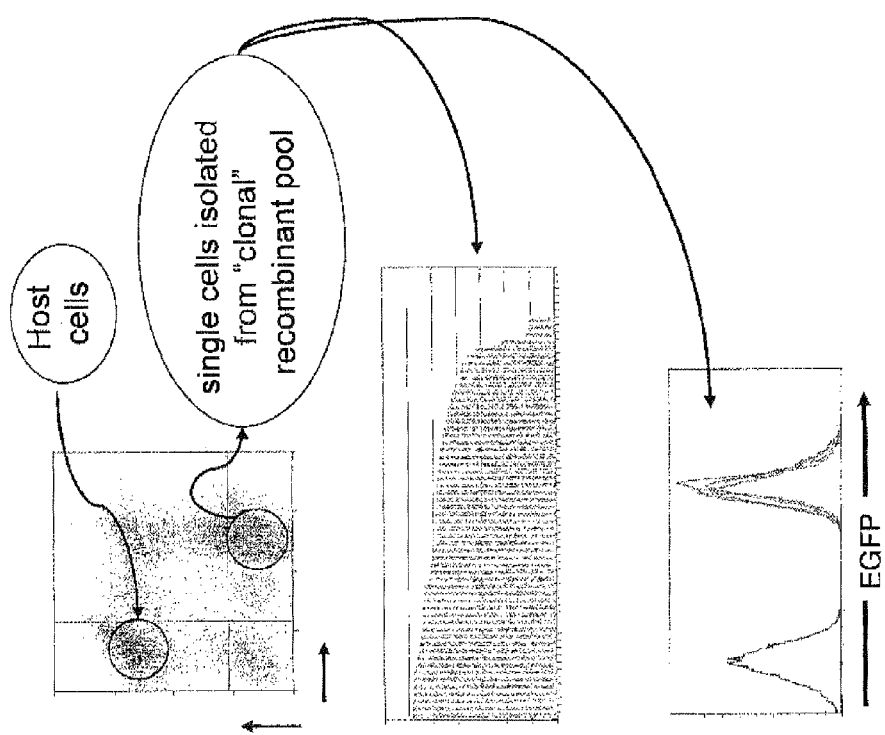
FIG. 7 illustrates clonal characteristics of cells with respect to EESYR functionality. For the top plot, major tick labels on both the y- and x-axes of the top plot represent $10^0$, $10^1$, $10^2$, $10^3$, and $10^4$; quadrant identifiers are R10 and R11 (top, left to right) and R12 and R13 (bottom, left to right). For the middle plot, which shows 96-well plate ELISA results of sorted single cells, the y-axis of the center plot represents Titer (μg/ml), with major tick labels of 0, 2, 4, 6, 8, 10, 12, and 14; whereas the x-axis represents Clone Number (in triplicate) from 1 to 63. For the bottom plot, which shows clone stability after three months without selection, y-axis major ticks represent increments of 100 from 0 to 1000. For the bottom plot, the left peak is for "Host," whereas the right peak is for "Recombinant clones."

EESYR recombinant cell pools display clonal characteristics. FIG. 7 illustrates clonal characteristics of EESYR recombinant pools. In the two-color FACS plot representing a dual parameter histogram of cells labeled with red or green markers (red cells are host CHO cells; green cells are recombinants expressing a GOI), EESYR recombinant pools show clustering in the plot that reflects substantially identical growth and expression, flow cytometry profile, and Southern analysis (not shown). A histogram of ELISAs of single cells demonstrate uniform expression in all clones. Clonal stability is also high after three months without selection.

Figure 8:
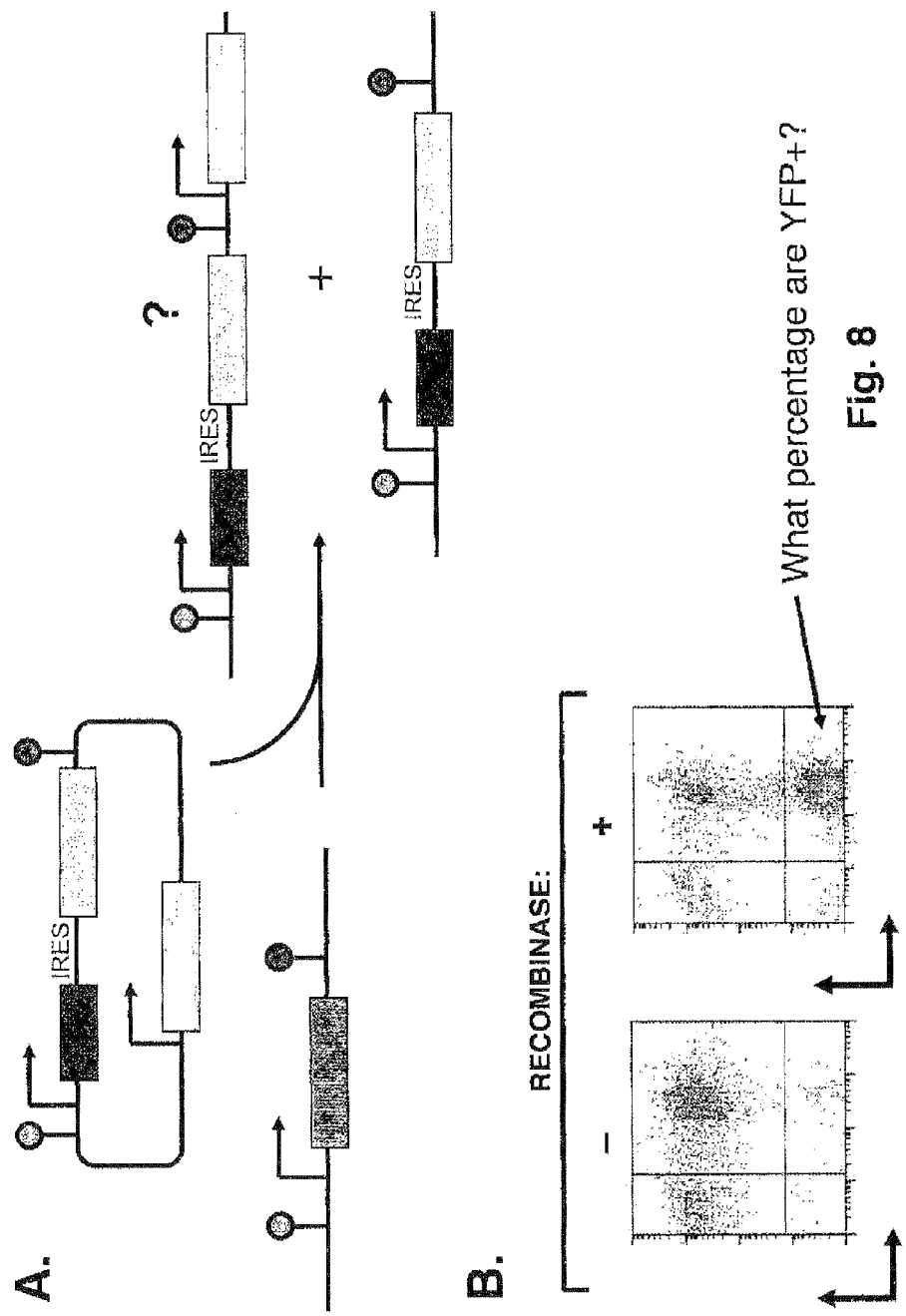
FIG. 8 illustrates that EESYR cells undergo specific and efficient recombination. In Panel B, y- and x-axes major ticks represent $10^0$, $10^1$, $10^2$, $10^3$, and $10^4$; for each plot, quadrants are (left to right, top) R2 and R3, and (left to right, bottom) R4 and R5.

EESYR recombinants undergo specific and efficient recombination, as shown in FIG. 8. Panel A shows two markers separated by an IRES and flanked by recombinase recognition sites, and a third marker not flanked by recombinase recognition sites as a random integration control. When recombined at an EESYR locus comprising a marker flanked by two recombinase recognition sites, recombination is specific. Panel B shows little random integration in the absence of recombinase, but efficient and site-specific integration in the presence of recombinase.

Figure 9:
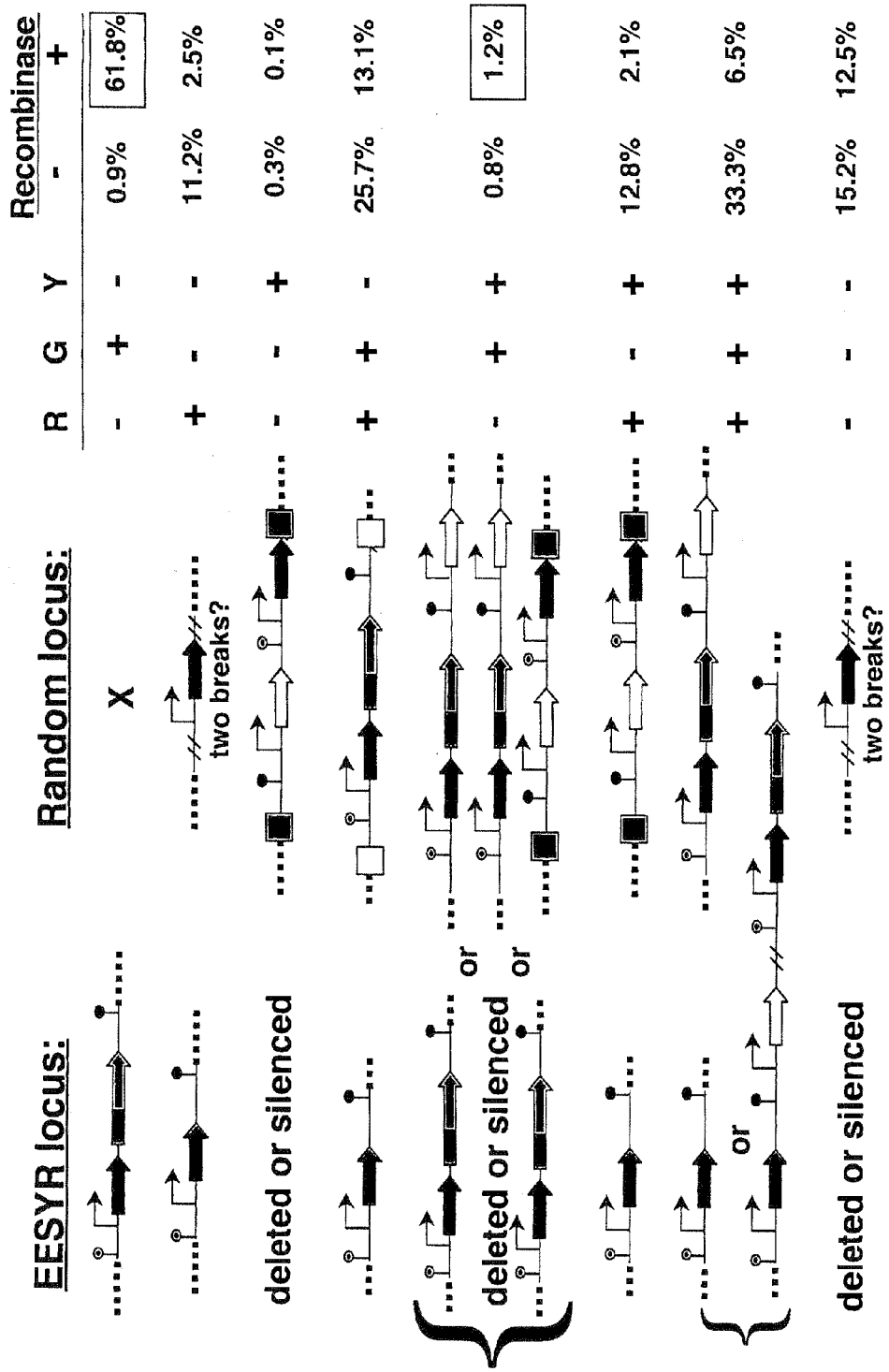
FIG. 9 illustrates the rarity of random integration events in EESYR cells.

Random integration using site specific recombination at an EESYR is rare (see FIG. 9). FIG. 9 shows that when random integration events are visualized, such events represent only a tiny fraction of integration events.

Figure 10:
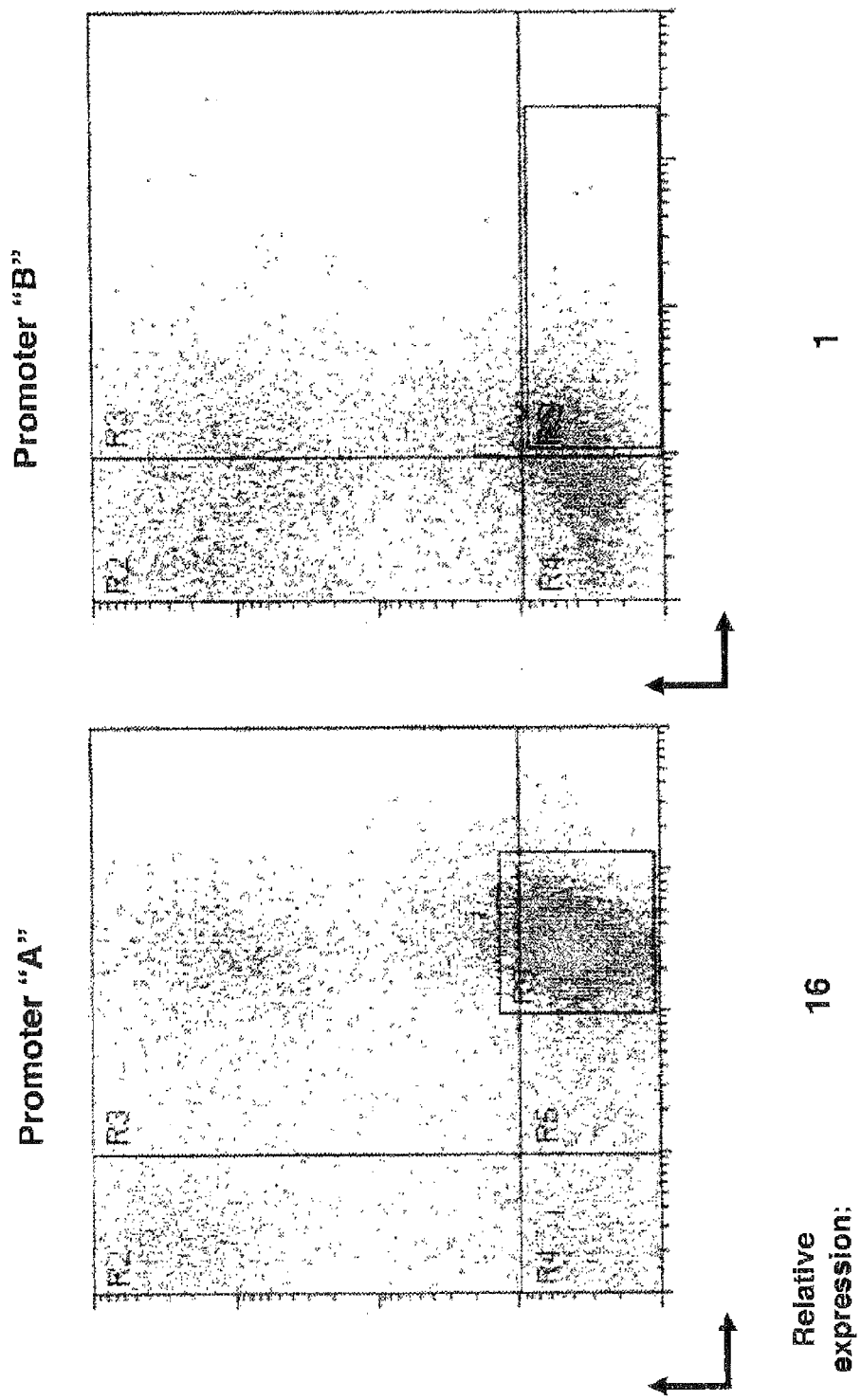
FIG. 10 illustrates testing of cis-acting elements employing EESYR sequences. Major ticks of the y- and x-axes major ticks represent $10^0$, $10^1$, $10^2$, $10^3$, and $10^4$.
Figure 11:
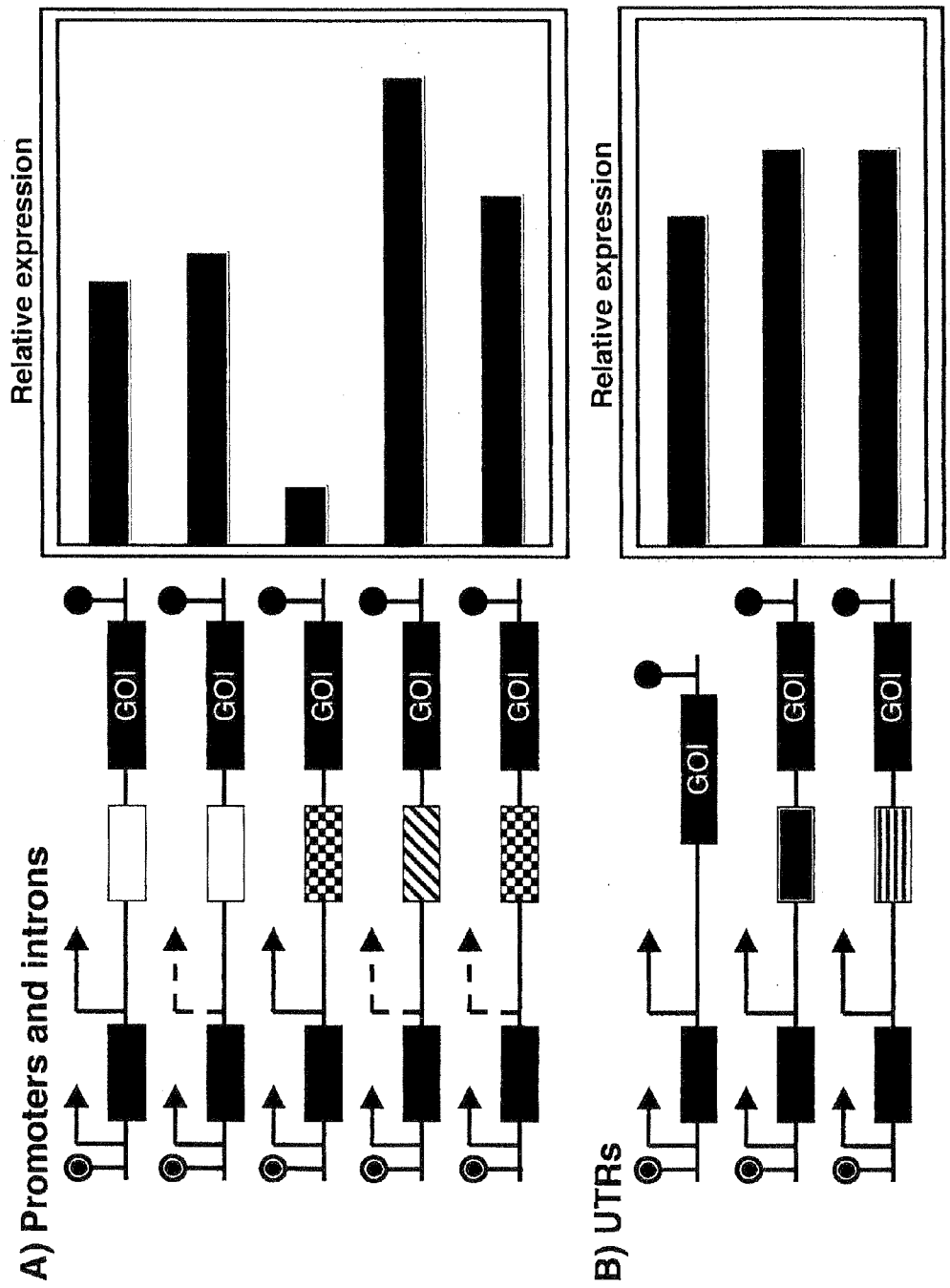
FIG. 11 illustrates testing promoters, introns, and UTRs using an EESYR system.

In another embodiment, EESYR cis-acting elements can be assessed using the methods and compositions of the invention. As shown in FIG. 10, EESYR recombinant cells, allows comparison of cis-acting elements equivalently. Because EESYR recombinants behave as a clonal population, differences in gene expression as the result of, for example, the presence or absence of suspected cis-acting elements, can be directly compared. Isogenic cell lines allow direct comparison of cis-acting elements. Using an EESYR system, cis-acting elements, such as, for example, promoters, introns, and UTRs, are preferably located between recombination sites. Expression optimization can also be achieved, including, for example, expression cassette orientation and codon optimization. By way of example, FIG. 11 shows cassettes flanked with recombination recognition sites that contain a promoter, a marker, various cis-elements (here, introns in panel A; UTRs in panel B), and a GOI were integrated at an EESYR (SEQ ID NO: 1 at the 5' end, SEQ ID NO:2 at the 3' end). Relative expression of the GOI is shown on the right.

Figure 12:
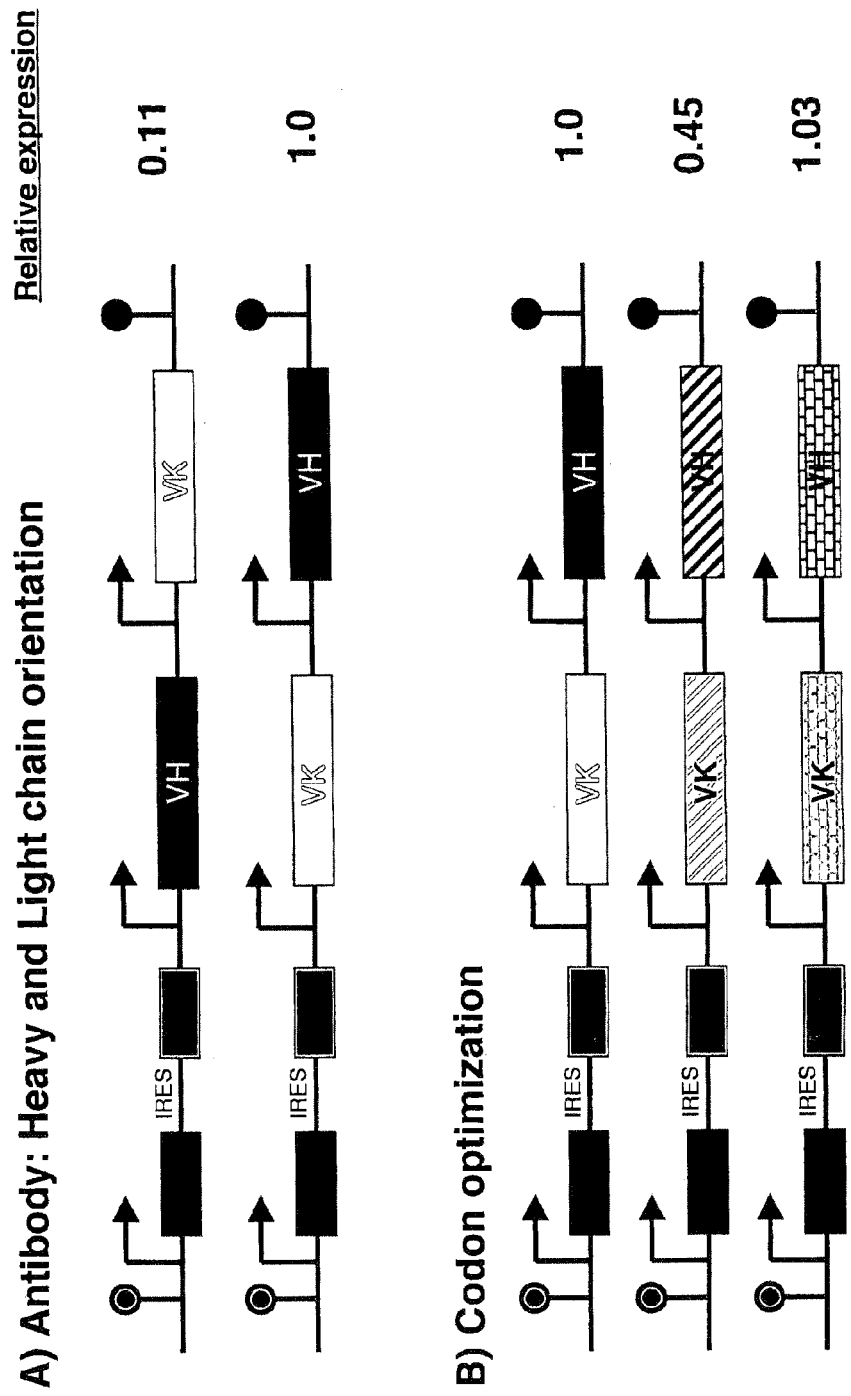
FIG. 12 illustrates optimizing protein expression using an EESYR system.

FIG. 12 shows an example of how protein optimization can be achieved using the methods and compositions of the invention. FIG. 12 confirms that optional placement of a cDNA for a light chain antibody gene is 5' to the cDNA for a heavy chain antibody gene.

Proteins of Interest

A nucleic acid sequence encoding a protein of interest can be conveniently integrated into a cell comprising an EESYR having a recombinase recognition site through, for example, a recombinase-mediated cassette exchange (RMCE) process. Any protein of interest suitable for expression in eukaryotic cells can be used. For example, the protein of interest can be an antibody or fragment thereof, a chimeric antibody or fragment thereof, an ScFv or fragment thereof, an Fc-tagged protein or fragment thereof, a growth factor or a fragment thereof, a cytokine or a fragment thereof, or an extracellular domain of a cell surface receptor or fragment thereof.

Nucleic Acid Constructs

Recombinant expression vectors can comprise synthetic or cDNA-derived DNA fragments encoding a protein, operably linked to a suitable transcriptional and/or translational regulatory element derived from mammalian, viral or insect genes. Such regulatory elements include transcriptional promoters, enhancers, sequences encoding suitable mRNA ribosomal binding sites, and sequences that control the termination of transcription and translation, as described in detail below. Mammalian expression vectors can also comprise nontranscribed elements such as an origin of replication, other 5' or 3' flanking nontranscribed sequences, and 5' or 3' nontranslated sequences such as splice donor and acceptor sites. A selectable marker gene to facilitate recognition of transfectants may also be incorporated.

Transcriptional and translational control sequences in expression vectors useful for transfecting vertebrate cells may be provided by viral sources. For example, commonly used promoters and enhancers are derived from viruses such as polyoma, adenovirus 2, simian virus 40 (SV40), and human cytomegalovirus (CMV). Viral genomic promoters, control and/or signal sequences may be utilized to drive expression, provided such control sequences are compatible with the host cell chosen. Non-viral cellular promoters can also be used (e.g., the β-globin and the EF-1α promoters), depending on the cell type in which the recombinant protein is to be expressed.

DNA sequences derived from the SV40 viral genome, for example, the SV40 origin, early and late promoter, enhancer, splice, and polyadenylation sites may be used to provide other genetic elements useful for expression of a heterologous DNA sequence. Early and late promoters are particularly useful because both are obtained easily from the SV40 virus as a fragment that also comprises the SV40 viral origin of replication (Fiers et al., Nature 273:113, 1978). Smaller or larger SV40 fragments may also be used. Typically, the approximately 250 bp sequence extending from the Hind III site toward the BglI site located in the SV40 origin of replication is included.

Bicistronic expression vectors used for the expression of multiple transcripts have been described previously (Kim S. K. and Wold B. J., Cell 42:129, 1985; Kaufman et al. 1991, supra) and can be used in combination with an EESYR sequence of the invention. Other types of expression vectors will also be useful, for example, those described in U.S. Pat. No. 4,634,665 (Axel et al.) and U.S. Pat. No. 4,656,134 (Ringold et al.).

Host Cells and Transfection

The eukaryotic host cells used in the methods of the invention are mammalian host cells, including, for example, CHO cells and mouse cells. In a preferred embodiment, the invention provides a nucleic acid sequence that encodes an EESYR sequence from CHO cell. An integration site, for example, a recombinase recognition site, can be placed within an EESYR, or 5' or 3' to the EESYR sequence. One example of a suitable integration site is a lox p site. Another example of a suitable integration site is two recombinase recognition sites, for example, a lox p site and a lox 5511 site. In one embodiment, the EESYR sequence is located on chromosome 6 of a CHO cell genome. In specific embodiments, the EESYR sequence is located within a sequence selected from the group consisting of nucleic acids comprising nucleotides 1-6473 and 4607-6473 of SEQ ID NO: 1; and 1-7045, 1-3115, 1-2245, 1-935, and 1-465 of SEQ ID NO:2.

The invention includes a mammalian host cell transfected with an expression vector of the invention. While any mammalian cell may be used, the host cell is preferably a CHO cell.

Transfected host cells include cells that have been transfected with expression vectors that comprise a sequence encoding a protein or polypeptide. Expressed proteins will preferably be secreted into the culture medium, depending on the nucleic acid sequence selected, but may be retained in the cell or deposited in the cell membrane. Various mammalian cell culture systems can be employed to express recombinant proteins. Examples of suitable mammalian host cell lines include the COS-7 lines of monkey kidney cells, described by Gluzman (1981) Cell 23:175, and other cell lines capable of expressing an appropriate vector including, for example, CV-1/EBNA (ATCC CRL 10478), L cells, C127, 3T3, CHO, HeLa and BHK cell lines. Other cell lines developed for specific selection or amplification schemes will also be useful with the methods and compositions provided herein. A preferred cell line is the CHO cell line designated K1. In order to achieve the goal of high volume production of recombinant proteins, the host cell line should be pre-adapted to bioreactor medium in the appropriate case.

Several transfection protocols are known in the art, and are reviewed in Kaufman (1988) Meth. Enzymology 185:537. The transfection protocol chosen will depend on the host cell type and the nature of the GOI, and can be chosen based upon routine experimentation. The basic requirements of any such protocol are first to introduce DNA encoding the protein of interest into a suitable host cell, and then to identify and isolate host cells which have incorporated the heterologous DNA in a relatively stable, expressible manner.

One commonly used method of introducing heterologous DNA into a cell is calcium phosphate precipitation, for example, as described by Wigler et al. (Proc. Natl. Acad. Sci. USA 77:3567, 1980). DNA introduced into a host cell by this method frequently undergoes rearrangement, making this procedure useful for cotransfection of independent genes.

Polyethylene-induced fusion of bacterial protoplasts with mammalian cells (Schaffner et al., (1980) Proc. Natl. Acad. Sci. USA 77:2163) is another useful method of introducing heterologous DNA. Protoplast fusion protocols frequently yield multiple copies of the plasmid DNA integrated into the mammalian host cell genome, and this technique requires the selection and amplification marker to be on the same plasmid as the GOI.

Electroporation can also be used to introduce DNA directly into the cytoplasm of a host cell, for example, as described by Potter et al. (Proc. Natl. Acad. Sci. USA 81:7161, 1988) or Shigekawa et al. (BioTechniques 6:742, 1988). Unlike protoplast fusion, electroporation does not require the selection marker and the GOI to be on the same plasmid.

More recently, several reagents useful for introducing heterologous DNA into a mammalian cell have been described. These include Lipofectin™ Reagent and Lipofectamine™ Reagent (Gibco BRL, Gaithersburg, Md.). Both of these reagents are commercially available reagents used to form lipid-nucleic acid complexes (or liposomes) which, when applied to cultured cells, facilitate uptake of the nucleic acid into the cells.

A method for amplifying the GOI is also desirable for expression of the recombinant protein, and typically involves the use of a selection marker (reviewed in Kaufman supra). Resistance to cytotoxic drugs is the characteristic most frequently used as a selection marker, and can be the result of either a dominant trait (e.g., can be used independent of host cell type) or a recessive trait (e.g., useful in particular host cell types that are deficient in whatever activity is being selected for). Several amplifiable markers are suitable for use in the expression vectors of the invention (e.g., as described in Maniatis, Molecular Biology: A Laboratory Manual, Cold Spring Harbor Laboratory, NY, 1989; pgs 16.9-16.14).

Useful selectable markers for gene amplification in drug-resistant mammalian cells are shown in Table 1 of Kaufman, R. J., supra, and include DHFR-MTX resistance, P-glycoprotein and multiple drug resistance (MDR)-various lipophilic cytotoxic agents (e.g., adriamycin, colchicine, vincristine), and adenosine deaminase (ADA)-Xyl-A or adenosine and 2'-deoxycoformycin.

Other dominant selectable markers include microbially derived antibiotic resistance genes, for example neomycin, kanamycin or hygromycin resistance. However, these selection markers have not been shown to be amplifiable (Kaufman, R. J., supra). Several suitable selection systems exist for mammalian hosts (Maniatis supra, pgs 16.9-16.15). Co-transfection protocols employing two dominant selectable markers have also been described (Okayama and Berg, Mol. Cell Biol 5:1136, 1985).

Useful regulatory elements, described previously or known in the art, can also be included in the nucleic acid constructs used to transfect mammalian cells. The transfection protocol chosen and the elements selected for use therein will depend on the type of host cell used. Those of skill in the art are aware of numerous different protocols and host cells, and can select an appropriate system for expression of a desired protein, based on the requirements of the cell culture system used.

Other features of the invention will become apparent in the course of the following descriptions of exemplary embodiments which are given for illustration of the invention and are not intended to be limiting thereof.

EXAMPLES

The following examples are put forth so as to provide those of ordinary skill in the art how to make and use the methods and compositions described herein, and are not intended to limit the scope of what the inventors regard as their invention. Efforts have been made to ensure accuracy with respect to numbers used (e.g., amount, temperature, etc.) but some experimental error and deviation should be accounted for. Unless indicated otherwise, parts are parts by weight, molecular weight is average molecular weight, temperature is in degrees Centigrade, and pressure is at or near atmospheric.

Example 1

Generation of RGC9 and RGC16 Cell Lines

CHO K1 cells ($1 \times 10^7$) were infected with pantropic retrovirus produced with plasmid pTE252 (FIG. 1), having a lox p site in it, at an MOI of less than 1 to generate a stable pool of cells with mostly one retroviral insertion per cell. Cells in the stable pool that expressed a marker protein at a high level were selected and expanded. Selection rounds were conducted to identify cell populations capable of enhanced expression. Thirty-six clones were isolated and expanded into 36 cell lines. Clones exhibiting the highest recombination efficiency were identified and cloned, wherein the clones each contained at least one recombinase recognition site in an enhanced expression locus. Eight cell populations with the best recombination efficiency were selected, and reassessed for enhanced protein expression. Two cell populations were selected and designated RGC9 and RGC16. Southern blot analysis of the cell populations from the original 36 cell lines that corresponded to these two cell lines showed that a single copy of a reporter construct was integrated into the CHO cell genome at the same locus in the case of both cell populations, and the location of integration was determined to be at the triplet "act" at nucleotide position 6,471 to 6,473 of SEQ ID NO:5. At least one of these two cell lines were employed in experiments described below.

Example 2

Expression of FcFP1 Protein in Serum-Free Production Medium

RGC38 cells were derived from RGC9 cells and were adapted to grow in suspension in a serum-free production medium. RGC38 cells were used as host cells for the expression of FcFP1 protein (Fc fusion protein-1). RGC38 cells were transfected in a ten-centimeter plate with a FcFP1 expression vector, pTE851 and a Cre plasmid, pRG858. The FcFP1 plasmid has, in 5' to 3' direction, a LoxP site, a SV40 late promoter, a hygromycin resistant gene, an IRES, an eGFP, a CMV MIE promoter, a gene encoding a FcFP1 protein, and a Lox511 site. Cells were cultured in F12 medium with 400 µg/ml hygromycin for two weeks after transfection. Cells expressing eGFP but not DsRed were isolated using flow cytometry and designated as RS421-1. Isolated cells were essentially isogenic, though derived from different founder cells. RS421-1 cells were expanded in suspension cultures in serum-free production medium. FcP1 protein in conditioned medium of 3-day old cultures was examined in SDS-PAGE with Coomassie blue staining. FcF1 protein in the conditioned medium was abundant and could be seen without purification.

Example 3

Regulated Expression of FcFP1 Protein in Serum-Free Production Medium

RGC49 cells were derived from RGC16, were adapted to grow in serum-free production medium, and contained a stably integrated tetR-YFP expression plasmid, pcDNA6/TR. The tetR protein allows regulation of transcription from promoters that comprise a tet operator sequence by tetracycline or doxycycline. RGC49 cells were co-transfected with pTE851 and pRG858. The transfected cells were selected with 400 μg/ml hygromycin for two weeks. Cells expressing eGFP but not YFP were isolated using flow cytometry and designated as RS569-1. RS569-1 cells were expanded in suspension cultures in serum-free production medium in the presence or absence of doxycycline. FcP1 protein in conditioned medium of 3-day old cultures was examined by SDS-PAGE and Coomassie blue staining. The RS569-1 cells expressed FcFP1 protein similarly to RS421-1 upon in the presence of 1 μg/ml doxycycline in the culture medium. Very little FcFP1 protein was detected from the RS569-1 cells in the absence of doxycycline.

Example 4

Dual Lox Cell Line Construction

RGC23 cells were derived from RGC16, were adapted to grow in Sigma CHO SSM serum-free medium (Saint Louis, Mo.), and carried DsRed. RGC23 cells were transfected with a Cre plasmid, pRG858 and a eGFP and FcFP2 protein expression vector, pTE357. The FcFP2 vector has, in 5' to 3' direction, a LoxP site, a SV40 late promoter, a hygromycin resistant gene, a CMV MIE promoter, a gene encoding FcFP2 protein, an IRES, an eGFP, and a Lox511 site. Cells expressing both DsRed and eGFP were collected and a single cell was isolated. The isolated cell was expanded in culture, and the resulting cell line was designated RS398-2-6. RS398-2-6 was then transfected with pRG858 (Cre plasmid) and pRG1231, a eCFP expression plasmid. pRG1231 has, in 5' to 3' direction, a LoxP site, a CMV MIE promoter, a puromycin resistant gene, an IRES, an eCFP, and a Lox511 site. Cells expressing DsRed and eCFP but not eGFP were isolated by flow cytometry as a pool and designated as RS630.

Example 5

Antibody Heavy Chain and Light Chain Expression Using a Dual Lox Cell Line

RS630 cells were transfected with pTE828, a 15G1 antibody heavy chain and eGFP expression vector, pTE829, a 15G1 antibody light chain and eYFP expression vector, and pRG858. pTE828 has, in 5' to 3' direction, a LoxP site, a SV40 late promoter, a hygromycin resistant gene, an IRES, an eGFP, a CMV MIE promoter, the heavy chain gene of 15G1 antibody, and a Lox511 site. pTE829 has, in 5' to 3' direction, a LoxP site, a SV40 late promoter, a neomycin resistant gene, an IRES, an eYFP, a CMV MIE promoter, the light chain gene of 15G1 antibody, and a Lox511 site. The transfected cultures were selected with hygromycin and G418 at 400 μg/ml each for two weeks. Cells expressed both YFP and eGFP but neither dsRed nor eCFP were isolated by flow cytometry. The isolated cells were expanded in suspension culture in serum-free production medium and were designated as RS631 cells. Aliquots of conditioned medium from 3-day old culture were analyzed by SDS-PAGE. The antibody products from RS631 cells were readily detected by Coomassie blue staining.

Example 6

Use of a Third Lox Site (Lox2272) at EESYR to Create Dual Expression Cassette Cells from any cell line carrying a DsRED gene flanked by a LoxP site and a Lox511 site at EESYR locus are transfected with pRG858 and a vector comprising, in 5' to 3' direction, a LoxP site, a first promoter, a YFP, a Lox2272 site, a second promoter, an eGFP, and a Lox511. Cells expressing eGFP and YFP, but not DsRed are isolated. Isolated cells are then transfected with pRG858, pRG1167 (a vector that has, in 5' to 3' direction, a LoxP site, a SV40 late promoter, a hygromycin resistant gene, a CMV MIE promoter, a DsRed and a Lox2272 site) or pRG1234 (a vector that has, in 5' to 3' direction, a Lox2272 site, a SV40 late promoter, a hygromycin resistant gene, a CMV MIE promoter, a DsRed and a Lox511 site). Cells capable of expressing either DsRED and eGFP but not YFP, or DsRED and YFP but not eGFP, are isolated.

Example 7

Antibody Expression from RGC38 Host Cells

RGC38 cells were transfected with pTE963 and pRG858. pTE963 has, in 5' to 3' direction, a LoxP site, a SV40 late promoter, a hygromycin resistant gene, an IRES, an eGFP, a CMV MIE promoter, the light chain gene of 15G1 antibody, a CMV MIE promoter, the heavy chain gene of 15G1 antibody, and a Lox511 site. The transfected cultures were selected with hygromycin at 400 μg/ml each for two weeks. Cells that expressed eGFP but not dsRed were isolated by flow cytometry. The isolated cells were expanded in suspension in serum-free production medium and were named as RS533 cells. For the production of 15G1 antibodies, RS533 cells were cultured in a bioreactor for 10 days. Aliquots of spent medium from day six to day ten were collected and their protein composition was analyzed by SDS-PAGE. The heavy chain and light chain peptide of the 15G1 antibody in the reactor spent medium were readily detected by Coomassie blue staining.

Example 8

Rescuing and Subcloning EESYR Sequences

A CHO cell line (designated RGC21) expressing high levels of a reporter gene, DsRed, was selected for isolation of EESYR sequences, since Southern blot analysis indicated that the high expression of DsRed expression observed for this cell line is driven by a single integration of an expression cassette encoding DsRed. Genomic sequences 5' to the expression cassette were rescued by transfecting RGC21 cells with linearized pTE494 plasmids, a vector that has, in 5' to 3' direction, a LoxP site, an ampicillin resistance gene, a bacterial origin or replication, a CMV MIE promoter, a neomycin phosphotransferase gene, an IRES, an eGFP and a Lox511 site. Cells expressing eGFP but not DsRed were isolated by flow cytometry as a pool. Genomic DNA was isolated, digested with XbaI restriction endonuclease, and self ligated to create pRG1106. Genomic sequences 3' to the expression cassette were rescued by transfecting RGC21 cells with circular pTE495 plasmids, a vector that has, in 5' to 3' direction, a LoxP site, a CMV MIE promoter, a neomycin phosphotransferase gene, an IRES, an eGFP, a bacterial origin or replication, an ampicillin resistance gene, and a Lox511 site. Cells expressing eGFP but not DsRed were isolated by flow cytometry as a pool. Genomic DNA was isolated, digested with MfeI restriction endonuclease, and self ligated to create pRG1099.

Example 9

Plasmid Construction for EESYR Analysis

EESYR sequences were excised from either pRG1106 or pRG1099 as AgeI fragments and inserted into the AgeI and NgoMIV sites of pTE575, a plasmid expressing FCFP2, to yield plasmid pTE809. The pTE575 plasmid has, in 5' to 3' direction, a SV40 late promoter, a hygromycin resistant gene, a CMV MIE promoter, and a gene encoding FCFP2 protein. In stably transfected CHO cells, pTE809 and pTE575 yielded 97.22% and 38.57% of cells expressing detectable levels of FCFP2 protein, respectively. The mean fluorescence of FcFP2 detected by an FITC conjugated antibody was 482.54 and 279.75 for cultures transfected with pTE809 and pTE575, respectively. Thus, the inclusion of EESYR in expression vectors increased the expression of FCFP2 protein in stable transfection.

The present invention may be embodied in other specific embodiments without departing from the spirit or essence thereof.

We claim:

1. An isolated cell comprising an expression-enhancing sequence selected from the group consisting of SEQ ID NOs: 1-4, a gene of interest (GOI) operably linked to the expression-enhancing sequence, and at least one recombinase recognition site immediately adjacent to the GOI.

2. The isolated cell of claim 1, wherein the GOI encodes a protein selected from an immunoglobulin or an antigen-binding fragment thereof, and a receptor or ligand-binding fragment thereof.

3. The isolated cell of claim 2, wherein the immunoglobulin is selected from an antibody light chain or antigen-binding fragment thereof, an antibody heavy chain or antigen-binding fragment thereof, or an Fc fusion protein.

4. The isolated cell of claim 1, wherein the at least one recombinase recognition site is selected from the group consisting of a LoxP site, a Lox511 site, a Lox2272, and a Frt site.

5. The isolated cell of claim 1, wherein the GOI is immediately adjacent and 5' of the recombinase recognition site, and further comprising a second recombinase recognition site immediately adjacent and 3' of the GOI.

6. The isolated cell of claim 5, further comprising a second GOI immediately adjacent and 3' of the second recombinase recognition site.

7. The isolated cell of claim 6, further comprising a third recombinase recognition site immediately adjacent and 3' of the second GOI.

8. The isolated cell of claim 7, further comprising at least one marker gene between the second recombinase recognition site and the second GOI.

9. The isolated cell of claim 8, wherein the at least one marker gene is selected from the group
consisting of a drug resistance gene and an expression reporter gene.

10. The isolated cell of claim 9, further comprising a promoter operably linked to the first GOI and a promoter operably linked to the second GOI.

11. The isolated cell of claim 10, wherein the second and the third recombinase recognition sites are in an orientation opposite to the first recombinase recognition site.

12. The isolated cell of claim 11, wherein the first, second, and third recombinase recognition sites are different.

13. The isolated cell of claim 12, wherein the promoters are eukaryotic promoters, and the eukaryotic promoters are operably linked to a prokaryotic operator.

14. An isolated cell comprising an expression-enhancing sequence selected from the group consisting of SEQ ID NOs: 1-4, and at least one exogenous gene of interest (GOI) operably linked to the expression-enhancing sequence.

15. The isolated cell of claim 14, wherein the expression-enhancing sequence is selected from the group consisting of SEQ ID NO: 1, 2, 3, 4, and a combination thereof; and wherein the cell is a CHO cell, the at least one exogenous GOI is a human gene, and the human gene is operably linked to an exogenous promoter.

16. The isolated cell of claim 15, further comprising a second GOI 3' of the first GOI, and the second GOI is operably linked to an exogenous promoter.

17. The isolated cell of claim 16, wherein the first GOI encodes a light chain of an antibody and the second GOI encodes a heavy chain of an antibody.

18. The isolated cell of claim 17, further comprising a first recombinase site 5' of the gene encoding a light chain of an antibody, and a second recombinase site immediately adjacent and 3' of the gene encoding a heavy chain of an antibody.

19. The isolated cell of claim 18, wherein the first and second recombinase recognition sites are different, and the first and second recombinase recognition sites are selected from the group consisting of a LoxP site, a Lox511 site, a Lox2272, and a Frt site.

20. A method for making a protein of interest, comprising:
(a) providing a recombinant host cell that comprises an expression-enhancing sequence selected from a sequence of SEQ ID NO:1-4 and at least one recombinase recognition site within or immediately adjacent to the expression-enhancing sequence; (b) introducing into the host cell a nucleic acid construct within the expression-enhancing sequence comprising a GOI that encodes for a protein of interest;
(c) culturing the host cell of under conditions that allow expression of the GOI; and,
(d) recovering the protein of interest.

21. The method of claim 20, wherein the GOI is operably linked to a promoter.

22. The method of claim 20, wherein the cell is a CHO cell, the expression enhancing sequence is SEQ ID NO:1, and the GOI encodes for a protein of interest comprising an immunoglobulin or an antigen-binding fragment thereof.

23. The method of claim 20, wherein the cell is a CHO cell, the expression enhancing sequence is SEQ ID NO:1, and the GOI encodes for a protein of interest comprising a receptor or a ligand-binding fragment thereof.

24. The method of claim 20, wherein the GOI is immediately adjacent and 5' of the recombinase recognition site, and further comprising a second recombinase recognition site immediately adjacent and 3' of the GOI.

25. The method of claim 24, further comprising a second GOI immediately adjacent and 3' of the second recombinase recognition site.

26. The method of claim 25, further comprising a third recombinase recognition site immediately adjacent and 3' of the second GOI.

27. The method of claim 26, wherein the second and the third recombinase recognition sites are in an orientation opposite to the first recombinase recognition site.

28. The method of claim 27, wherein the first, second, and third recombinase recognition sites are different.

29. The method of claim 28, wherein the second and the third recombinase recognition sites are in an orientation opposite to the first recombinase recognition site.

30. The method of claim 29, wherein the recombinase recognition site is selected from the group consisting of a loxp site, a lox 511 site, a lox 2272 site, and a frt site.

31. The method of claim 26, wherein the second GOI is introduced in to the cell on a second nucleic acid construct.

32. The method of claim 26 or 31, wherein the first GOI and the second GOI encode an antibody light chain, or fragment thereof, or an antibody heavy chain, or fragment thereof.

* * * * *

```
SEQUENCE LISTING

<160> NUMBER OF SEQ ID NOS: 20

<210> SEQ ID NO 1
<211> LENGTH: 6473
<212> TYPE: DNA
<213> ORGANISM: Cricetulus griseus

<400> SEQUENCE: 1
tctagaaaca aaaccaaaaa tattaagtca ggcttggctt caggtgctgg ggtggagtgc      60
tgacaaaaat acacaaattc ctggctttct aaggcttttt cggggattca ggtattgggt     120
gatggtagaa taaaaatctg aaacataggt gatgtatctg ccatactgca tgggtgtgta     180
tgtgtgtgta tgtgtgtctg tgtgtgtgcc cagacagaaa taccatgaag gaaaaaaaca     240
cttcaaagac aggagagaag agtgacctgg gaaggactcc ccaatgagat gagaactgag     300
cacatgccag aggaggtgag gactgaacca ttcaacacaa gtggtgaata gtcctgcaga     360
cacagagagg gccagaagca ctcagaactc caggggtca ggagtggttc tctggaggct     420
tctgcccttg gaggttcctg aggaggaggc ttccatattg aaaatgtagt tagtggccgt     480
ttccattagt acagtgacta gagagagctg agggaccact ggactgaggc ctagatgctc     540
agtcagatgg ccatgaaagc ctagacaagc acttccgggt ggaaaggaaa cagcaggtgt     600
gaggggtcag gggcaagtta gtgggagagg tcttccagat gaagtagcag gaacggagac     660
gcactggatg gccccacttg tcaaccagca aaagcttgga tcttgttcta agaggccagg     720
gacatgacaa gggtgatctc ggttttaaa aggctttgtg ttacctaatc acttctatta     780
gtcagatact ttgtaacaca aatgagtact tggcctgtat tttagaaact tctgggatcc     840
tgaaaaaaca caatgacatt ctggctgcaa cacctggaga ctcccagcca ggccctggac     900
ccgggtccat tcatgcaaat actcagggac agattcttca ctaggtactg atgagctgtc     960
ttggatgcaa atgtggcctc ttcattttac tacaagtcac catgagtcag gaggtgctgt    1020
ttgcacagtg tgactaagtg atggagtgtt gactgcagcc attcccggcc ccagcttgtg    1080
agagagatcc ttttaaattg aaagtaagct caaagttacc acgaagccac acatgtataa    1140
actgtgtgaa taatctgtgc acatacacaa accatgtgaa taatctgtgt acatgtataa    1200
actgtgtgaa taatctgtgt gcagcctttc cttacctact accttccagt gatcaggttt    1260
ggactgcctg tgtgctactg gaccctgaat gtccccaccg ctgtccctg tcttttacga     1320 ttctgacatt tttaataaat tcagcggctt cccctctgct ctgtgcctag ctataccttg    1380
gtactctgca ttttggtttc tgtgacattt ctctgtgact ctgctacatt ctcagatgac    1440
atgtgacaca gaaggtgttc cctctggaga catgtgatgt ccctgtcatt agtggaatca    1500
```

```
gatgccccca aactgttgtc cagtgtttgg gaaagtgaca cgtgaaggag gatcaggaaa    1560
agaggggtgg aaatcaagat gtgtctgagt atctcatgtc cctgagtggt ccaggctgct    1620
gacttcactc ccccaagtga gggaggccat ggtgagtaca cacacctcac acatactata    1680
tccaacacac acacacacac acacacacac acgcacgcac gcacgcacgc acgcacacat    1740
gcacacacac gaactacatt tcacaaacca catacgcata ttacaccccca aacgtatcac    1800
ctatacatac cacacataca caccccctcca cacatcacac ataccaca cccacacaca    1860
gcacacacat acataggcac acattcacac accacacata tacatttgtg tatgcataca    1920
tgcatacaca cacaggcaca cagacaccac acacatgcat tgtgtacgca cacatgcata    1980
cacacacata ggcacacatt gagcacacac atacatttgt gtacgcacac tacatagaca    2040
tatatgcatt tgtatatgca cacatgcatg cacacataca taggcacaca tagagcacac    2100
acatacattt gtgtatgcac acatgcacac accaatcaca tgggaagact caggttcttc    2160
actaaggttc acatgaactt agcagttcct ggttatctcg tgaaacttgg aagattgctg    2220
tggagaagag gaagcgttgg cttgagccct ggcagcaatt aaccccgccc agaagaagta    2280
ggtttaaaaa tgagagggtc tcaatgtgga acccgcaggg cgccagttca gagaagagac    2340
ctacccaagc caactgagag caaaggcaga gggatgaacc tgggatgtag tttgaacctc    2400
tgtaccagct gggcttcatg ctatttttgtt atatctttat taaatattct tttagtttta    2460
tgtgcgtgaa taccttgctt gcataaatgt atgggcactg tatgtgttct tggtgccggt    2520
ggaggccagg agagggcatg gatcctccgg agctggcgtt tgagacagtt gtgacccaca    2580
gtgtggggtc tgggaactgg gtcttagtgt tccgcaagtg cagctgggc tcttaacctc    2640
tgagccatcc ctccagcttc aagaaactta ttttcttagg acatggggga agggatccag    2700
ggctttaggc ttgtttgttc agcaaatact cttttcgtgt attttgaatt ttatttatt    2760
ttactttttt gggatagaat cacattctgc agctcaggct gggcctgaac tcatcaaaat    2820
cctcctgtct cagtctacca ggtgataaga ttactgatgt gagcctggct ttgacaagca    2880
ctttagagtc cccagcccctt ctggacactt gttccaagta taatatatat atatatatat    2940
atatatatat atatatatat atatattgtg tgtgtgtgtt tgtgtgtgta tgagacactt    3000
gctctaaggg tatcatatat atccttgatt tgcttttaat ttattttta attaaaaatg    3060
attagctaca tgtcacctgt atgcgtctgt atcatctata tatccttcct tccttctctc    3120
tctttctctc ttcttcttct caccccccaag catctatttt caaatccttg tgccgaggag    3180
atgccaagag tctcgttggg ggagatggtg agggggcgat acaggggaag agcaggagga    3240
aaggggacca gactggtgtg ggtctttgga gagctcagga gaatagcagc gatcttccct    3300
gtccctggtg tcacctctta cagccaacac cattttgtgg cctggcagaa gagttgtcaa    3360
gctggtcgca ggtctgccac acaaccccaa tctggcccca agaaaaggca cctgtgtgtg    3420
actctggggt taaaggcgct gcctggtcgt ctccagctgg acttgaaact cccgtttaat    3480
aaagagttct gcaaaataat acccgcagag tcacagtgcc aggttcccgt gctttcctga    3540
agcgccaggc acgggttccc taggaaatgg ggccttgctt gccaagctcc cacggcttgc    3600
cctgcaaacg gcctgaatga tctggcactc tgcgttgcca ctgggatgaa atggaaaaaa    3660
gaaaaagaag aagtgtctct ggaagcgggc gcgctcacac aaacccgcaa cgattgtgta    3720
aacactctcc attgagaatc tggagtgcgg ttgccctcta ctgggagct gaagacagct    3780
agtgggggcg gggggaggac cgtgctagca tccttccacg gtgctcgctg gctgtggtgc    3840
atgccgggaa ccgaaacgcg gaactaaagt caagtcttgc tttggtggaa ctgacaatca    3900
```

```
acgaaatcac ttcgattgtt ttcctctttt tactggaatt cttggatttg atagatgggg    3960
gaggatcaga gggggagggg aggggcgggg agacggaggg aggaggggag gaggggagga    4020
ggggaggagg ggaggagggg aagggatgga ggaaaatact aacttttcta attcaacatg    4080
acaaagattc ggagaaagtg caccgctagt gaccgggagg aggaatgccc tattgggcat    4140
tatattccct gtcgtctaat ggaatcaaac tcttggttcc agcaccaagg attctgagcc    4200
tatcctattc aagacagtaa ctacagccca cacggaagag gctatacaac tgaagaaata    4260
aaattttcac tttatttcat ttctgtgact gcatgttcac atgtagagag ccacctgtgt    4320
ctagggctg atgtgctggg cagtagagtt ctgagcccgt taactggaac aacccagaac    4380
tcccaccaca gttagagctt gctgagagag ggaggcctt ggtgagattt ctttgtgtat    4440
ttatttagag acagggtctc atactgtagt ccaagctagc ctccagctca cagaaattct    4500
cctgttccgg tttccaaagt actggagtta tgagtgtgtg ttaattgaac gctaagaatt    4560
tgctgattga agaaaacctc aagtgggttt ggctaatccc cacgacccca gaggctgagg    4620
caggaggaat gagagaattc aaggtttgcc agagccacag ggtgagctca atgtggagac    4680
tgtgagggtg agctcaatgt ggagactgtg agggtgagct caatgtggag actgtgaggg    4740
tgagctcaat gtggagactg tgagggtgag ctcaatgtgg agactgtgag ggtgagctca    4800
atgtggagac ctgtatcaag ataataatag tagtagtaac aatgcaggcg agggtgtggt    4860
tgagtggtag agcagttagt tgatttgaca tgcttgaggt ctcccggtcc atctgtggcc    4920
ctgcaacagg aagggaggga ggaaggggg gaacgagaga gaggaaagag agacagaagc    4980
taagatggg aatgagagag gaaggaagaa acgggaagaa attcagactc cttcctgagt    5040
tccgccaacg cctagtgaca tcctgtgcac accctaaggt ggcctttgtg tggcactggc    5100
ttgggtggtc gggaaaggca ttttcagctt gttgcagaac tgccacagta gcatgctggg    5160
tccgtgaaag tttctgcccg ttaacaagaa gtctctacta cttgtgacct caccagtgaa    5220
aatttcttta attgtctcct ggtgttctgg gttttgcatt tttgtttcta aggatacatt    5280
cctgggtgat gtcatgaagt ccccaaagac acagtgggc tgtgttggat tgggaaagat    5340
gatttatctg gggtgtcaaa aggaaaagaa gggaaacagg cacttgggaa aatgtcctcc    5400
cgcccacccg aattttggct tggcaaccgt ggtggaggag caagaaacac gtggacgttt    5460
gaggaggcat ggggtcctag gaggacagga agcagaagga gagagctggg ctgacagcct    5520
gcaggcattg cacagtttca gaaggagatt acagcatgac tgagttttta gggatccaac    5580
agggacctgg gtagagattc tgtgggctct gaggcaactt gacctcagcc agatggtatt    5640
tgaataacct gctcttagag ggaaaacaga catagcaaac agagccacgt ttagtgatga    5700
aactctcact ttgcctgagt catgtgcggc catgcccagg ggtcaggctg acactcaact    5760
caaaaacaag tgagaaattg aagacaatcc gtggtggcag ctactggaag ggccaccaca    5820
tccccagaaa gagtggagct gctaaaaagc catttgtgat aggcacagtt atcttgaatg    5880
catggagcag agattacgga aaaatcgaga atgttaatga ggcaacattc gagttgagtc    5940
attcagtgtg ggaaacccag acgcttccat cccctaaaag gaacatcttg ctctcagtca    6000
aaatggaaat aaaaattggg gcttgaattt ggcaaatgat tcagaactct gtgtaggtat    6060
tttcacacgc acagtggata attttcatgt tggagtttat ttgtgctaaa aggcagaaaa    6120
gggtaaaaag cacatcttaa gagttatgag gttctacgaa taaaaataat gttacttaca    6180
gctattcctt aattagtacc cccttccacc tgtggtaatt tcctgagata gtcagtgggg    6240
```

```
aaaagatctc tccttctctt ctttctcccc ctccctcct ctccctccct ccctcccct    6300 ctccctcctc tccctccctc cccctttcct tctttctttg ctccttctcc tctgcctcct    6360 tctcccttc ttcttcattt attctaagta gcttttaaca gcacaccaat tacctgtgta    6420
taacgggaaa acacaggctc aagcagctta gagaagattg atctgtgttc act          6473
```

<210> SEQ ID NO 2
<211> LENGTH: 7045
<212> TYPE: DNA
<213> ORGANISM: Cricetulus griseus

<400> SEQUENCE: 2

```
actagcgtgc aattcagagg tgggtgaaga taaaaggcaa acatttgagg ccatttcctt      60
atttggcacg gcacttagga agtgaacat gcctaatcta ctggtttgta ccaccttcc       120 ctataatgga ctgtttggga agctcctggg caaccgattc tggcatctca ttggtcagag     180
gcctgttaaa tggtactctt atttgcaaag aaggctgtaa cttgtagctt taaaagcctc     240
tcctcaagaa agaagggaga aaggatatgg ctagacatat ctaatagact taaccactgt    300
gaaaagcctt agtatgaatc agatagaacc tattttaac tcagttttga aaaaataat      360 ctttatattt atttgtgtgt gtgtgtgtgt gtgtgtgtgt gtgtgtgtgt gtgtgtgtgt    420
gaaccacatg tagcaggtgc tggaggaggc cagaagaggg caccagatct cctggaactg    480
acaccacaca tggttatgag ctgcctgatg tgggtgctgg gaactgaact ctcgtgttct    540
gcaagagcag caactgttct cttaactgat gagccatctc tccagccccc cccataattt    600
taattgttca ttttagtaaa ttttattcat aatcaattat cacagtataa acaatgatt     660 ttatatatat catatacata tcaaggatga cagtgagggg gatatgtgtg tgtgtgtgtg    720
tgtgtgtgtg tgtgtgtgtg tgtgttattt gtgtgtgtgc tttttaagaa ggtgccatag    780
tcactgcatt tctctgaagg atttcaaagg aatgagacat gtctgtctgc caggaaccct    840
atcttcctct ttgggaatct gacccaaatg aggtattctg aggaactgaa tgaagagctc    900
aagtagcagt gtcttaaacc caaatgtgct gtctagagaa agtcaacgtc atcagtgagc    960
tgaggagaga tttactgagc ggaagacaag cgctctttga tttaagtggc tcgaacagtc   1020
acggctgtgg agtggagcct gtgctcaggt ctgaggcagt ctttgctagc cagctgtgat   1080
gagcagtgaa gaaagggtgg agatggaggc agggtgggag cagggctatg gttcagacta   1140
ggtatcgtga gcacaccagc tggttgactt gtggtctgtg ggtcaggcgt tgtaaacgcc   1200
ctcagggtca ggcagtcaca ttgcttgaag ctgaatgggt gaggcaacac agagagtgca   1260
aagaaggcaa agtaccacct cttccccgac ccaggtcact tctgggttat agctgagact   1320
ccggacagca tgcaaccagc tggttagagc ttcaggaaa acttgatgtc tgcatgttgc    1380
tatgaaatgt gattcggtac atctggagaa aatttataat gctggctcag tcaagcactg   1440
aacaaaggta ccttggcttt gggagctaca tgacattgac ttgtaggcag acttttttt    1500 ttctgcccgc caattcccag ataaccaata tggaggctca atattaatta taaatgctcg   1560
gctgatagct caggcttgtt actagctaac tcttccaact taaatgaacc catttctatt   1620
atctacattc tgccacgtga ctttaccttg tacttcctgt ttcctctcct tgtctgactc   1680
tgcccttctg cttcccagag tccttagtct ggttctcctg cctaacctta tcctgcccag   1740
ctgctgacca agcatttata attaatatta agtctcccag tgagactctc atccagggag   1800 gacttggtg ctccccctc ctcattgcca tccgtgtctt cctcttccct cgcttccccc   1860
tcctcttcct gctcttcctc ctccacccct cctttcatag tattgatggc aagggtgttc   1920
```

```
tagaatggag gagtgcccat aggcatgcaa agaaaccagt taggatgctc tgtgaggggt    1980
tgtaatcata agcgatggac acaattcaag ccacagagtg aagacggaag gatgcactgt    2040
gctctagagc aacttctggg gcagaatcac agggtgagtt tctgacttga gggcgaagag    2100
gccacgagga agggagtgag tttgtctgag ctagaagcta cggcccacct cttggtagca    2160
gacctgccca caagcatgct tgttaatca tgtgggatct gattttcctc taaatctatg    2220
ttcaactctt aagaaaatgt gaattctcac attaaaattt agatatacgt cttttggtgg    2280
ggggggtgta aaaatcctc aagaatatgg atttctgggg gccggagaga tggctcagag    2340
gttaagagaa ctggttgctc ttctagacat tctgagttca attcccagca accacatggt    2400
ggctcacaac catctgtaat gcgacctggt gccatcttct gacatgcatg gatacatgca    2460
ggcagaaagc tgtatacata gtaaattgat aaatctttt ttaaaaagag tatgggattct    2520 gccgggtgtt ggtggcgcac gcctttaatc ccagcactct ggaggcagag gcaggtggat    2580
ctctgtgagt tcgagaccag cctggtctat aagagctagt tccaggacag cctccaaagc    2640
cacagagaaa ccctgtctcg aaaaaccaaa aaaaaaaaaa aaaaaaaaa aaaaaaaga     2700 gtatggattc taagaaagcc gtaacagctg gagctgtgta cggagttcag cgtggtacta    2760
gaagaacaga cattcatgat gaaacacccc aggattttta cttagtatct agtttccatt    2820
gttgttttga gaccggctct tatgctctcc aggctggcct caaactgctg atcttcccgc    2880
ctctacctct caagtcctgg gactacttgg ctcataaaac agttttttgtc gggctccctg    2940 aagttatggt tgtacaaacc gtggggtca atatactcac ttgggcagag agagaaggtc    3000
tgaatcccag acaatgactg catctcagga cagttgggaa gaggacaatg gcagaaggac    3060
ttagaaaaga tagactggag ggtggaaaag cagcaggaac agagaaacaa acaggaagc    3120 ttgctatcca gggccactct ggagtcctgt ggcaagatgg aagcgggcta ggggaataca    3180
tttgtgctac tgtgtgtgtg tgtgtgtgtg tgtgtgtgtg tgtgtgtgat caatgcctat    3240
caatgttgaa ggggaaatat gtataccaca ttgattctgg gagcaattct cagtatctgg    3300
cctagagaaa ggaatggccc ctgcagaata gacagagtga atggtgccct ttatcatttg    3360
ctaaagtgaa ggagaaataa acatccttcc atagagtttc aggtaaatga accccacagt    3420
tcatctgtgc cgtggtggag gcctggccaa cagttaaaaa gattagacac ggacaaagtc    3480
tgaaggaaac acctcgaata ggaagaggag agccacctca ttctgtaact ttcctcaagg    3540
ggaagatgtt ccaagagtgg gaataaatgg tcaaggggg gattttaat taggaaaacg    3600 atttcctgta tcacttgtga aactggaggt tgatttgggg cataggacaa tagatttgat    3660
gctttgcaaa aagctgtttc aaagcagaga aatggaatag agacaattat gtagcgagga    3720
gggagggtgg ggcgaagatg gagacagaga agtggaagct gactttaggg aagaggaaca    3780
tagaccacag gggcggggcg ggggcaggg gcgggggcg gggctcaaag gaggcagtgg    3840
gaacgttgct agtgttcgca gcgtaagcgt gaatgtgcaa gcgtcttgt ggtgtgtgac    3900 caggagtagc gtggctggct tgtgtgctgc ttgtaatccc agtctttgag gtttccacac    3960
tgttccacag tgggtgtgat tttccctcgg agagcatgag ggctctgctt tccccacatc    4020
ctccccagcg ttcgttggta tttgtttcca agatgttagt gggtgagaca aagcctctct    4080
gttgatttgc ctttaacagg tgacaaaaaa agctcaacca ggagacattt ttgccttctt    4140
ggaaggtaat gctcccatgt agagcaatgg gacccatctc taaggtgagg ctactcttgc    4200
agtttgcacc cagctcttct gatgcaggaa ggaagttggt gggcaagcaa gactgtttgc    4260
```

```
ttcttgcgat ggacacattc tgcacacaaa ggctcaggag gggagaaggc tgtttgatgt    4320
ttagcactca ggaaggcccc tgatgcatct gtgattagct gtctccatct gtggagcaga    4380
cacggactaa ctaaaaacca gtgttttaa attgtcaagc ctttaaggtg aggaaattga     4440
cttattgtgc tgggccatac gtagagcaag tgctctgcat tgggccaacc cccggctctg    4500
gtttctaggc accagaatgg cctagaacta actcacaatc ctcccattcc aggtctcagg    4560
tgctagaatg aaccactata ccagcctgcc tgcctgccta cctgccttcc taaattttaa    4620
atcatgggga gtaggggaga atacacttat cttagttagg gtttctattg ctgtgaagag    4680
acaccatgag catggcaact cttataaagg aaaacattta gttgggtggc agtttcagag    4740
gttttagtac attgtcatca tggctgggaa catgatggca tgcagacaga catggtgctg    4800
gagaaaggga tgagagtcct acatcttgca ggcaacagga cctcagctga gacactggct    4860
ggtaccctga gcataggaaa cctcacagcc caccctcaca gtgacatatt tccttcaaca    4920
aagccatacc tcctaatagt gccactccct atgagatgac agggccaatt acattcaaac    4980
tgctataaca ctttaaagta ttttattttt attattgtaa attatgtatg tagctgggtg    5040
gtggcagccg aggtgcacgc ctttaatccc agcacttggg aggcagaggc agatggatct    5100
ctgtgagttc aagaccagcc tggtctataa gagctagttg caaggaagga tatacaaaga    5160
acagttctag gatagccttc aaagccacag agaagtgctg tcttgaaaac caaaaattgt    5220
gctgggacct gtctctgctt tggttgcttc ccactccccc agagctggac tcttggtcaa    5280
cactgaatca gctgcaaaat aaactcctgg attcctctct tgtaacagga gcccgaagtc    5340
aggcgcccac ttgtcttctc gcaggattgc catagacttt ttctgtgtgc ccaccattcc    5400
agactgaagt agagatggca gtggcagaga ctgggaaggc tgcaacgaaa acaggaagtt    5460
attgcaccct gggaatagtc tggaaatgaa gcttcaaaac ttgcttcatg ttcagttgta    5520
cacagactca ctcccaggtt gactcacacg tgtaaatatt cctgactatg tctgcactgc    5580
ttttatctga tgcttccttc ccaaaatgcc aagtgtacaa ggtgagggaa tcacccttgg    5640
attcagagcc cagggtcgtc ctccttaacc tggacttgtc tttctccggc agcctctgac    5700
acccctcccc ccattttctc tatcagaagg tctgagcaga gttggggcac gctcatgtcc    5760
tgatacactc cttgtcttcc tgaagatcta acttctgacc cagaaagatg gctaaggtgg    5820
tgaagtgttt gacatgaaga cttggtctta agaactggag caggggaaaa aagtcggatg    5880
tggcagcatg tacccgaaat cccagaactg gggaggtaga gacggatgag tgcccggggc    5940
tagctggctg ctcagccagc ctagctgaat tgccaaattc caactcctat tgaaaaacct    6000
ttaccaaaca aacaaacaaa caaataataa caacaacaac aacaacaaac taccccatac    6060
aaggtgggcg ctcttggct cttgaggaat gactcaccca aacccaaagc ttgccacagc     6120
tgttctctgg cctaaatggg gtgggggtgg ggcagagaca gagacagaga gagacatgac    6180
ttcctgggct gggctgtgtg ctctaggcca ccaggaactt tcctgtcttg ctctctgtct    6240
ggcacagcca gagcaccagc acccagcagg tgcacacacc tccctccgtg cttcttgagc    6300
aaacacaggt gccttggtct gtctattgaa ccggagtaag ttcttgcaga tgtatgcatg    6360
gaaacaacat tgtcctggtt ttatttctac tgttgtgata aaaaccgggg aactccagga    6420
agcagctgag gcagaggcaa atgcaaggaa tgctgcctcc tagcttgctc cccatggctt    6480
gccgggcctg cttctgcaa gcccttctct cccattggc atgcctgaca tgaacagcgt      6540
ttgaaatgct ctcaaatgtc actttcaaag aaggcttctc tgatcttgct aactaaatca    6600
gaccatgttt caccgtgcat tatctttctg ctgtctgtct gtctgtctgt ctgtctatct    6660
```

```
gtctatcatc tatcaatcat ctatctatct atcttctatt tatctaccta tcattcaatc    6720
atctatcttc taactagtta tcatttattt atttgtttac ttactttttt tatttgagac    6780
agtatttctc tgagtgacag ccttggctgt cctggaaccc attctgtaac caggctgtcc    6840
tcaaactcac agagatccaa ctgcctctgc ctctctggtg ctggggttaa agacgtgcac    6900
caccaacgcc ccgctctatc atctatttat gtacttatta ttcagtcatt atctatcctc    6960
taactatcca tcatctgtct atccatcatc tatctatcta tctatctatc tatctatcta    7020
tctatcatcc atctataatc aattg                                          7045

<210> SEQ ID NO 3
<211> LENGTH: 6473
<212> TYPE: DNA
<213> ORGANISM: Cricetulus griseus

<400> SEQUENCE: 3
agtgaacaca gatcaatctt ctctaagctg cttgagcctg tgttttcccg ttatacacag      60
gtaattggtg tgctgttaaa agctacttag aataaatgaa gaagaaaggg agaaggaggc     120
agaggagaag gagcaaagaa agaaggaaag ggggagggag ggagaggagg gagggaggga     180
gggagggagg gagaggaggg gagggggaga agaagagaa ggagagatct tttccccact     240
gactatctca ggaaattacc acaggtggaa ggggtacta attaaggaat agctgtaagt     300
aacattattt ttattcgtag aacctcataa ctcttaagat gtgctttta ccctttctg     360 cctttagca caaataaact ccaacatgaa aattatccac tgtgcgtgtg aaaatacct a     420 cacagagttc tgaatcattt gccaaattca agccccaatt tttatttcca ttttgactga     480
gagcaagatg ttccttttag gggatggaag cgtctgggtt tcccacactg aatgactcaa     540
ctcgaatgtt gcctcattaa cattctcgat ttttccgtaa tctctgctcc atgcattcaa     600
gataactgtg cctatcacaa atggcttttt agcagctcca ctctttctgg ggatgtggtg     660
gcccttccag tagctgccac cacggattgt cttcaatttc tcacttgttt ttgagttgag     720
tgtcagcctg acccctgggc atggccgcac atgactcagg caaagtgaga gtttcatcac     780
taaacgtggc tctgtttgct atgtctgttt tccctctaag agcaggttat tcaaatacca     840
tctggctgag gtcaagttgc ctcagagccc acagaatctc tacccaggtc cctgttggat     900
ccctaaaaac tcagtcatgc tgtaatctcc ttctgaaact gtgcaatgcc tgcaggctgt     960
cagcccagct ctctccttct gcttcctgtc ctcctaggac cccatgcctc ctcaaacgtc    1020
cacgtgtttc ttgctcctcc accacggttg ccaagccaaa attcgggtgg gcgggaggac    1080
attttcccaa gtgcctgttt cccttctttt ccttttgaca ccccagataa atcatctttc    1140
ccaatccaac acagcccac tgtgtctttg gggacttcat gacatcaccc aggaatgtat    1200
ccttagaaac aaaaatgcaa aacccagaac accaggagac aattaaagaa attttcactg    1260
gtgaggtcac aagtagtaga gacttcttgt taacgggcag aaactttcac ggacccagca    1320
tgctactgtg gcagttctgc aacaagctga aaatgccttt cccgaccacc caagccagtg    1380
ccacacaaag gccaccttag ggtgtgcaca ggatgtcact aggcgttggc ggaactcagg    1440
aaggagtctg aatttcttcc cgtttcttcc ttcctctctc attccctatc ttagcttctg    1500
tctctctttc ctctctctcg ttccccccct tcctccctcc cttcctgttg cagggccaca    1560
gatggaccgg gagacctcaa gcatgtcaaa tcaactaact gctctaccac tcaaccacac    1620
cctcgcctgc attgttacta ctactattat tatcttgata caggtctcca cattgagctc    1680
```

| | |
|---|---|
| accctcacag tctccacatt gagctcaccc tcacagtctc cacattgagc tcaccctcac | 1740 |
| agtctccaca ttgagctcac cctcacagtc tccacattga gctcaccctc acagtctcca | 1800 |
| cattgagctc accctgtggc tctggcaaac cttgaattct ctcattcctc ctgcctcagc | 1860 |
| ctctggggtc gtgggatta gccaaaccca cttgaggttt tcttcaatca gcaaattctt | 1920 |
| agcgttcaat taacacacac tcataactcc agtactttgg aaaccggaac aggagaattt | 1980 |
| ctgtgagctg gaggctagct tggactacag tatgagaccc tgtctctaaa taaatacaca | 2040 |
| aagaaatctc accaagggcc tccctctctc agcaagctct aactgtggtg ggagttctgg | 2100 |
| gttgttccag ttaacgggct cagaactcta ctgcccagca catcagcccc tagacacagg | 2160 |
| tggctctcta catgtgaaca tgcagtcaca gaaatgaaat aaagtgaaaa ttttatttct | 2220 |
| tcagttgtat agcctcttcc gtgtgggctg tagttactgt cttgaatagg ataggctcag | 2280 |
| aatccttggt gctggaacca agagtttgat tccattagac gacagggaat ataatgccca | 2340 |
| atagggcatt cctcctcccg gtcactagcg gtgcactttc tccgaatctt tgtcatgttg | 2400 |
| aattagaaaa gttagtattt tcctccatcc cttcccctcc tcccctcctc cctcctccc | 2460 |
| ctcctcccct cctccctccg tctccccgcc cctcccctcc ccctctgatc ctcccccatc | 2520 |
| tatcaaatcc aagaattcca gtaaaaagag gaaaacaatc gaagtgattt cgttgattgt | 2580 |
| cagttccacc aaagcaagac ttgactttag ttccgcgttt cggttcccgg catgcaccac | 2640 |
| agccagcgag caccgtggaa ggatgctagc acggtcctcc ccccgccccc actagctgtc | 2700 |
| ttcagctccc cagtagaggg caaccgcact ccagattctc aatggagagt gtttacacaa | 2760 |
| tcgttgcggg tttgtgtgag cgcgcccgct tccagagaca cttcttcttt ttcttttttc | 2820 |
| catttcatcc cagtggcaac gcagagtgcc agatcattca ggccgtttgc agggcaagcc | 2880 |
| gtgggagctt ggcaagcaag gccccatttc ctagggaacc cgtgcctggc gcttcaggaa | 2940 |
| agcacgggaa cctggcactg tgactctgcg ggtattattt tgcagaactc tttattaaac | 3000 |
| gggagtttca gtccagctg gagacgacca ggcagcgcct ttaaccccag agtcacacac | 3060 |
| aggtgccttt tcttggggcc agattggggt tgtgtggcag acctgcgacc agcttgacaa | 3120 |
| ctcttctgcc aggccacaaa atggtgttgg ctgtaagagg tgacaccagg gacagggaag | 3180 |
| atcgctgcta ttctcctgag ctctccaaag acccacacca gtctgtcccc ctttcctcct | 3240 |
| gctcttcccc tgtatcgccc cctccaccatc tccccaacg agactcttgg catctcctcg | 3300 |
| gcacaaggat ttgaaaatag atgcttgggg gtgagaagaa gaagagagaa agagagagaa | 3360 |
| ggaaggaagg atatatagat gatacagacg catacaggtg acatgtagct aatcattttt | 3420 |
| aattaaaaaa taaattaaaa gcaaatcaag gatatatatg atacccttag agcaagtgtc | 3480 |
| tcatacacac acaaacacac acacacaata tatatatata tatatatata tatatatata | 3540 |
| tatatatata ttatacttgg aacaagtgtc cagaagggct ggggactcta aagtgcttgt | 3600 |
| caaagccagg ctcacatcag taatcttatc acctggtaga ctgagacagg aggattttga | 3660 |
| tgagttcagg cccagcctga gctgcagaat gtgattctat cccaaaaaag taaaataaaa | 3720 |
| taaaattcaa aatacacgaa aagagtattt gctgaacaaa caagcctaaa gccctggatc | 3780 |
| ccttccccca tgtcctaaga aaataagttt cttgaagctg gagggatggc tcagaggtta | 3840 |
| agagccccag ctgcacttgc ggaacactaa gacccagttc ccagacccca cactgtgggt | 3900 |
| cacaactgtc tcaaacgcca gctccggagg atccatgccc tctcctggcc tccaccggca | 3960 |
| ccaagaacac atacagtgcc catacatta tgcaagcaag gtattcacgc acataaaact | 4020 |
| aaaagaatat ttaataaaga tataacaaaa tagcatgaag cccagctggt acagaggttc | 4080 |

```
aaactacatc ccaggttcat ccctctgcct ttgctctcag ttggcttggg taggtctctt    4140
ctctgaactg gcgccctgcg ggttccacat tgagaccctc tcattttttaa acctacttct    4200 tctgggcggg gttaattgct gccagggctc aagccaacgc ttcctcttct ccacagcaat    4260
cttccaagtt tcacgagata accaggaact gctaagttca tgtgaacctt agtgaagaac    4320
ctgagtcttc ccatgtgatt ggtgtgtgca tgtgtgcata cacaaatgta tgtgtgtgct    4380
ctatgtgtgc ctatgtatgt gtgcatgcat gtgtgcatat acaaatgcat atatgtctat    4440
gtagtgtgcg tacacaaatg tatgtgtgtg ctcaatgtgt gcctatgtgt gtgtatgcat    4500
gtgtgcgtac acaatgcatg tgtgtggtgt ctgtgtgcct gtgtgtgtat gcatgtatgc    4560
atacacaaat gtatatgtgt ggtgtgtgaa tgtgtgccta tgtatgtgtg tgctgtgtgt    4620
gggtgtggta tgtgtgtgat gtgtggaggg gtgtgtatgt gtggtatgta taggtgatac    4680
gtttggggtg taatatgcgt atgtggtttg tgaaatgtag ttcgtgtgtg tgcatgtgtg    4740
cgtgcgtgcg tgcgtgcgtg cgtgtgtgtg tgtgtgtgtg tgtgtgtgtt ggatatagta    4800
tgtgtgaggt gtgtgtactc accatggcct ccctcacttg ggggagtgaa gtcagcagcc    4860
tggaccactc agggacatga gatactcaga cacatcttga tttccacccc tcttttcctg    4920
atcctccttc acgtgtcact ttcccaaaca ctggacaaca gtttggggc atctgattcc    4980 actaatgaca gggacatcac atgtctccag agggaacacc ttctgtgtca catgtcatct    5040
gagaatgtag cagagtcaca gagaaatgtc acagaaacca aatgcagag taccaaggta    5100 tagctaggca cagagcagag gggaagccgc tgaatttatt aaaaatgtca gaatcgtaaa    5160
agacagggga cagcggtggg gacattcagg gtccagtagc acacaggcag tccaaacctg    5220
atcactggaa ggtagtaggt aaggaaaggc tgcacacaga ttattcacac agtttataca    5280
tgtacacaga ttattcacat ggtttgtgta tgtgcacaga ttattcacac agtttataca    5340
tgtgtggctt cgtggtaact ttgagcttac tttcaattta aaaggatctc tctcacaagc    5400
tggggccggg aatggctgca gtcaacactc catcacttag tcacactgtg caaacagcac    5460
ctcctgactc atggtgactt gtagtaaaat gaagaggcca catttgcatc caagacagct    5520
catcagtacc tagtgaagaa tctgtccctg agtatttgca tgaatggacc cgggtccagg    5580
gcctggctgg gagtctccag gtgttgcagc cagaatgtca ttgtgttttt tcaggatccc    5640
agaagtttct aaaatacagg ccaagtactc atttgtgtta caaagtatct gactaataga    5700
agtgattagg taacacaaag ccttttaaaa accgagatca cccttgtcat gtccctggcc    5760
tcttagaaca agatccaagc ttttgctggt tgacaagtgg ggccatccag tgcgtctccg    5820
ttcctgctac ttcatctgga agacctctcc cactaacttg cccctgaccc ctcacacctg    5880
ctgtttcctt tccacccgga agtgcttgtc taggctttca tggccatctg actgagcatc    5940
taggcctcag tccagtggtc cctcagctct ctctagtcac tgtactaatg gaaacggcca    6000
ctaactacat tttcaatatg gaagcctcct cctcaggaac ctccaagggc agaagcctcc    6060
agagaaccac tcctgacccc ctggagttct gagtgcttct ggccctctct gtgtctgcag    6120
gactattcac cacttgtgtt gaatggttca gtcctcacct cctctggcat gtgctcagtt    6180
ctcatctcat tggggagtcc ttcccaggtc actcttctct cctgtctttg aagtgttttt    6240
ttccttcatg gtatttctgt ctgggcacac acacagacac acatacacac acatacacac    6300
ccatgcagta tggcagatac atcacctatg tttcagattt ttattctacc atcacccaat    6360
```

| | |
|---|---:|
| acctgaatcc ccgaaaaagc cttagaaagc caggaatttg tgtattttg tcagcactcc | 6420 |
| accccagcac ctgaagccaa gcctgactta atattttggg ttttgtttct aga | 6473 |

<210> SEQ ID NO 4
<211> LENGTH: 7045
<212> TYPE: DNA
<213> ORGANISM: Cricetulus griseus

<400> SEQUENCE: 4

| | |
|---|---:|
| caattgatta tagatggatg atagatagat agatagatag atagatagat agatagatga | 60 |
| tggatagaca gatgatggat agttagagga tagataatga ctgaataata agtcataaaa | 120 |
| tagatgatag agcggggcgt tggtggtgca cgtctttaac cccagcacca gagaggcaga | 180 |
| ggcagttgga tctctgtgag tttgaggaca gcctggttac agaatgggtt ccaggacagc | 240 |
| caaggctgtc actcagagaa atactgtctc aaataaaaaa agtaagtaaa caaataaata | 300 |
| aatgataact agttagaaga tagatgattg aatgataggt agataaatag aagatagata | 360 |
| gatagatgat tgatagatga tagacagata gacagacaga cagacagaca gacagcagaa | 420 |
| agataatgca cggtgaaaca tggtctgatt tagttagcaa gatcagagaa gccttctttg | 480 |
| aaagtgacat ttgagagcat ttcaaacgct gttcatgtca ggcatgccaa tggggagaga | 540 |
| agggcttgca gaaagcaggc ccggcaagcc atggggagca agctaggagg cagcattcct | 600 |
| tgcatttgcc tctgcctcag ctgcttcctg gagttccccg gttttatca caacagtaga | 660 |
| aataaaacca ggacaatgtt gtttccatgc atacatctgc aagaacttac tccggttcaa | 720 |
| tagacagacc aaggcacctg tgtttgctca agaagcacgg agggaggtgt gtgcacctgc | 780 |
| tgggtgctgg tgctctggct gtgccagaca gagagcaaga caggaaagtt cctggtggcc | 840 |
| tagagcacac agcccagccc aggaagtcat gtctctctct gtctctgtct ctgccccacc | 900 |
| cccacccat ttaggccaga gaacagctgt ggcaagcttt gggtttgggt gagtcattcc | 960 |
| tcaagagcca agagccgccc accttgtatg gggtagtttg ttgttgttgt tgttgttatt | 1020 |
| atttgtttgt ttgtttgttt ggtaaaggtt tttcaatagg agttggaatt tggcaattca | 1080 |
| gctaggctgg ctgagcagcc agctagcccc gggcactcat ccgtctctac ctcccccagtt | 1140 |
| ctgggatttc gggtacatgc tgccacatcc gacttttttc ccctgctcca gttcttaaga | 1200 |
| ccaagtcttc atgtcaaaca cttcaccacc ttagccatct ttctgggtca gaagttagat | 1260 |
| cttcaggaag acaaggagtg tatcaggaca tgagcgtgcc ccaactctgc tcagaccttc | 1320 |
| tgatagagaa aatgggggga ggggtgtcag aggctgccgg agaaagacaa gtccaggtta | 1380 |
| aggaggacga ccctgggctc tgaatccaag ggtgattccc tcaccttgta cacttggcat | 1440 |
| tttgggaagg aagcatcaga taaaagcagt gcagacatag tcaggaatat ttacacgtgt | 1500 |
| gagtcaacct gggagtgagt ctgtgtacaa ctgaacatga agcaagtttt gaagcttcat | 1560 |
| ttccagacta ttcccagggt gcaataactt cctgttttcg ttgcagcctt cccagtctct | 1620 |
| gccactgcca tctctacttc agtctggaat ggtgggcaca cagaaaaagt ctatggcaat | 1680 |
| cctgcgagaa gacaagtggg cgcctgactt cgggctcctg ttacaagaga ggaatccagg | 1740 |
| agtttatttt gcagctgatt cagtgttgac caagagtcca gctctggggg agtgggaagc | 1800 |
| aaccaaagca gagacaggtc ccagcacaat ttttggtttt caagacagca cttctctgtg | 1860 |
| gctttgaagg ctatcctaga actgttcttt gtatatcctt ccttgcaact agctcttata | 1920 |
| gaccaggctg gtcttgaact cacagagatc catctgcctc tgcctcccaa gtgctgggat | 1980 |
| taaaggcgtg cacctcggct gccaccaccc agctacatac ataatttaca ataataaaaa | 2040 |

```
taaaatactt taaagtgtta tagcagtttg aatgtaattg gccctgtcat ctcataggga      2100
gtggcactat taggaggtat ggctttgttg aaggaaatat gtcactgtga gggtgggctg      2160
tgaggtttcc tatgctcagg gtaccagcca gtgtctcagc tgaggtcctg ttgcctgcaa      2220
gatgtaggac tctcatccct ttctccagca ccatgtctgt ctgcatgcca tcatgttccc      2280
agccatgatg acaatgtact aaaacctctg aaactgccac ccaactaaat gttttccttt      2340
ataagagttg ccatgctcat ggtgtctctt cacagcaata gaaaccctaa ctaagataag      2400
tgtattctcc cctactcccc atgatttaaa atttaggaag gcaggtaggc aggcaggcag      2460
gctggtatag tggttcattc tagcacctga gacctggaat gggaggattg tgagttagtt      2520
ctaggccatt ctggtgccta gaaaccagag ccggggttg gcccaatgca gagcacttgc       2580
tctacgtatg gcccagcaca ataagtcaat ttcctcacct taaaggcttg acaatttaaa      2640
aacactggtt tttagttagt ccgtgtctgc tccacagatg gagacagcta atcacagatg      2700
catcagggc cttcctgagt gctaaacatc aaacagcctt ctccctcct gagcctttgt        2760
gtgcagaatg tgtccatcgc aagaagcaaa cagtcttgct tgcccaccaa cttccttcct      2820
gcatcagaag agctgggtgc aaactgcaag agtagcctca ccttagagat gggtcccatt      2880
gctctacatg ggagcattac cttccaagaa ggcaaaaatg tctcctggtt gagctttttt      2940
tgtcacctgt taaaggcaaa tcaacagaga ggctttgtct cacccactaa catcttggaa      3000
acaaatacca acgaacgctg ggaggatgt ggggaaagca gagccctcat gctctccgag       3060
ggaaaatcac acccactgtg gaacagtgtg gaaacctcaa agactgggat tacaagcagc      3120
acacaagcca gccacgctac tcctggtcac acaccacaaa gacgcttgca cattcacgct      3180
tacgctgcga acactagcaa cgttcccact gcctccttg agcccgccc ccgcccctg         3240
cccccgccc cgcccctgtg gtctatgttc ctcttcccta aagtcagctt ccacttctct       3300
gtctccatct tcgccccacc ctccctcctc gctacataat tgtctctatt ccatttctct      3360
gctttgaaac agcttttgc aaagcatcaa atctattgtc ctatgcccca aatcaacctc       3420
cagtttcaca agtgatacag gaaatcgttt tcctaattaa aaatccccc tttgaccatt       3480
tattcccact cttggaacat cttccccttg aggaaagtta cagaatgagg tggctctcct     3540
cttcctattc gaggtgtttc cttcagactt tgtccgtgtc taatcttttt aactgttggc      3600
caggcctcca ccacggcaca gatgaactgt ggggttcatt tacctgaaac tctatggaag     3660
gatgtttatt tctccttcac tttagcaaat gataaagggc accattcact ctgtctattc     3720
tgcaggggcc attcctttct ctaggccaga tactgagaat tgctcccaga atcaatgtgg     3780
tatacatatt tcccttcaa cattgatagg cattgatcac acacacacac acacacacac     3840
acacacacac acacagtagc acaaatgtat tcccctagcc cgcttccatc ttgccacagg     3900
actccagagt ggccctggat agcaagcttc ctgttttgtt tctctgttcc tgctgctttt     3960
ccaccctcca gtctatcttt tctaagtcct tctgccattg tcctcttccc aactgtcctg     4020
agatgcagtc attgtctggg attcagacct tctctctctg cccaagtgag tatattgacc     4080
cccacggttt gtacaaccat aacttcaggg agcccgacaa aaactgtttt atgagccaag     4140
tagtcccaga acttgagagg tagaggcggg aagatcagca gtttgaggcc agcctggaga     4200
gcataagagc cggtctcaaa acaacaatgg aaactagata ctaagtaaaa atcctggggt     4260
gtttcatcat gaatgtctgt tcttctagta ccacgctgaa ctccgtacac agctccagct     4320
gttacggctt tcttagaatc catactcttt tttttttttt tttttttttt tttttttgg     4380
```

```
tttttcgaga cagggtttct ctgtggcttt ggaggctgtc ctggaactag ctcttataga  4440
ccaggctggt ctcgaactca cagagatcca cctgcctctg cctccagagt gctgggatta  4500
aaggcgtgcg ccaccaacac ccggcagaat ccatactctt tttaaaaaaa gatttatcaa  4560
tttactatgt atacagcttt ctgcctgcat gtatccatgc atgtcagaag atggcaccag  4620
gtcgcattac agatggttgt gagccaccat gtggttgctg ggaattgaac tcagaatgtc  4680
tagaagagca accagttctc ttaacctctg agccatctct ccggccccca gaaatccata  4740
ttcttgagga ttttttacac cccccccacc aaaagacgta tatctaaatt ttaatgtgag  4800
aattcacatt ttcttaagag ttgaacatag atttagagga aaatcagatc ccacatgatt  4860
aacaaagcat gcttgtgggc aggtctgcta ccaagaggtg ggccgtagct tctagctcag  4920
acaaactcac tcccttcctc gtggcctctt cgccctcaag tcagaaactc accctgtgat  4980
tctgccccag aagttgctct agagcacagt gcatccttcc gtcttcactc tgtggcttga  5040
attgtgtcca tcgcttatga ttacaacccc tcacagagca tcctaactgg tttcttttgca  5100 tgcctatggg cactcctcca ttctagaaca cccttgccat caatactatg aaaggagggg  5160
tggaggagga agagcaggaa gaggaggggg aagcgaggga agaggaagac acggatggca  5220
atgaggaggg gggagcaccc aagtcctccc tggatgagag tctcactggg agacttaata  5280
ttaattataa atgcttggtc agcagctggg caggataagg ttaggcagga gaaccagact  5340
aaggactctg ggaagcagaa gggcagagtc agacaaggag aggaaacagg aagtacaagg  5400
taaagtcacg tggcagaatg tagataatag aaatgggttc atttaagttg gaagagttag  5460
ctagtaacaa gcctgagcta tcagccgagc atttataatt aatattgagc ctccatattg  5520
gttatctggg aattggcggg cagaaaaaaa aaagtctgcc tacaagtcaa tgtcatgtag  5580
ctcccaaagc caaggtacct ttgttcagtg cttgactgag ccagcattat aaattttctc  5640
cagatgtacc gaatcacatt tcatagcaac atgcagacat caagttttcc ctgaagctct  5700
aaccagctgg ttgcatgctg tccggagtct cagctataac ccagaagtga cctgggtcgg  5760
ggaagaggtg gtactttgcc ttctttgcac tctctgtgtt gcctcaccca ttcagcttca  5820
agcaatgtga ctgcctgacc ctgagggcgt ttacaacgcc tgacccacag accacaagtc  5880
aaccagctgg tgtgctcacg atacctagtc tgaaccatag ccctgctccc accctgcctc  5940
catctccacc ctttcttcac tgctcatcac agctggctag caaagactgc ctcagacctg  6000
agcacaggct ccactccaca gccgtgactg ttcgagccac ttaaatcaaa gagcgcttgt  6060
cttccgctca gtaaatctct cctcagctca ctgatgacgt tgactttctc tagacagcac  6120
atttgggttt aagacactgc tacttgagct cttcattcag ttcctcagaa tacctcatttt  6180 gggtcagatt cccaaagagg aagatagggt tcctggcaga cagacatgtc tcattccttt  6240
gaaatccttc agagaaatgc agtgactatg gcaccttctt aaaaagcaca cacacaaata  6300
acacacacac acacacacac acacacacac acacacacac atatccccct cactgtcatc  6360
cttgatatgt atatgatata tataaaatca ttgttttata ctgtgataat tgattatgaa  6420
taaaatttac taaaatgaac aattaaaatt atgggggggg ctggagagat ggctcatcag  6480
ttaagagaac agttgctgct cttgcagaac acgagagttc agttcccagc acccacatca  6540
ggcagctcat aaccatgtgt ggtgtcagtt ccaggagatc tggtgccctc ttctggcctc  6600
ctccagcacc tgctacatgt ggttcacaca cacacacaca cacacacaca cacacacaca  6660
cacacacaca caaataaata taagagattat ttttttcaaa actgagttaa aaataggttc  6720
tatctgattc atactaaggc ttttcacagt ggttaagtct attagatatg tctagccata  6780
```

-continued

```
tcctttctcc cttctttctt gaggagaggc ttttaaagct acaagttaca gccttctttg    6840
caaataagag taccatttaa caggcctctg accaatgaga tgccagaatc ggttgcccag    6900
gagcttccca acagtccat tatagggaaa ggtggtacaa accagtagat taggcatgtt    6960
ccacttccta agtgccgtgc caaataagga aatggcctca aatgtttgcc ttttatcttc    7020
acccacctct gaattgcacg ctagt                                          7045
```

<210> SEQ ID NO 5
<211> LENGTH: 13515
<212> TYPE: DNA
<213> ORGANISM: Cricetulus griseus

<400> SEQUENCE: 5

```
tctagaaaca aaaccaaaaa tattaagtca ggcttggctt caggtgctgg ggtggagtgc      60
tgacaaaaat acacaaattc ctggctttct aaggctttt cggggattca ggtattgggt     120
gatggtagaa taaaaatctg aaacataggt gatgtatctg ccatactgca tgggtgtgta     180
tgtgtgtgta tgtgtgtctg tgtgtgtgcc cagacagaaa taccatgaag gaaaaaaaca     240
cttcaaagac aggagagaag agtgacctgg gaaggactcc ccaatgagat gagaactgag     300
cacatgccag aggaggtgag gactgaacca ttcaacacaa gtggtgaata gtcctgcaga     360
cacagagagg ccagaagca ctcagaactc caggggtca ggagtggttc tctgaaggct      420
tctgcccttg gaggttcctg aggaggaggc ttccatattg aaaatgtagt tagtggccgt     480
ttccattagt acagtgacta gagagagctg agggaccact ggactgaggc ctagatgctc     540
agtcagatgg ccatgaaagc ctagacaagc acttccgggt ggaaaggaaa cagcaggtgt     600
gaggggtcag gggcaagtta gtgggagagg tcttccagat gaagtagcag gaacggagac     660
gcactggatg gccccacttg tcaaccagca aaagcttgga tcttgttcta agaggccagg     720
gacatgacaa gggtgatctc ggttttaaa aggctttgtg ttacctaatc acttctatta     780
gtcagatact ttgtaacaca aatgagtact tggcctgtat tttagaaact tctgggatcc     840
tgaaaaaaca caatgacatt ctggctgcaa cacctggaga ctcccagcca ggccctggac     900
ccgggtccat tcatgcaaat actcagggac agattcttca ctaggtactg atgagctgtc     960
ttggatgcaa atgtggcctc ttcattttac tacaagtcac catgagtcag gaggtgctgt    1020
ttgcacagtg tgactaagtg atggagtgtt gactgcagcc attcccggcc ccagcttgtg    1080
agagagatcc ttttaaattg aaagtaagct caaagttacc acgaagccac acatgtataa    1140
actgtgtgaa taatctgtgc acatacacaa accatgtgaa taatctgtgt acatgtataa    1200
actgtgtgaa taatctgtgt gcagcctttc cttacctact accttccagt gatcaggttt    1260
ggactgcctg tgtgctactg gaccctgaat gtccccaccg ctgtccctg tcttttacga     1320 ttctgacatt tttaataaat tcagcggctt ccctctgct ctgtgcctag ctataccttg     1380
gtactctgca ttttggtttc tgtgacattt ctctgtgact ctgctacatt tcagatgac     1440 atgtgacaca gaaggtgttc cctctggaga catgtgatgt ccctgtcatt agtggaatca    1500
gatgccccca aactgttgtc cagtgtttgg gaaagtgaca cgtgaaggag gatcaggaaa    1560
agaggggtgg aaatcaagat gtgtctgagt atctcatgtc cctgagtggt ccaggctgct    1620
gacttcactc ccccaagtga gggaggccat ggtgagtaca cacacctcac acatactata    1680
tccaacacac acacacacac acacacacac acgcacgcac gcacgcacgc acgcacacat    1740
gcacacacac gaactacatt tcacaaacca catacgcata ttacaccca aacgtatcac    1800
```

-continued

| | | | | |
|---|---|---|---|---|
| ctatacatac | cacacataca | cacccctcca | cacatcacac | ataccaca | cccacacaca | 1860 |
| gcacacacat | acataggcac | acattcacac | accacacata | tacatttgtg | tatgcataca | 1920 |
| tgcatacaca | cacaggcaca | cagacaccac | acacatgcat | tgtgtacgca | cacatgcata | 1980 |
| cacacacata | ggcacacatt | gagcacacac | atacatttgt | gtacgcacac | tacatagaca | 2040 |
| tatatgcatt | tgtatatgca | cacatgcatg | cacacataca | taggcacaca | tagagcacac | 2100 |
| acatacattt | gtgtatgcac | acatgcacac | accaatcaca | tgggaagact | caggttcttc | 2160 |
| actaaggttc | acatgaactt | agcagttcct | ggttatctcg | tgaaacttgg | aagattgctg | 2220 |
| tggagaagag | gaagcgttgg | cttgagccct | ggcagcaatt | aaccccgccc | agaagaagta | 2280 |
| ggtttaaaaa | tgagagggtc | tcaatgtgga | acccgcaggg | cgccagttca | gagaagagac | 2340 |
| ctacccaagc | caactgagag | caaaggcaga | gggatgaacc | tgggatgtag | tttgaacctc | 2400 |
| tgtaccagct | gggcttcatg | ctattttgtt | atatctttat | taaatattct | tttagtttta | 2460 |
| tgtgcgtgaa | taccttgctt | gcataaatgt | atgggcactg | tatgtgttct | tggtgccggt | 2520 |
| ggaggccagg | agagggcatg | gatcctccgg | agctggcgtt | tgagacagtt | gtgacccaca | 2580 |
| gtgtggggtc | tgggaactgg | gtcttagtgt | tccgcaagtg | cagctggggc | tcttaacctc | 2640 |
| tgagccatcc | ctccagcttc | aagaaactta | ttttcttagg | acatggggga | agggatccag | 2700 |
| ggctttaggc | ttgtttgttc | agcaaatact | cttttcgtgt | attttgaatt | ttattttatt | 2760 |
| ttacttttt | gggatagaat | cacattctgc | agctcaggct | gggcctgaac | tcatcaaaat | 2820 |
| cctcctgtct | cagtctacca | ggtgataaga | ttactgatgt | gagcctggct | ttgacaagca | 2880 |
| ctttagagtc | cccagccctt | ctggacactt | gttccaagta | taatatatat | atatatatat | 2940 |
| atatatatat | atatatatat | atatattgtg | tgtgtgtgtt | tgtgtgtgta | tgagacactt | 3000 |
| gctctaaggg | tatcatatat | atccttgatt | tgcttttaat | ttattttta | attaaaaatg | 3060 |
| attagctaca | tgtcacctgt | atgcgtctgt | atcatctata | tatccttcct | tccttctctc | 3120 |
| tctttctctc | ttcttcttct | cacccccaag | catctatttt | caaatccttg | tgccgaggag | 3180 |
| atgccaagag | tctcgttggg | ggagatggtg | agggggcgat | acaggggaag | agcaggagga | 3240 |
| aaggggggaca | gactggtgtg | ggtctttgga | gagctcagga | gaatagcagc | gatcttccct | 3300 |
| gtccctggtg | tcacctctta | cagccaacac | cattttgtgg | cctggcagaa | gagttgtcaa | 3360 |
| gctggtcgca | ggtctgccac | acaaccccaa | tctggcccca | agaaaaggca | cctgtgtgtg | 3420 |
| actctggggt | taaaggcgct | gcctggtcgt | ctccagctgg | acttgaaact | cccgtttaat | 3480 |
| aaagagttct | gcaaaataat | acccgcagag | tcacagtgcc | aggttcccgt | gctttcctga | 3540 |
| agcgccaggc | acgggttccc | taggaaatgg | ggccttgctt | gccaagctcc | cacggcttgc | 3600 |
| cctgcaaacg | gcctgaatga | tctggcactc | tgcgttgcca | ctgggatgaa | atggaaaaaa | 3660 |
| gaaaagaag | aagtgtctct | ggaagcgggc | gcgctcacac | aaacccgcaa | cgattgtgta | 3720 |
| aacactctcc | attgagaatc | tggagtgcgg | ttgccctcta | ctggggagct | gaagacagct | 3780 |
| agtgggggcg | ggggaggac | cgtgctagca | tccttccacg | gtgctcgctg | gctgtggtgc | 3840 |
| atgccgggaa | ccgaaacgcg | gaactaaagt | caagtcttgc | tttggtggaa | ctgacaatca | 3900 |
| acgaaatcac | ttcgattgtt | ttcctctttt | tactggaatt | cttggatttg | atagatgggg | 3960 |
| gaggatcaga | gggggagggg | aggggcgggg | agacggaggg | aggaggggag | gagggagga | 4020 |
| gggaggagg | ggaggagggg | aagggatgga | ggaaaatact | aacttttcta | attcaacatg | 4080 |
| acaaagattc | ggagaaagtg | caccgctagt | gaccgggagg | aggaatgccc | tattgggcat | 4140 |
| tatattccct | gtcgtctaat | ggaatcaaac | tcttggttcc | agcaccaagg | attctgagcc | 4200 |

-continued

```
tatcctattc aagacagtaa ctacagccca cacggaagag gctatacaac tgaagaaata    4260
aaattttcac tttatttcat ttctgtgact gcatgttcac atgtagagag ccacctgtgt    4320 ctagggctg atgtgctggg cagtagagtt ctgagcccgt taactggaac aacccagaac    4380
tcccaccaca gttagagctt gctgagagag ggaggccctt ggtgagattt ctttgtgtat    4440
ttatttagag acagggtctc atactgtagt ccaagctagc ctccagctca cagaaattct    4500
cctgttccgg tttccaaagt actggagtta tgagtgtgtg ttaattgaac gctaagaatt    4560
tgctgattga agaaaacctc aagtgggttt ggctaatccc cacgacccca gaggctgagg    4620
caggaggaat gagagaattc aaggtttgcc agagccacag ggtgagctca atgtggagac    4680
tgtgagggtg agctcaatgt ggagactgtg agggtgagct caatgtggag actgtgaggg    4740
tgagctcaat gtggagactg tgagggtgag ctcaatgtgg agactgtgag ggtgagctca    4800
atgtggagac ctgtatcaag ataataatag tagtagtaac aatgcaggcg agggtgtggt    4860
tgagtggtag agcagttagt tgatttgaca tgcttgaggt ctcccggtcc atctgtggcc    4920
ctgcaacagg aagggaggga ggaaggggggg gaacgagaga gaggaaagag agacagaagc    4980
taagataggg aatgagagag gaaggaagaa acgggaagaa attcagactc cttcctgagt    5040
tccgccaacg cctagtgaca tcctgtgcac accctaaggt ggcctttgtg tggcactggc    5100
ttgggtggtc gggaaaggca ttttcagctt gttgcagaac tgccacagta gcatgctggg    5160
tccgtgaaag tttctgcccg ttaacaagaa gtctctacta cttgtgacct caccagtgaa    5220 aatttctttta attgtctcct ggtgttctgg gttttgcatt tttgtttcta aggatacatt    5280
cctgggtgat gtcatgaagt ccccaaagac acagtggggc tgtgttggat tgggaaagat    5340
gatttatctg gggtgtcaaa aggaaaagaa gggaaacagg cacttgggaa aatgtcctcc    5400
cgcccacccg aattttggct tggcaaccgt ggtggaggag caagaaacac gtggacgttt    5460
gaggaggcat ggggtcctag gaggacagga agcagaagga gagagctggg ctgacagcct    5520
gcaggcattg cacagtttca gaaggagatt acagcatgac tgagttttta gggatccaac    5580
agggacctgg gtagagattc tgtgggctct gaggcaactt gacctcagcc agatggtatt    5640
tgaataacct gctcttagag ggaaaacaga catagcaaac agagccacgt ttagtgatga    5700
aactctcact ttgcctgagt catgtgcggc catgcccagg ggtcaggctg acactcaact    5760
caaaaacaag tgagaaattg aagacaatcc gtggtggcag ctactggaag ggccaccaca    5820
tccccagaaa gagtggagct gctaaaaagc catttgtgat aggcacagtt atcttgaatg    5880 catgagcag agattacgga aaaatcgaga atgttaatga ggcaacattc gagttgagtc    5940
attcagtgtg ggaaacccag acgcttccat cccctaaaag gaacatcttg ctctcagtca    6000
aaatggaaat aaaaattggg gcttgaattt ggcaaatgat tcagaactct gtgtaggtat    6060
tttcacacgc acagtggata attttcatgt tggagtttat ttgtgctaaa aggcagaaaa    6120
gggtaaaaag cacatcttaa gagttatgag gttctacgaa taaaaataat gttacttaca    6180
gctattcctt aattagtacc cccttccacc tgtggtaatt tcctgagata gtcagtgggg    6240
aaaagatctc tccttctctt ctttctcccc ctcccctcct ctccctccct ccctccctcc    6300
ctccctcctc tccctcccct ccccttttcct tctttctttg ctccttctcc tctgcctcct    6360 tctcccttc ttcttcattt attctaagta gcttttaaca gcacaccaat tacctgtgta    6420
taacgggaaa acacaggctc aagcagctta gagaagattg atctgtgttc actagcgtgc    6480
aattcagagg tgggtgaaga taaaaggcaa acatttgagg ccatttcctt atttggcacg    6540
```

```
gcacttagga agtggaacat gcctaatcta ctggtttgta ccacctttcc ctataatgga      6600
ctgtttggga agctcctggg caaccgattc tggcatctca ttggtcagag gcctgttaaa      6660
tggtactctt atttgcaaag aaggctgtaa cttgtagctt taaaagcctc tcctcaagaa      6720
agaagggaga aaggatatgg ctagacatat ctaatagact taaccactgt gaaaagcctt      6780
agtatgaatc agatagaacc tatttttaac tcagttttga aaaaaataat ctttatattt      6840
atttgtgtgt gtgtgtgtgt gtgtgtgtgt gtgtgtgtgt gtgtgtgtgt gaaccacatg      6900
tagcaggtgc tggaggaggc cagaagaggg caccagatct cctggaactg acaccacaca      6960
tggttatgag ctgcctgatg tgggtgctgg gaactgaact ctcgtgttct gcaagagcag      7020
caactgttct cttaactgat gagccatctc tccagccccc cccataattt taattgttca      7080
ttttagtaaa ttttattcat aatcaattat cacagtataa acaatgatt ttatatatat      7140 catatacata tcaaggatga cagtgagggg gatatgtgtg tgtgtgtgtg tgtgtgtgtg      7200
tgtgtgtgtg tgtgttattt gtgtgtgtgc ttttaagaa ggtgccatag tcactgcatt      7260
tctctgaagg atttcaaagg aatgagacat gtctgtctgc caggaaccct atcttcctct      7320
ttgggaatct gacccaaatg aggtattctg aggaactgaa tgaagagctc aagtagcagt      7380
gtcttaaacc caaatgtgct gtctagagaa agtcaacgtc atcagtgagc tgaggagaga      7440
tttactgagc ggaagacaag cgctctttga tttaagtggc tcgaacagtc acggctgtgg      7500
agtggagcct gtgctcaggt ctgaggcagt cttgctagc cagctgtgat gagcagtgaa      7560
gaaagggtgg agatggaggc agggtgggag cagggctatg gttcagacta ggtatcgtga      7620
gcacaccagc tggttgactt gtggtctgtg ggtcaggcgt tgtaaacgcc ctcagggtca      7680
ggcagtcaca ttgcttgaag ctgaatgggt gaggcaacac agagagtgca aagaaggcaa      7740
agtaccacct cttccccgac ccaggtcact tctgggttat agctgagact ccggacagca      7800
tgcaaccagc tggttagagc ttcagggaaa acttgatgtc tgcatgttgc tatgaaatgt      7860
gattcggtac atctgagaa aatttataat gctggctcag tcaagcactg aacaaaggta      7920
ccttggcttt gggagctaca tgacattgac ttgtaggcag acttttttttt ttctgcccgc      7980 caattcccag ataaccaata tggaggctca atattaatta taaatgctcg gctgatagct      8040
caggcttgtt actagctaac tcttccaact taaatgaacc catttctatt atctacattc      8100
tgccacgtga ctttaccttg tacttcctgt ttcctctcct tgtctgactc tgcccttctg      8160
cttcccagag tccttagtct ggttctcctg cctaaccta tcctgcccag ctgctgacca      8220
agcatttata attaatatta agtctcccag tgagactctc atccagggag acttgggtg      8280 ctccccctc ctcattgcca tccgtgtctt cctcttccct cgcttccccc tcctcttcct      8340
gctcttcctc ctccaccct cctttcatag tattgatggc aagggtgttc tagaatggag      8400
gagtgcccat aggcatgcaa agaaaccagt taggatgctc tgtgagggt tgtaatcata      8460 agcgatggac acaattcaag ccacagagtg aagacggaag gatgcactgt gctctagagc      8520
aacttctggg gcagaatcac agggtgagtt tctgacttga gggcgaagag gccacgagga      8580
agggagtgag tttgtctgag ctagaagcta cggcccacct cttggtagca gacctgccca      8640
caagcatgct ttgttaatca tgtgggatct gattttcctc taaatctatg ttcaactctt      8700
aagaaaatgt gaattctcac attaaaattt agatatacgt cttttggtgg gggggtgta      8760 aaaaatcctc aagaatatgg atttctgggg gccggagaga tggctcagag gttaagagaa      8820
ctggttgctc ttctagacat tctgagttca attcccagca accacatggt ggctcacaac      8880
catctgtaat gcgacctggt gccatcttct gacatgcatg gatacatgca ggcagaaagc      8940
```

```
tgtatacata gtaaattgat aaatctttt  ttaaaaagag tatggattct gccgggtgtt   9000
ggtggcgcac gcctttaatc ccagcactct ggaggcagag gcaggtggat ctctgtgagt   9060
tcgagaccag cctggtctat aagagctagt tccaggacag cctccaaagc cacagagaaa   9120
ccctgtctcg aaaaccaaa  aaaaaaaaaa aaaaaaaaa  aaaaaaaga  gtatggattc   9180 taagaaagcc gtaacagctg gagctgtgta cggagttcag cgtggtacta aagaacagag   9240
cattcatgat gaaacacccc aggattttta cttagtatct agtttccatt gttgttttga   9300
gaccggctct tatgctctcc aggctggcct caaactgctg atcttcccgc ctctacctct   9360
caagtcctgg gactacttgg ctcataaaac agtttttgtc gggctccctg aagttatggt   9420
tgtacaaacc gtgggggtca atatactcac ttgggcagag agagaaggtc tgaatcccag   9480
acaatgactg catctcagga cagttgggaa gaggacaatg gcagaaggac ttagaaaaga   9540
tagactggag ggtggaaaag cagcaggaac agagaaacaa acaggaagc  ttgctatcca   9600 gggccactct ggagtcctgt ggcaagatgg aagcgggcta ggggaataca tttgtgctac   9660
tgtgtgtgtg tgtgtgtgtg tgtgtgtgtg tgtgtgtgat caatgcctat caatgttgaa   9720
ggggaaatat gtataccaca ttgattctgg gagcaattct cagtatctgg cctagagaaa   9780
ggaatggccc ctgcagaata gacagagtga atggtgccct ttatcatttg ctaaagtgaa   9840
ggagaaataa acatccttcc atagagtttc aggtaaatga accccacagt tcatctgtgc   9900
cgtggtggag gcctggccaa cagttaaaaa gattagacac ggacaaagtc tgaaggaaac   9960
acctcgaata ggaagaggag agccacctca ttctgtaact ttcctcaagg ggaagatgtt  10020
ccaagagtgg gaataaatgg tcaaggggg  gatttttaat taggaaaacg atttcctgta  10080
tcacttgtga aactggaggt tgatttgggg cataggacaa tagatttgat gctttgcaaa  10140
aagctgtttc aaagcagaga aatggaatag agacaattat gtagcgagga gggagggtgg  10200
ggcgaagatg gagacagaga agtggaagct gactttaggg aagaggaaca tagaccacag  10260
gggcggggcg ggggcaggg  gcgggggcg  gggctcaaag gaggcagtgg gaacgttgct  10320
agtgttcgca gcgtaagcgt gaatgtgcaa gcgtctttgt ggtgtgtgac caggagtagc  10380
gtggctggct tgtgtgctgc ttgtaatccc agtctttgag gtttcacac  tgttccacag  10440 tgggtgtgat tttccctcgg agagcatgag ggctctgctt tccccacatc ctccccagcg  10500
ttcgttggta tttgtttcca agatgttagt gggtgagaca aagcctctct gttgatttgc  10560
ctttaacagg tgacaaaaaa agctcaacca ggagacattt tgccttctt  ggaaggtaat  10620 gctcccatgt agagcaatgg gacccatctc taaggtgagg ctactcttgc agtttgcacc  10680
cagctcttct gatgcaggaa ggaagttggt gggcaagcaa gactgtttgc ttcttgcgat  10740
ggacacattc tgcacacaaa ggctcaggag gggagaaggc tgtttgatgt ttagcactca  10800
ggaaggcccc tgatgcatct gtgattagct gtctccatct gtggagcaga cacggactaa  10860
ctaaaaacca gtgttttaa  attgtcaagc ctttaaggtg aggaaattga cttattgtgc  10920
tgggccatac gtagagcaag tgctctgcat tgggccaacc cccggctctg gtttctaggc  10980
accagaatgg cctagaacta actcacaatc ctcccattcc aggtctcagg tgctagaatg  11040
aaccactata ccagcctgcc tgcctgccta cctgccttcc taaatttaa  atcatgggga  11100 gtagggagaa atacacttat cttagttagg gtttctattg ctgtgaagag acaccatgag  11160
catggcaact cttataaagg aaaacattta gttgggtggc agtttcagag gttttagtac  11220
attgtcatca tggctgggaa catgatggca tgcagacaga catggtgctg gagaaaggga  11280
```

```
tgagagtcct acatcttgca ggcaacagga cctcagctga gacactggct ggtaccctga   11340
gcataggaaa cctcacagcc caccctcaca gtgacatatt tccttcaaca aagccatacc   11400
tcctaatagt gccactccct atgagatgac agggccaatt acattcaaac tgctataaca   11460
ctttaaagta tttattttt attattgtaa attatgtatg tagctgggtg gtggcagccg    11520
aggtgcacgc ctttaatccc agcacttggg aggcagaggc agatggatct ctgtgagttc   11580
aagaccagcc tggtctataa gagctagttg caaggaagga tatacaaaga acagttctag   11640
gatagccttc aaagccacag agaagtgctg tcttgaaaac caaaaattgt gctgggacct   11700
gtctctgctt tggttgcttc ccactcccc agagctggac tcttggtcaa cactgaatca    11760
gctgcaaaat aaactcctgg attcctctct tgtaacagga gcccgaagtc aggcgcccac   11820
ttgtcttctc gcaggattgc catagacttt ttctgtgtgc ccaccattcc agactgaagt   11880
agagatggca gtggcagaga ctgggaaggc tgcaacgaaa acaggaagtt attgcaccct   11940
gggaatagtc tggaaatgaa gcttcaaaac ttgcttcatg ttcagttgta cacagactca   12000
ctcccaggtt gactcacacg tgtaaatatt cctgactatg tctgcactgc ttttatctga   12060
tgcttccttc ccaaaatgcc aagtgtacaa ggtgagggaa tcacccttgg attcagagcc   12120
cagggtcgtc ctccttaacc tggacttgtc tttctccggc agcctctgac accctcccc    12180
ccatttctc tatcagaagg tctgagcaga gttgggcac gctcatgtcc tgatacactc     12240
cttgtcttcc tgaagatcta acttctgacc cagaaagatg gctaaggtgg tgaagtgttt   12300
gacatgaaga cttggtctta agaactggag caggggaaaa aagtcggatg tggcagcatg   12360
tacccgaaat cccagaactg gggaggtaga acggatgag tgcccggggc tagctggctg    12420
ctcagccagc ctagctgaat tgccaaattc caactcctat tgaaaaacct ttaccaaaca   12480
aacaaacaaa caataataa caacaacaac acaacaaac taccccatac aagtgggcg      12540
gctcttggct cttgaggaat gactcaccca aacccaaagc ttgccacagc tgttctctgg   12600
cctaaatggg gtggggtgg ggcagagaca gagacagaga gagacatgac ttcctgggct    12660
gggctgtgtg ctctaggcca ccaggaactt tcctgtcttg ctctctgtct ggcacagcca   12720
gagcaccagc acccagcagg tgcacacacc tccctccgtg cttcttgagc aaacacaggt   12780
gccttggtct gtctattgaa ccggagtaag ttcttgcaga tgtatgcatg gaaacaacat   12840
tgtcctggtt ttatttctac tgttgtgata aaaaccgggg aactccagga agcagctgag   12900
gcagaggcaa atgcaaggaa tgctgcctcc tagcttgctc cccatggctt gccgggcctg   12960
ctttctgcaa gcccttctct ccccattggc atgcctgaca tgaacagcgt ttgaaatgct   13020
ctcaaatgtc actttcaaag aaggcttctc tgatcttgct aactaaatca gaccatgttt   13080
caccgtgcat tatctttctg ctgtctgtct gtctgtctgt ctgtctatct gtctatcatc   13140
tatcaatcat ctatctatct atcttctatt tatctaccta tcattcaatc atctatcttc   13200
taactagtta tcatttattt atttgtttac ttactttttt tatttgagac agtatttctc   13260
tgagtgacag ccttggctgt cctggaaccc attctgtaac caggctgtcc tcaaactcac   13320
agagatccaa ctgcctctgc ctctctggtg ctggggttaa agacgtgcac caccaacgcc   13380
ccgctctatc atctatttat gtacttatta ttcagtcatt atctatcctc taactatcca   13440
tcatctgtct atccatcatc tatctatcta tctatctatc tatctatcta tctatcatcc   13500
atctataatc aattg                                                    13515
```

<210> SEQ ID NO 6
<211> LENGTH: 14553

<212> TYPE: DNA
<213> ORGANISM: Mus musculus

<400> SEQUENCE: 6

| | | | | | |
|---|---|---|---|---|---|
| cttgaagaac | acatgttttc | caagagggag | cacccatgtt | ggaatgacaa | tgtagttagt | 60 |
| gctcctctcc | tgtaggttag | tgctcctttg | ctataggtaa | gtgctcctct | cctataggtc | 120 |
| agtgctcctc | tcctataggt | tagtgctcct | ctcctatagg | ttagtgctcc | tctcctacag | 180 |
| gttagtgctc | ctctgctcta | ggttagtcct | gctctcctat | agtacctaga | gagctagggc | 240 |
| aaatgggcta | ggcccgaagt | gcagagacaa | acagctatgg | aagactgggt | aagcacttcc | 300 |
| aagctacgaa | agagcagtgt | gaaggtcag | ggcttgtgca | gttagtaggg | gagatcttcc | 360 |
| agttgaagaa | acagaagaac | tgagagccac | tgggtatcat | cctcctgcgc | catgccttcc | 420 |
| tggatactgc | catgctccca | ccttgatgat | aatggaatga | acctctgaac | ctgtaagcca | 480 |
| gccccaatga | aatattgttt | ttatgagagt | tgccttggtc | atgctgtctg | ttcacagcag | 540 |
| taaaaccta | aataaggcag | aagttggtac | cagtattgct | gtgatagacc | tgaccatgct | 600 |
| ttcctttgaa | agaatgtgga | tttggtgact | ttggatttgc | aacacagtgg | aatgctttaa | 660 |
| atggagatta | atgggtcatc | aattcctagt | aggaatatgg | aagactttgt | tgctgggagt | 720 |
| atttgaactg | tgttgacctg | gcctaagaga | tttcaaagga | gaagaatttc | agaatgtggc | 780 |
| ataaagacag | ttttttgtggt | attttggtga | agaatgtggc | tacttttttgc | ccttgtctga | 840 |
| aaagtctgcc | tgagactaaa | gtgaagagaa | tcagattaat | tgcattgaca | agggaagttt | 900 |
| gtggctgcgc | tatctggaaa | cttacagcca | gcctcttgga | cctcgggtga | cttacgcaaa | 960 |
| tactcaggga | cagagatgct | tgactctgta | ctgatgagtt | gtcttggatg | caaatatggg | 1020 |
| ctcttcattt | gactacatgt | cacgatgagt | caggagctgc | tctctccaga | gtgtgacaaa | 1080 |
| gcgaggggat | gctgacggta | gctgttctag | cttgaaggt | aagcctgcac | ttatgctaaa | 1140 |
| gtcacacata | cacgagccgg | gtggagaacc | tgtctgtgtg | gagacacctt | tcattacctg | 1200 |
| tggcatccag | cctctcaagc | ttggactgcc | tgtgtgctcc | tggactctgg | aggtcccact | 1260 |
| gctctgtcct | ctgctgctta | tgatactgac | attttaaaag | aatccagtgg | ttccccctg | 1320 |
| tactcggtgt | ctacttctac | ctggatgttc | ctcatttatg | ttctgtgaca | cttctctgtg | 1380 |
| actctgctgc | attcctgggt | gacatgtgga | caccctgtcc | ctttgcagac | catgatgtca | 1440 |
| ctgtcactag | tggaatcaga | tgccccaagt | gttgtcctgt | gtttgggaac | gtgacaggca | 1500 |
| gtacagaagc | agaagaggaa | gggtgaaaac | ggaaatgtca | cagcagcatc | tgatgtgtgc | 1560 |
| ctcagtcacg | catgctgctg | attgaaacta | ctcagcatga | gagagggcca | tggtgaatac | 1620 |
| acaaccctat | acacactgtg | tccatttctc | tctctctctt | acacagagag | agagggagga | 1680 |
| ggggagggg | gaggcggagg | gggaggggga | gggagaggga | gtgggagagg | gagagggaga | 1740 |
| gggagaggga | gagggagagg | gagagggaga | gggagagttt | aatgtctgtg | aagagatacc | 1800 |
| atgaccaaag | caactcttat | aaaggacaac | atttaattgg | ggctggctta | caggttcaga | 1860 |
| aattcagtcc | attctcacca | tggtgggaag | catgcaggta | gatgtggtgc | tggaggaacc | 1920 |
| aagagttcta | tatcctgatc | tgaaggcagc | caggagaaga | ctgcctcttc | tgcacagggc | 1980 |
| agagcttgag | catagaacat | caaagccctt | ccccacactt | cctccaacaa | ggtcatacat | 2040 |
| acttcaacaa | agacacacct | cctaacggtg | ccactccctg | tggaccaacc | atttaaacgc | 2100 |
| atgagtctat | gagggtcaaa | gctcttcaaa | ccaccacact | catgtacaca | cacacacaca | 2160 |
| cacacacaca | ctctcataca | cacacacaca | cacactcaca | cacacacaca | cacacacaca | 2220 |

```
cacacacaca ccacacacac acacacacac agagttctat tttgcactgt tcactgtca    2280
caaggttcta cttatctcag acacactgcc aggaattgtg tgggaagact ttcagtttct    2340
ttgggttcac atggacttag cagttcttgg tgatcctgaa agatttctgc agaaagaagc    2400
caaagtgttg agcccaaggc ctggccacac attagtcctg tctagatgaa caggggttta    2460
aaaataaggg ggcatcaagg tgaagccagc aggggctgac ttagagagga gacccaccca    2520
agccaactgc tcgaagtcaa aagcgatgaa tccccatatc cagctgtgcc cggtgctgtc    2580
ttgctacatc tttagtaaat gttcttttag ttgtatgcgt atgaatattt tgcttgcata    2640
tatttgtgta caccataggt gttcctaggc cctatggagg ccagaagagg gcatcagatc    2700
ctttggaact ggaattatag acacttgtta cccatagagt agattgtggg aaatgagcct    2760
ttagtcttcg agagcggcca gtgctcttaa ccttttggtcg tttctccagg tctttgagac    2820
tttatttttct tggacatcag gacaggatcc agggctttga gcttgtttct tcagccagct    2880
ttcttttcat gtatattaaa ttttatgtta ttttgctttc tttttcccca agacagaatc    2940
acactctata tagctcaggc tgggtttgaa ttcagtttcc ctgtctcagt ctaccgggta    3000
atatgattac agatgtgagt ctgacttttgg tatcaaagtc cccagcccctt ctggatatgt    3060
gttttaagga tatcagatat atccttgatt tgctttgaat tttcttttta gttacaacat    3120
aattagttcc gtgtcacctg aatatgtgta tgtcacctac atagtcttcc ttcttctctt    3180
cttccctctc ccaccttccc aggtacctgt ctgtcttcat atccttgtgc tgagagtctt    3240
gttgagggag atgatgaccg agacagagcc actggggaag ggagatgggc tagtgcaggt    3300
cttcagagag gagctcgtga atattgtagc ccctttagtc cctggcatgt cctcttgtat    3360
agccaccgcc atgctgtggc ctggcagaag tgaataagtt gtccagctgt tgacaggcct    3420
gccctccaga cccagtctga tcccaagaaa gggcatctgt gtctgtctct gaggccgtaa    3480
gtgctgcctg gttgtctcca gcttgacttg acactccctc cttaataaga gtaccacaga    3540
acagggtctg cagagtccct gggccaggtc cctgtgctgt cctggaatgc caggcgtgaa    3600
tttcctgtga agtaggactt tgctcgccaa gctcccacgg cttgcccttc agatagccag    3660
aattatctgg taccctgcat tgccgttcaa tacgcagagt atcactggaa gcgcgcgcgc    3720
gcacacacac acacacacac acacacacac acacacacac acacgcccac tccatcttta    3780
aaccccaccc cccagcaacg gcggtgtaaa cactctccat caggaagctg aaacgcagtt    3840
gccctctgct ggggagatga aggcagcttg ctggggggcga ggaccgtgct agcaaccttc    3900
cctggtgcac acgggctctg gtgcatgacg ggaacggaaa cgcggaacta aagtcagtcc    3960
tgctttttt tttttttttt tttttttttt tttttttttt ttttttttt ggcgttggtg    4020
gtggactgag tgacaatcag tgaaatcact taggttgttt ttctcttctt cgttgggttt    4080
gatagacggt gggagagggt cagaggagaa ggggagggat ggggagagag ggaggaggga    4140
ggggcgggag gcgggggggcg aggaaaaacgt gctaacttct ccaatcctac aagacaaagg    4200
tttgagaaa gccgcactga gtgacccagc agaaggaatc caggaatgtc cgctggaatc    4260
tgactgttga ttccagcgcc atgcagagaa tctaggctgg taggaacatt ctttgtccta    4320
tccgacataa taactccaac caacacgaaa agaaaggct atacaagtga agaaatggca    4380
ttttcacttt catgactata caatcacttc caggtagtaa cacgtgtcta gcacagcggt    4440
tctcaacctg ggggtcacga tcccccactt ttctgcatat cagacatttt tacgttgtta    4500
ttcataacag tagcaaaatt gcagctatga agtaacaatg aaatgcattt atggtgcgtg    4560
tgtgtgtgtg tggggggggta tcaccttaac atttactgta agaaggttga gaatactgct    4620
```

```
ccagcagcta gtgtgttgga cttaggttct gggtatatta ttagcaatag ccaaccagaa    4680
tccccaccca ccacagcatt gaggccccat gcagggcttg ctgggagagg cactgataag    4740
acttctttat gtatttattt agagacgaat actcattagg taggccaagc tagcgtcaaa    4800
ctcatggcaa ttctcctcct ccagtttcct aagtactgga ctcaggagtg tgttgccatc    4860
atatacagta aggatttatt gactgaagaa aatctcaagt ggctttggtt aatccctact    4920
acgccagagg ctgaggcagg aggcgcgcaa ggtcaaggct tgcctgggct acatatagag    4980
tgagctcaat tttgacactt ggtgcggtgt tagtagtaat agtaaagatg aaggtgtggc    5040
tcaggtgggg ccggtgattg gacacacttg gggtctcctg gtccatctgc agctgtgcaa    5100
caggaagagc ggagaatgag aggaaagaga gaaaagacag aatgagagag agggaggaag    5160
agagaaaaag gaaagagag aggaaaggaa aaggaaaat gaggaaagcg agaaagaaga    5220
aatgagaaag aggaaaggga gaaagaaatg agagagagaa aagaaaagac agaatgcgag    5280
agagggagga gagagaaaa aggaaaagag agggaaagg aaaaggaaa atgaggaaag    5340 cgagaaagaa gaaatgagaa agaggaaagg gagaaagaaa tgagagagag aaaagaaaag    5400
acagaatgcg agagagggag gaagagagaa aaaggaaaag agagaggaag ggaaaaagga    5460
aaatgaggaa agcgagaaag aagaaatgag aaagaggaaa gggagaaaga aatgagagag    5520 agaaagaaa agacagaatg cgagagaggg aggaagagag aaaaaggaaa agagagagga    5580
agggaaaaag gaaaatgagg aaagcgagaa agaagaaatg agaaagagga aagggagaaa    5640
gaaatgagag agagaaaaga aaagacagaa tgcgagagag gaggaagag agaaaaagga    5700 aaagagagag gaagggaaaa tggaaaatga ggaaagcgag aaagaagaaa tgagaaagag    5760
gaaagggaga agaaatgag cgagataaaa gacagaattt gagagaggga ggaagaaata    5820
ggaaaagaga ggaaaggatg gagaaaagag agaaagaaag agagatgaaa gagagaaagg    5880
agaaatgaaa tgagagagag agagagacac aaagagccag agagagaaga aaaaggggga    5940
aagagaaaga gaaagaggaa ggctcctctt ggacacatct tcctttatct ttccctgggg    6000
accgccaaag cctggtggca tactgtacat tctgtacact gttcattcaa acaggctct    6060 gtcttaaaga tggtctgagc ggtcagaaaa gggtattgtt aacttgtttg caaaactgcc    6120
tcaggagagt gctgagtgcg tgaaagttgc tgcccgttaa ggagaagtct ctactacttg    6180
tgatctcacc atcgaaaatt tctttaattg tctcctggtg ttctgggttt tgcagttttg    6240
tttctaagga tacattcttg ggtgatgtca caaagtcccc aaagacacgg tggagctgtg    6300
ttagatgggg aaagacagtc tgctgaggat ttatctggaa ctgtcagaag gaaagaagg    6360 taaatggggc acttgggaaa gtggcctcta gtttgacttc tggcttagca aaggttgtgg    6420
ggagataagc atacacagt agttagcagg aggcaacagg gtcctgggag gacgcgaggc    6480
agaaggagag gctgggctga cagcatgcaa tcattgcata gtctccaaag gagattgcaa    6540
catggctgag ttttcagagg tcctacagag cccgtggtag agattctgtg ggttctgaga    6600
caacttgact ttagccagat ggtatttgag taatctggga gagagaaaac agctacagca    6660
aacagggcca catttagtga cgaaactctc actttgactg ttgagtcatt tgcagtgggc    6720
cctgaggtca ggctggccct cagctcaaaa acaagcgagg aactgaagca attactcaga    6780
taatccacag ccacagccac tggaaagggc cacatcccca gagacagcac agcaggggtg    6840
ggggtggggc tatgagaaag ttagtgattg tagcagttat ctagaatgtg cggagcagag    6900
gaggttacac aaaaacctag aatgtcattc aatgtgggaa accgagaggc tcccaagccc    6960
```

```
taaaaggaac agtttgcttt cagccaaaat ggaaataaaa tttggggctt aaatctggca    7020
aatgattcag accttctgtg taggtgtctt taaatgcaca gcagattgat tttcatgttg    7080
gagtttattt gaactaaaag acagaaatgg tgaaaagcac acctgaagaa attgagatgc    7140
tatgaataaa atcatttact tacagctatc acttaattag tacctccttc caccttgctg    7200
atttattggg ctagtcaagg aagaaaagat cttccctcct ccttctctcc tcctcccct    7260 cctctcctcc tcccctcccc tccttgacct tcctctcctc cttttccctc ctccccctct    7320
tcttctcttc accccctcct cccctcccct cctctgtact cctcccctt cctcccaatc     7380 tcttttttct ccccttctt ctctttctcc ccctcctct tccctcctct tcctccctcc      7440
ctccctcctc ctcctcatcc tcctcttcct cttcatcctc ttctccttcc tccctctcct    7500
cctcctcctt ttccagccct acctaccttc cctttcttct tcatttattc aaagtagctt    7560
tgaacagcac tactcggttt agttgtgtat aaaaggaaaa tgcaggtcca agcagcttgg    7620
ggaagattgc tttttgctct ctggaggcag atgatgacag ttcaagatca ttccttttgc    7680
tccatgtcac aggaaggggg acatgccgaa tctaccagtt tgcagccacc tacacaggat    7740
ccaccttcac ttctaaggaa atgtttggga agctacctac caaccacttc tggcatctca    7800
tgggctagag gactcttaaa tggcactctt atttgtttaa taaaggaggt tgtgacgtgt    7860
agttttaaat cccttccaca caacaattgc tactctctga ccaaaaaga agggagacag     7920 gatacggcta ggtgtctagt agactttacc actttgaaaa gccttaatat aaatcaggta    7980
gatacatctt tttaacttat tcttgtaaag acaaaaacaa aactttattt ttatttgtgt    8040
gtatgcttgt gtgtgtgtgc ctgtgtgtat accacatgtc gctggtgccg agaacacca     8100 gaagagggga cctgatctcc tggagctaaa gctatccatg gttctgagct gcctgatgtg    8160
ggtgctggga acagaactct ggtcttctgc aagagcaaca agcctcctct taactacgaa    8220
tctcctcccc atcccccaa atacatttaa ttattcattt tagcagcttt atttcgtaac      8280
tacttatcac agcataaaac aaggatttta tatatattac atgcaatcga ggataagagt    8340
tgaggggaga tgcgtgtgct ccttctgggt gtctgtgctt ttgaagaatg taagcagtgc    8400
acaagggacc gaggcgtgcc tgtctgccag gagctgtctt cttcccttgg actctgagct    8460
gagtgcagtg ctccgaagaa gtaaaagacg acctcatgaa gcaatgtctt caacccaaac    8520
atgctgtcca gacaaagtcc agcttcatta gtgctctgag gagagactta ctgagcctca    8580
ggaaagcccc cctcagcatg gcgaaagtcc actttgattg aagtgactcg aaagccatgg    8640
cagtgcggcg gcgccgcgt ggagcttgtg ctcgagtcgg aagcggcatc tttgtcaggc     8700
ggctgtgatt agcacgggga ggcaggactg gagtgaagga agagttgggg gcggggctta    8760
gcgctctggt ctcctaagct gtagtcagcg cctcaagatt tgtaacctgc cttctgcctt    8820
cccagccagg cagtcaagtg gctccaagct gaagactgca aagtgcccct aaccttttgg    8880
ttatagcgag gctgaagaca ccgtgctctt tcatgaaagc cggatgtctg aaatccgatt    8940
tgataaatat ggataaaacg tataacgctc gatcaatcga atcgaaggag ctcacgattg    9000
gcaccacggc tttggggaca acagagtact gactcgttgg gaggacttgg atacttcccc    9060
tcctcttcca tctcttcccc tttcctcact tcctcctcct tccttctcca ttttctccct    9120
cttcactgtt tcttactatt tttacaaaag attttattta tttatttatt tatttattta    9180
tttatttatt tatttattta tttatttaat gtatgcgagt acactgtagc tgtcttcaga    9240
cacaccagaa gagggcgtca agttccatta gagatggttt cgagccacca tgtgttgct    9300 ggggcctctg gaaggaccgc cagtgctctt aaccctgag ccatttctcc agtacccttc     9360
```

```
tcaccgtttc tcttcaatct tcttcctctt ccttctccac tttccttgtc ttcttggttt    9420
cattatcttt ctcccttcct tcctcttctc cccttcttcc tcctccactg tagttttcct    9480
tccctactct tttcctgcct ccctcctcct ccctctcat tcccctcct ctttcctcct      9540 tctccctcct cctccttcct tctccctctc ccctctcccc tctcccttct ccttctccc     9600 cctcctcttc ctctttctcc ttctccaccc ctcctgtcac agtatcaatg gcaagggtgt    9660
tctagaatgg aggagtgtcc cctaggcact aacgaaagcc agttaggatg ctctgagacg    9720
ggtacaattc agggagggcc gtgggatgg aaggggttgtg ctgcgattca ttctggagca    9780 accccaggc agaatcatga ggttggttcc ggattcgcag ggcacaattc agaagaggaa     9840
ggtttcagga aggacgagtt tgtctgagat aggagttaca tctgatgtct tggcagcaga    9900
gccactgtac aagcgtgctt tattaaccac gtgggattaa atcttctttt aaatttattt    9960
tcaactctta aggaaacgtg aactttcaca ttcaaattta gacttgcagc tcttatgggg    10020 aaaaaaggg atcttaaga atattaagca taggcggctg gagagatggc tcagcggtta     10080
agagcactct ctgctctccc agaggtcctg agttcaattc ctagcaacca cataatagtt    10140
aacaacagtc tttaatgaat tctaatgccc tcttctggtg tgtctgaaga cagttacagt    10200
gtactcatat aaataaaata aagaaattta aaaaatgaa tattaggcat agattcctgg     10260
atcctaagaa agccatcaga gctggagcca tgtgtgggat cctgcttggt gctggagggg    10320
cagagttcat gccccgggg ttttactta ttatcacatt ttcatcgttg ttttgaaaca      10380
gggtcttgtg tggtccaggc tggccttgaa ctcatctttc agcctctacc tcacaggttc    10440
tgggattact tggttcctaa aagtatctcc gtcaagctcc ctggtgttat ggctgtgcca    10500
accaggaggg tctatacact cgctcaggta gagggagaag atccgaatct ctgacaggga    10560
ctgctgcctc tcgggcaaa tggagtgaag gacagcggca gaaggattta ggaaagatgg     10620
acgggagagt ggaaatgctg cagaagccag aaaacaaagc aggaagcctg ctgtccagtg    10680
gggctcaaga gcggagggat gcgaggggc tgcgcaggaa catttagcgt ctgcgtctat     10740
gggggtaggg gcggggtgcc agcacctagt cacctgaagg ggaaatgctt gcccagggag    10800
caggtctcag tagctgacct agagaaagga gcggccccta cagaggagac acgggtcact    10860
gtttgttaaa gtgaaggaga aataaatatt ctttcaaaga atcttaggtg agcccagttc    10920
atctgcgctg tggaggcctg gggaacagtt aaaaagaccc tgacacacac ccaaggcaaa    10980
caagcaacac acggctcctt ccgtaagggt ccatgattct ctgaagaatc agccccggaa    11040
tcagccccgg aatcaggtag tccgtaaaca caatgagtgt tttactctgc agaagtccag    11100
cctgctggcg tctcccatta ccaaaataga gggatagtca cgtgagctca ccggctcgat    11160
ttaaggcacg tggttttcca gggtagatga gctttggctt ctggaaccat tatggggcac    11220
gaaggatgga gccaggattt tttttttttt tttttttttc tattagcaat tgatttgctt    11280
gggcttggct ggacttgccc agttcttagg cccagtcttc ttaactgccg atctgaagtc    11340
tgtcatggag tcagcctagc cttctcactt cccttcagct cgaataggaa gaggaggtgc    11400
acaccagatg gtctgagagc agggataaat ggtgtgcctt tgtctttcag tatttcgtta    11460
ttttaagtag gaagatgctt ttctgtatta cattgcttgt gaaaccggaa gttgattcgg    11520
ggcacaggac aatggatttg gtgtttgca aggactgttt cagaagagag aggagtggaa     11580
gggtggttag agtgaggagt ggggtgggac gggatggggg aagagaagga agggccagac    11640
aggctaggta gggctgagag gaggcggtgg gaacttcttg agttagcgca gcagtaaact    11700
```

```
tggatgtgcg tgtatctttg tgatatatga cccggagccg tgtagctggc tccgatagta    11760
ctgctaatgt cagtgtcggg gggggggggt cccatactgt tccacagggg ctgcacattc    11820
ccatcgagag caggagggct cctctctcca tacatcctcg ccagcattcc ttgttgtttc    11880
tgtgatgaca gggggtggga tgaaatctct ctgttggttt gagagaccgt gaagaagctc    11940
aaccccagga cattttgcag tcttggaagg cagtgcctcc atgtggagcc gtggagccca    12000
tctctgagtc caggtcactc ttgcagttcg cactcagctc ttcagatgca ggagagacgt    12060
tggtgggaaa gcaagattgt ttgcttgttg agatagacac attctccaca caaaggctca    12120
cgtgggggcaa aggctgattg acgtacagcg ttcaggaacg cctgtggtag agctatgatt    12180
agctgtctcc atctatgaag cagacaaaga gttataaaaa aaatcaatgt tttcaaattg    12240
tcaaactttt aacccgacag caagcgctct gtccctgggc taatcccctag ccctggtttc    12300
ttgagatggg gtcttttgtg cactagactg gcctagaact cacgatctta gtgttccagc    12360
ctcccagctg ctgggatgag ccgctataac cagtctgcct gccttcctaa attttaagtg    12420
atgggaagtg ggggagaata cagtttaaag tatgcagatc tgagagcagg aacctggcaa    12480
agccaagggg ccggagttac aggcggctaa catgggtgct gggaactgac ccaggtcctt    12540
gagaggagca gtgtgtactc ttgaccaaac aggtccgtct ctccagtccc cgtagtatta    12600
aaaataggta ctacgggcat ggtggtgcac acctttaatc ccagcactag ggaggcagag    12660
gcaggtggat ttctgagttt gaggccagcc tggtctacaa aatgagttcc aggacagcca    12720
cggctataca gagaaaccct gtcttgaaaa caaaacaaca acaaaatagg tactacaaag    12780
cgatgtaatt gtgctcaaac atgcaaaccg aggggactgt atgcataaga aagagaaaga    12840
cggccacact ggttctatct gggtgacagg aaatcagtat ttttattttt cacattcatt    12900
tttttgttgt tgttgttgac acagtgattt ttctatcaaa acattatttt cttttatagt    12960
tcccctgagg agctgttttt aaagccgtgc tttgaaaaac cattgaagga gcagaggcag    13020
ggagactcct gtgtggcagt cggtgaagca ggccctctgc aggcaggctg gccctggact    13080
tgggagtctc tttccctccc tcctgtgctc aaatagcaaa tgtcaggctt caatgtagct    13140
agaaggttct agaatgatta agtttccaag gctgaagagc ttccctgttt gcctttcact    13200
tccctggaga ggtcgttgtg tgttccggag tctgcaaggt gcctttggtg atgcgggtgg    13260
ttcatctcgg gagattccgc ctggaggacc caagttcaag ccctgcctga gctacagagt    13320
gactttcagg tcttctgcgc aattcagtga gacccagtct acaaataaaa agtaaaaaga    13380
aggctgtgga tggaactcgg tggtagagtt ctgggtttac tccctagagg aggggagaag    13440
gaggaggagg gaggaggaag aggaagaaag aagaagagaa gggaagagga gaaggaaggg    13500
agggaagggg ctgacaagaa gagagaagag ggagggaggg gagggaaagg aaggggaaag    13560
gaagggaggg aaggggctga caagaagaga gaagagggag ggaggggagg gaaaggaagg    13620
ggaaagaaga gaagggtaag aagaaactgt tccaatggtc tggccacacag agtgatggcc    13680
ttttgtggtg atcagctgta atccttgatt tgacacaacc tagaatctgg gaagcgagtt    13740
tctgtgaagg agcattcaca ctggctggcc tgtgggcgtg catgtgggag actgtcataa    13800
ttaggttcat taatacagga agtcccagcc cactacaaat ggcttcgttc catacccaag    13860
agatgctaac tgtagacggt tggagaaagc aagcaagctg tggataccccc acgctctttc    13920
acctcggctc ctggggggtg ggtgcactgt gtctcttggt attttaaagt cctgccttga    13980
cgtccctgct gtgacagact gtaactggaa ttgtgagctt tagtccttta gttttctacg    14040
ttggtttttc tcaggatatt ttatcgcagt aacagaaaca agaccaggac acttgatctc    14100
```

```
ctctgatcaa cactgaagag ttacaaaaca ggctgaggaa acaaactttc ttctccctct   14160
cccccttctg tccctcccct tccttctcgc tccctcccct gccccctctc tccctgtctc   14220
tgtctctgtc tctgtctctg tctctgtctc tgtctctgcc tctccctcc cctccctcc    14280 ctctgtctct gtctctgtct ctgtctctgt ctctgtctct gtctctgtcc ctttctcctc   14340
tatctcctaa atggctggag gccatgctag ctcaatgttg aactttgaac acgtatttag   14400
gaaatctttg ttcttaacag ttctgaagtg ctgaagtggt ggtttagtct ctcggcctga   14460
caagctcact tcctctcact ctgtcttaat gaccaaatct gccatttccc taaaacagca   14520
caggctccag ctccaggttg ctccggagcg gag                                14553

<210> SEQ ID NO 7
<211> LENGTH: 34
<212> TYPE: DNA
<213> ORGANISM: Artificial sequence
<220> FEATURE:
<223> OTHER INFORMATION: synthetic

<400> SEQUENCE: 7
ataacttcgt ataatgtatg ctatacgaag ttgt                               34

<210> SEQ ID NO 8
<211> LENGTH: 34
<212> TYPE: DNA
<213> ORGANISM: Artificial sequence
<220> FEATURE:
<223> OTHER INFORMATION: synthetic

<400> SEQUENCE: 8
ataacttcgt ataatgtata ctatacgaag ttag                               34

<210> SEQ ID NO 9
<211> LENGTH: 60
<212> TYPE: DNA
<213> ORGANISM: Artificial sequence
<220> FEATURE:
<223> OTHER INFORMATION: synthetic

<400> SEQUENCE: 9
agattctgtg ggctctgagg caacttgacc tcagccagat ggtatttgaa taacctgctc   60

<210> SEQ ID NO 10
<211> LENGTH: 54
<212> TYPE: DNA
<213> ORGANISM: Rattus norvegicus

<400> SEQUENCE: 10
agattctgtg ggttctgaga caacttgact tcagccagat ggcatttgaa taac         54

<210> SEQ ID NO 11
<211> LENGTH: 59
<212> TYPE: DNA
<213> ORGANISM: Mus musculus

<400> SEQUENCE: 11
agattctgtg ggttctgaga caacttgact ttagccagat ggtatttgag taatctggg    59

<210> SEQ ID NO 12
<211> LENGTH: 59
```

<212> TYPE: DNA
<213> ORGANISM: Homo sapiens

<400> SEQUENCE: 12
agattcagtg ggctttggga cagcttgact tcaactagat ggtatttgaa taatctgct        59

<210> SEQ ID NO 13
<211> LENGTH: 624
<212> TYPE: DNA
<213> ORGANISM: Artificial sequence
<220> FEATURE:
<223> OTHER INFORMATION: synthetic

<400> SEQUENCE: 13
ttcttgagtt ccgccaacgc ctagtgacat cctgtgcaca ccctaaggtg gcctttgtgt        60
ggcactggct tgggtggtcg ggaaaggcat tttcagcttg ttgcagaact gccacagtag       120
catgctgggt ccgtgaaagt ttctgcccgt taacaagaag tctctactac ttgtgacctc       180
accagtgaaa atttctttaa ttgtctcctg gtgttctggg ttttgcattt ttgtttctta       240
aggatacatt cctgggtgat gtcatgaagt ccccaaagac acagtggggc tgtgttggat       300
tgggaaagat gatttatctg gggtgtcaaa aggaaaagaa gggaaacagg cacttgggaa       360
aatgtcctcc cgcccacccg aattttggct tggcaaccgt ggtggaggag caagaaacac       420
gtggacgttt gaggaggcat ggggtcctag gaggacagga agcagaagga gagagctggg       480
ctgacagcct gcaggcattg cacagtttca gaaggagatt acagcatgac tgagttttta       540
gggatccaac agggacctgg gtagagattc tgtgggctct gaggcaactt gacctcagcc       600
agatggtatt tgaataacct gctc                                               624

<210> SEQ ID NO 14
<211> LENGTH: 665
<212> TYPE: DNA
<213> ORGANISM: Rattus norvegicus

<400> SEQUENCE: 14
tttatctttc cctggggaca gccaaagcct ggtggcatcc tctgtgaagt gttcattcaa        60
gacaggctct gtcttaaagg tggccttcgc atggcgctgg cactggccgg ggcagtcagg       120
agagggtatt tttagcttct ttgcagaatg gcctcaggag cgtgctgagt ctgtgaaagt       180
tgctgccagt taaggagaag tctctaccac tcgtgacctc accattgaaa atttctttaa       240
ttgtctcctc gtgttctggg cttttgcagtt ttgttcctaa ggatacattc ttgggtgatg       300
tcacgaagtc cccaaagaca cagtggggct gtgttagatc gggacagaca atattgctga       360
ggatttatct gaaggtgtca aaggagaag aagggaaaca gggcactcag ggaaatggcc       420
tctagtctga gttctggctc agcaacagag gtggggagat aaggcacaca cagtggttag       480
aaggagtcat cagggttctg ggaggacagg aggcaggaga ggcagggctg acagtgtgca       540
atcattgtgt agtctcccaa ggagattaca acatggctga attttcaggg gtccaacgga       600
gactgtagtg gagattctgt gggttctgag acaacttgac ttcagccaga tggcatttga       660
ataac                                                                    665

<210> SEQ ID NO 15
<211> LENGTH: 655
<212> TYPE: DNA
<213> ORGANISM: Mus musculus

<400> SEQUENCE: 15

```
tttatctttc ctgggggacc gccaaagcct ggtggcatac tgtacattct gtacactgtt      60
cattcaaaac aggctctgtc ttaaagatgg tctgagcgt cagaaaaggg tattgttaac      120
ttgtttgcaa aactgcctca ggagagtgct gagtgcgtga agttgctgc ccgttaagga      180 gaagtctcta ctacttgtga tctcaccatc gaaaatttct ttaattgtct cctggtgttc      240
tgggttttgc agttttgttt ctaaggatac attcttgggt gatgtcacaa agtccccaaa      300
gacacggtgg agctgtgtta gatggggaaa gacagtctgc tgaggattta tctggaactg      360
tcagaaggaa aagaaggtaa atggggcact gggaaagtg gcctctagtt tgacttctgg      420
cttagcaaag gttgtgggga gataaggcat acacagtagt tagcaggagg caacaggtcc      480
tgggaggacg cgaggcagaa ggagaggctg ggctgacagc atgcaatcat tgcatagtct      540
ccaaaggaga ttgcaacatg gctgagtttt cagaggtcct acagagcccg tgtagagat      600 tctgtgggtt ctgagacaac ttgactttag ccagatggta tttgagtaat ctggg          655
```

<210> SEQ ID NO 16  
<211> LENGTH: 706  
<212> TYPE: DNA  
<213> ORGANISM: Homo sapiens

<400> SEQUENCE: 16

```
agaaacacaa cttctcccag ggagagtcaa gagagcagtg tcatttccta taaaatgtcc      60
aaggccaatc ccaggtcccg tgtcagccc ttgcgtgtgg cactggcacc agcagccaga     120
aaggttactt gtgacttgtt ttcagtgctt tcctgggagt gtcctgaaag ctggcagtgt     180
ttctgcctcg tcagaagagg cctcattcat tggggttgt accagcaact aaaaagttt      240 tttttttct tccctcttcc agtgttaata gattttgaaa gaggcatttt tgtttctaat      300
tacaaattcc tggtgatgt cattaagccc tcaaacaccc ggtgagggcg gcactgaatg      360
gggaaagaca atatgctaac aagttatctg agggtgtcag aaagaaatga tgaaaacag      420 tacagttggg ggaaatgttt tccagcctgc tttctggttt tagcgactgc atgggaagag      480
ataagacaca catggctttt ataaggagcc atcgggatct ctaggggaca tgaggcagga     540
gaaaagaatt gggctgaaag catccaatca tcacatattc acggagaaag agattacaat     600
atagcagagg aagctcttcc agggctccta cagggacctt tgggcaaaga ttcagtgggc     660
tttgggacag cttgacttca actagatggt atttgaataa tctgct                    706
```

<210> SEQ ID NO 17  
<211> LENGTH: 268  
<212> TYPE: DNA  
<213> ORGANISM: Artificial sequence  
<220> FEATURE:  
<223> OTHER INFORMATION: synthetic

<400> SEQUENCE: 17

```
ttagagggaa aacagacata gcaaacagag ccacgtttag tgatgaaact ctcactttgc      60
ctgagtcatg tgcggccatg cccaggggtc aggctgacac tcaactcaaa aacaagtgag     120
aaattgaaga caatccgtgg tggcagctac tggaagggcc accacatccc cagaaagagt     180
ggagctgcta aaaagccatt tgtgataggc acagttatct tgaatgcatg gagcagagat     240
tacggaaaaa tcgagaatgt taatgagg                                        268
```

<210> SEQ ID NO 18  
<211> LENGTH: 265  
<212> TYPE: DNA  
<213> ORGANISM: Rattus norvegicus

```
<400> SEQUENCE: 18
agctccagca agcacagcca catttaggga tgaaactctc actttgactg tgagtcacgt    60
gtagctgtgt cccgaggtca ggctggccct cagctcaaaa acaagtgagg gattgaagca   120
attactcaga taattcacag ccacagctac ggggagggcc gcatcccag aaacatcggg    180 gttactataa agctagtggt ggtcacagtt atcttgaatg tatggagcag aggagattac   240
agaaaaacct agaatgttaa tgagg                                         265

<210> SEQ ID NO 19
<211> LENGTH: 284
<212> TYPE: DNA
<213> ORGANISM: Mus musculus

<400> SEQUENCE: 19
agagagaaaa cagctacagc aaacagggcc acatttagtg acgaaactct cactttgact    60
gttgagtcat ttgcagtggg ccctgaggtc aggctggccc tcagctcaaa aacaagcgag   120
gaactgaagc aattactcag ataatccaca gccacagcca ctggaaaggg ccacatcccc   180
gagacagcac agcaggggtg ggggtggggc tatgagaaag ttagtgattg tagcagttat   240
ctagaatgtg cggagcagag gaggttacac aaaaacctag aatg                    284

<210> SEQ ID NO 20
<211> LENGTH: 287
<212> TYPE: DNA
<213> ORGANISM: Homo sapiens

<400> SEQUENCE: 20
ggagagaaaa cagatatagc acacactgtc acatttagcg ttgaaactct cggtttgact    60
atgagtaatg ttcagccatg cccaagggtc aggcctacac tcactcagaa acaagtgggg   120
aattgaagca attattcaga taatccatag acatagctac tggccagtgc tgcaccctg   180 atttagccca gaaacagtaa tgctattata agctgttggt gatttgtgga gcaatcttga   240
atttattaag gaaaggagat tatagaaaaa tccagaatgc caatggg                 287
```